US012778038B2

(12) United States Patent
Chen et al.

(10) Patent No.: US 12,778,038 B2
(45) Date of Patent: Nov. 3, 2026

(54) TRIKETONE DIOXYGENASE VARIANTS FOR HERBICIDE TOLERANCE

(71) Applicant: Monsanto Technology LLC, St. Louis, MO (US)

(72) Inventors: Danqi Chen, Ballwin, MO (US); Shunhong Dai, Creve Coeur, MO (US); David Duda, St. Louis, MO (US); Stephen M. Duff, St. Louis, MO (US); Clayton Larue, Chesterfield, MO (US); Qungang Qi, Chesterfield, MO (US); Lei Shi, San Diego, CA (US); Christina Taylor, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 100 days.

(21) Appl. No.: 18/835,341

(22) PCT Filed: Feb. 6, 2023

(86) PCT No.: PCT/US2023/062054
§ 371 (c)(1),
(2) Date: Aug. 1, 2024

(87) PCT Pub. No.: WO2023/150754
PCT Pub. Date: Aug. 10, 2023

(65) Prior Publication Data

US 2025/0134019 A1 May 1, 2025

Related U.S. Application Data

(60) Provisional application No. 63/307,525, filed on Feb. 7, 2022.

(51) Int. Cl.
*C12N 15/82* (2006.01)
*A01H 1/00* (2006.01)
(Continued)

(52) U.S. Cl.
CPC ............ *A01H 1/123* (2021.01); *A01H 1/021* (2021.01); *C07K 14/415* (2013.01); *C12N 5/04* (2013.01);
(Continued)

(58) Field of Classification Search
None
See application file for complete search history.

(56) References Cited

U.S. PATENT DOCUMENTS 8,299,318 B2 10/2012 Brover et al.
10,167,482 B2 1/2019 Coffin
(Continued)

FOREIGN PATENT DOCUMENTS

JP 2014011967 1/2014

OTHER PUBLICATIONS

Duff, Stephen MG, et al. "Structural and functional characterization of triketone dioxygenase from Oryza Sativa." Biochimica et Biophysica Acta (BBA)-General Subjects 1868.2 (2024): 130504. (Year: 2024).*
(Continued)

*Primary Examiner* — Weihua Fan
(74) *Attorney, Agent, or Firm* — Dentons US LLP; Elizabeth Millard

(57) ABSTRACT

The present disclosure relates to recombinant DNA molecules and engineered proteins useful for conferring tolerance to β-triketone herbicides such as mesotrione. The present disclosure also provides herbicide tolerant transgenic plants, plant parts, cells and seeds comprising the recombinant DNA molecules, and methods of using the same.

39 Claims, 15 Drawing Sheets

Specification includes a Sequence Listing.

(51) Int. Cl.
*A01H 1/02* (2006.01)
*C07K 14/415* (2006.01)
*C12N 5/04* (2006.01)
*C12N 15/52* (2006.01)

(52) U.S. Cl.
CPC .......... *C12N 15/52* (2013.01); *C12N 2510/00* (2013.01)

(56) References Cited

U.S. PATENT DOCUMENTS

| | | | |
|---|---|---|---|
| 2015/0047066 A1 | 2/2015 | Kato et al. | |
| 2016/0244777 A1* | 8/2016 | Coffin ................ | C12N 15/8251 |
| 2020/0048315 A1* | 2/2020 | Tozawa ................ | C12N 9/0071 |

OTHER PUBLICATIONS

Takamura, Natsuki, et al. "Catalytic promiscuity of rice 2-oxoglutarate/Fe (II)-dependent dioxygenases supports xenobiotic metabolism." Plant physiology 187.2 (2021): 816-828. (Year: 2021).*

Dai, et al. "Ectopic expression of a rice triketone dioxygenase gene confers mesotrione tolerance in soybean." Pest Manag Sci. 78(7): 2816-2827, (2022).

Larue, et al. "Microbial HemG-type protoporphyrinogen IX oxidase enzymes for biotechnology applications in plant herbicide tolerance traits." Pest Management Science 76, 1031-1038, (2020).

Maeda, et al. "A rice gene that confers broad-spectrum resistance to β-triketone herbicides." Science 365, 393-396, (2019).

Mitchell, et al. "Mesotrione: a new selective herbicide for use in maize." Pest Management Science 57, 120-128, (2001).

Sawant, et al. "Sequence architecture downstream of the initiator codon enhances gene expression and protein stability in plants." Plant Physiol. 126: 1630-1636, (2001).

Studier F.W. "Stable Expression Clones and Auto-Induction for Protein Production in *E. coli*", in: Y.W Chen (Ed), Structural Genomics: General Applications. Totowa, NJ, Humana Press. pp. 17-32, (2013).

EMBL Accession No. KAK3131749, submitted to database May 30, 2023.

GenBank Accession No. AFX27226, dated Nov. 14, 2012.

GenBank Accession No. QBD45578 dated Feb. 15, 2019.

Partial Supplementary European Search Report regarding European App. No. 23750490.7, mailed Dec. 9, 2025.

Sequence Listing of Japanese Pat. Pub. No. 2014011967, retrieved from https://globaldossier.uspto.gov/details/JP/2012150187/A/107622 on Jan. 8, 2026.

International Search Report and Written Opinion for International Application No. PCT/US2023/062054 mailed Jul. 26, 2023.

* cited by examiner

Figure 11

<table>
<tr><th></th><th colspan="4">Second Base in Codon</th><th></th></tr>
<tr><th>First Base in Codon</th><th>U</th><th>C</th><th>A</th><th>G</th><th>Third Base in Codon</th></tr>
<tr><td>U</td><td>UUU, UUC: Phe<br>UUA, UUG: Leu</td><td>UCU, UCC, UCA, UCG: Ser</td><td>UAU, UAC: Tyr<br>UAA Stop<br>UAG Stop</td><td>UGU, UGC: Cys<br>UGA Stop<br>UGG Trp</td><td>U<br>C<br>A<br>G</td></tr>
<tr><td>C</td><td>CUU, CUC, CUA, CUG: Leu</td><td>CCU, CCC, CCA, CCG: Pro</td><td>CAU, CAC: His<br>CAA, CAG: Gln</td><td>CGU, CGC, CGA, CGG: Arg</td><td>U<br>C<br>A<br>G</td></tr>
<tr><td>A</td><td>AUU, AUC, AUA: Ile<br>AUG Met or Start</td><td>ACU, ACC, ACA, ACG: Thr</td><td>AAU, AAC: Asn<br>AAA, AAG: Lys</td><td>AGU, AGC: Ser<br>AGA, AGG: Arg</td><td>U<br>C<br>A<br>G</td></tr>
<tr><td>G</td><td>GUU, GUC, GUA, GUG: Val</td><td>GCU, GCC, GCA, GCG: Ala</td><td>GAU, GAC: Asp<br>GAA, GAG: Glu</td><td>GGU, GGC, GGA, GGG: Gly</td><td>U<br>C<br>A<br>G</td></tr>
</table>

TRIKETONE DIOXYGENASE VARIANTS FOR HERBICIDE TOLERANCE

CROSS-REFERENCE TO RELATED APPLICATIONS

This application is a 371 National Phase application from International Patent Appl. No. PCT/US2023/062054, filed Feb. 6, 2023, which claims the priority of U.S. Provisional Appl. Ser. No. 63/307,525, filed Feb. 7, 2022, the entire disclosures of each are incorporated herein by reference in their entireties.

FIELD OF THE INVENTION

The present disclosure relates to the fields of agriculture, plant biotechnology, and plant molecular biology. More specifically, the present disclosure relates to recombinant DNA molecules encoding engineered proteins that are useful for conferring tolerance to β-triketone herbicides such as mesotrione, that are phytotoxic inhibitors of plant hydroxyphenylpyruvate dioxygenases (HPPD). The present disclosure also provides herbicide tolerant transgenic plants, plant parts, cells, and seeds comprising the recombinant DNA molecules, and methods of using the same.

INCORPORATION OF SEQUENCE LISTING

A computer readable form of a sequence listing is filed with this application by electronic submission and is incorporated into this application by reference in its entirety. The sequence listing is contained in the file named MONS_523WO_ST26, which is 89.7 kilobytes in size (measured in operating system MS Windows) and was created on Feb. 1, 2023.

BACKGROUND OF THE INVENTION

Agricultural crop production often utilizes transgenic traits created using the methods of biotechnology. A heterologous gene, also known as a transgene, can be introduced into a plant to produce a transgenic trait. Expression of the transgene in the plant confers a trait, such as herbicide tolerance, to the plant. Examples of transgenic herbicide tolerance traits include glyphosate tolerance, glufosinate tolerance, and dicamba tolerance. With the increase of weed species resistant to the commonly used herbicides, new herbicide tolerance traits are needed in the field. Herbicides of particular interest include herbicides that inhibit hydroxyphenylpyruvate dioxygenases (HPPD), referred to as HPPD inhibitor herbicides. HPPD inhibitor herbicides provide control of a spectrum of herbicide-resistant weeds, thus making a trait conferring tolerance to these herbicides particularly useful in a cropping system combined with one or more other herbicide-tolerance trait(s). Provided herein are novel, engineered enzymes useful for providing HPPD herbicide tolerance in plants.

SUMMARY OF THE INVENTION

Provided herein is a recombinant DNA molecule comprising a nucleic acid sequence encoding a protein having triketone dioxygenase (TDO) activity, wherein the protein has at least 70% sequence identity to an amino acid sequence selected from the group consisting of SEQ ID NOs: 2, 4, 6, 8, 10, 12, 14, and 16, wherein the protein comprises at least one amino acid substitution as compared to SEQ ID NO: 2, 4, 6, 8, 10, 12, 14, or 16, and wherein the protein comprises: a threonine (T), alanine (A), leucine (L), valine (V), isoleucine (I), serine(S), or glycine (G) at the position corresponding to position 230 of SEQ ID NO: 2; a serine(S) at the position corresponding to position 301 of SEQ ID NO: 2; an arginine (R) at the position corresponding to position 332 of SEQ ID NO: 2; an isoleucine (I) at the position corresponding to position 335 of SEQ ID NO: 2; a tyrosine (Y), phenylalanine (F), or histidine (H) at the position corresponding to position 141 of SEQ ID NO: 2; an alanine (A), isoleucine (I), leucine (L), serine(S), threonine (T), valine (V), or glycine (G) at the position corresponding to position 229 of SEQ ID NO: 2; an alanine (A), isoleucine (I), leucine (L), or valine (V), at the position corresponding to position 299 of SEQ ID NO: 2; or a combination of any thereof; provided that: (i) when a threonine (T), alanine (A), leucine (L), valine (V), isoleucine (I), or serine(S) is present at the position corresponding to position 230 of SEQ ID NO: 2, a glycine (G) is present at the position corresponding to position 229 of SEQ ID NO: 2; and (ii) when an alanine (A), leucine (L), valine (V), isoleucine (I), threonine (T), or serine(S) is present at the position corresponding to position 229 of SEQ ID NO: 2, a glycine (G) is present at the position corresponding to position 230 of SEQ ID NO: 2.

In some embodiments, a protein as described herein has at least 70% sequence identity to an amino acid sequence selected from the group consisting of SEQ ID NOs: 4, 6, 8, 10, 12, 14, and 16 and wherein the protein comprises: a threonine (T) at the position corresponding to position 230 of SEQ ID NO: 2; a serine(S) at the position corresponding to position 301 of SEQ ID NO: 2; an arginine (R) at the position corresponding to position 332 of SEQ ID NO: 2; an isoleucine (I) at the position corresponding to position 335 of SEQ ID NO: 2; or a combination of any thereof. In other embodiments, wherein the protein comprises: a threonine (T) at the position corresponding to position 230 of SEQ ID NO: 2; a serine(S) at the position corresponding to position 301 of SEQ ID NO: 2; an arginine (R) at the position corresponding to position 332 of SEQ ID NO: 2; and an isoleucine (I) at the position corresponding to position 335 of SEQ ID NO: 2. In certain embodiments, the protein has at least 70% sequence identity to SEQ ID NO: 2 and comprises one or more amino acid substitutions selected from the group consisting of H141F, H141Y, G229A, G229I, G229L, G229S, G229T, G229V, T230A, T230G, T230I, T230L, T230S, T230V, L299A, L299I, L299V, and combinations of any thereof. In some embodiments, the protein has at least 70% sequence identity to SEQ ID NO: 4 and comprises one or more amino acid substitutions selected from the group consisting of H141F, H141Y, A230G, A230I, A230L, A230S, A230T, A230V, G231A, G231I, G231L, G231S, G231T, G231V, F300A, F300I, F300L, F300V, G302S, I333R, and combinations of any thereof. In other embodiments, the protein comprises one or more amino acid substitutions selected from the group consisting of G231T, G302S, I333R, and combinations of any thereof. In further embodiments, the protein further comprises an isoleucine (I) at position 336 of SEQ ID NO: 4.

In additional embodiments, a protein as described herein has at least 70% sequence identity to SEQ ID NO: 6 and comprises one or more amino acid substitutions selected from the group consisting of Q140F, Q140H, Q140Y, G229A, G229I, G229L, G229S, G229T, G229V, P230A, P230G, P230I, P230L, P230S, P230T, P230V, L299A, L299I, L299V, A301S, L332R, V335I, and combinations of any thereof. In further embodiments, the protein comprises one or more amino acid substitutions selected from the group consisting of P230T, A301S, L332R, V335I, and combinations of any thereof. In some embodiments, the protein has at least 70% sequence identity to SEQ ID NO: 8 and comprises one or more amino acid substitutions selected from the group consisting of H144F, H144Y, G233A, G233I, G233L, G233S, G233T, G233V, G234A, G234I, G234L, G234S, G234T, G234V, F303A, F303I, F303L, F303V, G305S, L336R, F339I, and combinations of any thereof. In certain embodiments, the protein comprises one or more amino acid substitutions selected from the group consisting of G234T, G305S, L336R, F339I, and combinations of any thereof. In other embodiments, the protein has at least 70% sequence identity to SEQ ID NO: 10 and comprises one or more amino acid substitutions selected from the group consisting of H145F, H145Y, G234A, G234I, G234L, G234S, G234T, G234V, G235A, G235I, G235L, G235S, G235T, G235V, F304A, F304I, F304L, F304V, A306S, V337R, L340I, and combinations of any thereof. In certain embodiments, the protein comprises one or more amino acid substitutions selected from the group consisting of G235T, A306S, V337R, L340I, and combinations of any thereof. In some embodiments, the protein has at least 70% sequence identity to SEQ ID NO: 12 and comprises one or more amino acid substitutions selected from the group consisting of Q140F, Q140H, Q140Y, G229A, G229I, G229L, G229S, G229T, G229V, F299A, F299I, F299L, F299V, G230A, G230I, G230L, G230S, G230T, G230V, G301S, I332R, L335I, and combinations of any thereof. In certain embodiments, the protein comprises one or more amino acid substitutions selected from the group consisting of G230T, G301S, 1332R, L335I, and combinations of any thereof. In other embodiments, the protein has at least 70% sequence identity to SEQ ID NO: 14 and comprises one or more amino acid substitutions selected from the group consisting of H141F, H141Y, A212G, A212I, A212L, A212S, A212T, A212V, G213A, G213I, G213L, G213S, G213T, G213V, F282A, F282I, F282L, F282V, G284S, V315R, V318I, and combinations of any thereof. In further embodiments, the protein comprises one or more amino acid substitutions selected from the group consisting of G213T, G284S, V315R, V318I, and combinations of any thereof. In some embodiments, the protein has at least 70% sequence identity to SEQ ID NO: 16 and comprises one or more amino acid substitutions selected from the group consisting of Q140F, Q140H, Q140Y, G229A, G229I, G229L, G229S, G229T, G229V, F299A, F299I, F299L, F299V, G230A, G230I, G230L, G230S, G230T, G230V, G301S, I332R, L335R, and combinations of any thereof. In certain embodiments, the protein comprises one or more amino acid substitutions selected from the group consisting of G230T, G310S, 1332R, L335R, and combinations of any thereof. In some embodiments, the protein has at least 80% sequence identity to an amino acid sequence selected from the group consisting of SEQ ID NOs: 2, 4, 6, 8, 10, 12, 14, and 16. In other embodiments, the protein has at least 90% sequence identity to an amino acid sequence selected from the group consisting of SEQ ID NOs: 2, 4, 6, 8, 10, 12, 14, and 16. In certain embodiments, the protein comprises SEQ ID NO: 48. In further embodiments, the protein further comprises: a leucine (L) at the position corresponding to position 11 of SEQ ID NO: 2; a lysine (K) at the position corresponding to position 18 of SEQ ID NO: 2; a glutamine (Q) at the position corresponding to position 32 of SEQ ID NO: 2; a proline (P) at the position corresponding to position 35 of SEQ ID NO: 2; an isoleucine (I) at the position corresponding to position 48 of SEQ ID NO: 2; a glycine (G) at the position corresponding to position 54 of SEQ ID NO: 2; an isoleucine (I) at the position corresponding to position 82 of SEQ ID NO: 2; an aspartic acid (D) at the position corresponding to position 89 of SEQ ID NO: 2; a histidine (H) at the position corresponding to position 116 of SEQ ID NO: 2; a glutamic acid (E) at the position corresponding to position 120 of SEQ ID NO: 2; a valine (V) at the position corresponding to position 133 of SEQ ID NO: 2; a histidine (H) at the position corresponding to position 167 of SEQ ID NO: 2; a cysteine (C) at the position corresponding to position 173 of SEQ ID NO: 2; a phenylalanine (F) at the position corresponding to position 199 of SEQ ID NO: 2; a threonine (T) at the position corresponding to position 204 of SEQ ID NO: 2; a glycine (G) at the position corresponding to position 230 of SEQ ID NO: 2; a glycine (G) at the position corresponding to position 242 of SEQ ID NO: 2; a proline (P) at the position corresponding to position 256 of SEQ ID NO: 2; a serine(S) at the position corresponding to position 274 of SEQ ID NO: 2; a lysine (K) at the position corresponding to position 279 of SEQ ID NO: 2; or a combination of any thereof.

Also provided herein is a recombinant DNA molecule comprising a nucleic acid sequence encoding a protein having triketone dioxygenase (TDO) activity, wherein the protein has at least 50% identity to SEQ ID NO: 2 and comprises one or more amino acid substitutions selected from the group consisting of I11L, A18K, K32Q, S35P, L48I, S54G, V82I, S89D, N116H, Q120E, I133V, N167H, T173C, L199F, A204T, T230G, S242G, E256P, C274S, R279K, and combinations of any thereof. In some embodiments, the protein comprises I11L, A18K, K32Q, S35P, L48I, S54G, V82I, S89D, N116H, Q120E, I133V, N167H, T173C, L199F, A204T, T230G, S242G, E256P, C274S, and R279K amino acid substitutions. In other embodiments, the protein comprises I11L, A18K, K32Q, L48I, S54G, V82I, S89D, Q120E, I133V, N167H, T173C, L199F, A204T, T230G, S242G, E256P, C274S, and R279K amino acid substitutions. In certain embodiments, the protein comprises I11L, A18K, K32Q, L48I, S54G, V82I, S89D, N116H, I133V, N167H, T173C, L199F, A204T, T230G, S242G, E256P, C274S, and R279K amino acid substitutions. In some embodiments, the protein comprises I11L, A18K, K32Q, L48I, S54G, V82I, S89D, N116H, Q120E, I133V, N167H, T173C, L199F, A204T, T230G, E256P, C274S, and in R279K amino acid substitutions. In other embodiments, the protein comprises I11L, A18K, K32Q, S35P, L48I, S54G, V82I, S89D, Q120E, I133V, N167H, T173C, L199F, A204T, T230G, E256P, C274S, and R279K amino acid substitutions. In some embodiments, the protein comprises I11L, A18K, K32Q, S35P, L48I, S54G, V82I, S89D, N116H, I133V, N167H, T173C, L199F, A204T, T230G, E256P, C274S, and R279K amino acid substitutions. In other embodiments, the protein comprises I11L, A18K, K32Q, S35P, L48I, S54G, V82I, S89D, N116H, Q120E, I133V, N167H, T173C, L199F, A204T, T230G, C274S, and R279K amino acid substitutions. In further embodiments, the protein comprises I11L, A18K, K32Q, S35P, L48I, S54G, V82I, S89D, N116H, Q120E, I133V, N167H, T173C, L199F, A204T, T230G, E256P, and R279K amino acid substitutions. In certain embodiments, the protein comprises I11L, A18K, S35P, S54G, V82I, S89D, N116H, Q120E, N167H, T173C, L199F, A204T, T230G, C274S, and R279K amino acid substitutions. In other embodiments, the protein comprises I11L, A18K, K32Q, S35P, L48I, S54G, V82I, S89D, N116H, Q120E, I133V, N167H, T173C, A204T, T230G, S242G, E256P, and C274S amino acid substitutions. In some embodiments, the protein further comprises: a threonine (T) at the position corresponding to position 230 of SEQ ID NO: 2; a serine(S) at the position corresponding to position 301 of SEQ ID NO: 2; an arginine (R) at the position corresponding to position 332 of SEQ ID NO: 2; and an isoleucine (I) at the position corresponding to position 335 of SEQ ID NO: 2. In other embodiments, the protein has at least 80% identity to SEQ ID NO: 2. In further embodiments, the protein has at least 90% identity to SEQ ID NO: 2. In certain embodiments, the protein comprises SEQ ID NO: 18, 28, 30, 32, 34, 36, 38, 40, 42, or 44.

Provided herein is a recombinant DNA molecule comprising a nucleic acid sequence encoding a protein having triketone dioxygenase (TDO) activity, wherein the nucleic acid sequence comprises SEQ ID NO: 1. In some embodiments, the DNA molecule further comprises a heterologous promoter operably linked to the nucleic acid sequence encoding a protein having triketone dioxygenase (TDO) activity. In other embodiments, the promoter comprises a constitutive promoter. In further embodiments, the heterologous promoter is functional in a plant cell. In certain embodiments, the recombinant DNA molecule is comprised within a genome of a plant cell. DNA constructs comprising the recombinant DNA molecules and engineered proteins encoded by the recombinant DNA molecules described herein are also provided.

Also provided are transgenic plants, plant seeds, plant cells, or plant parts comprising the recombinant DNA molecule described herein. In some embodiments, the transgenic plant, plant seed, plant cell, or plant part is tolerant to at least one 4-hydroxyphenylpyruvate dioxygenase (HPPD) inhibitor herbicide. In other embodiments, the HPPD inhibitor herbicide is selected from the group consisting of mesotrione, benzobicyclon (BBC), tembotrione, sulcotrione, tefuryltrione, 2-(2-nitro-4-trifluoromethylbenzoyl)cyclohexane-1,3-dione (NTBC), pyrazolate, benzofenap, pyrazoxyfen, isoxaflutole, pyrazolynate, topramezone, and combinations of any thereof. In some embodiments, the transgenic plant, plant seed, plant cell, or plant part is tolerant to at least a second herbicide. In certain embodiments, the second herbicide is selected from the group consisting of an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor. In further embodiments, the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole. A commodity product comprising the recombinant DNA molecules described herein are also provided.

Further disclosed herein is a method for conferring HPPD inhibitor herbicide tolerance to a plant, plant seed, plant cell, or plant part, comprising heterologously expressing the engineered protein encoded by a recombinant DNA molecule comprising a nucleic acid sequence encoding a protein having triketone dioxygenase (TDO) activity, wherein the protein has at least 70% sequence identity to an amino acid sequence selected from the group consisting of SEQ ID NOs: 2, 4, 6, 8, 10, 12, 14, and 16, wherein the protein comprises at least one amino acid substitution as compared to SEQ ID NO: 2, 4, 6, 8, 10, 12, 14, or 16, and wherein the protein comprises: a threonine (T), alanine (A), leucine (L), valine (V), isoleucine (I), serine(S), or glycine (G) at the position corresponding to position 230 of SEQ ID NO: 2; a serine(S) at the position corresponding to position 301 of SEQ ID NO: 2; an arginine (R) at the position corresponding to position 332 of SEQ ID NO: 2; an isoleucine (I) at the position corresponding to position 335 of SEQ ID NO: 2; a tyrosine (Y), phenylalanine (F), or histidine (H) at the position corresponding to position 141 of SEQ ID NO: 2; an alanine (A), isoleucine (I), leucine (L), serine(S), threonine (T), valine (V), or glycine (G) at the position corresponding to position 229 of SEQ ID NO: 2; an alanine (A), isoleucine (I), leucine (L), or valine (V), at the position corresponding to position 299 of SEQ ID NO: 2; or a combination of any thereof; provided that: (i) when a threonine (T), alanine (A), leucine (L), valine (V), isoleucine (I), or serine(S) is present at the position corresponding to position 230 of SEQ ID NO: 2, a glycine (G) is present at the position corresponding to position 229 of SEQ ID NO: 2; and (ii) when an alanine (A), leucine (L), valine (V), isoleucine (I), threonine (T), or serine(S) is present at the position corresponding to position 229 of SEQ ID NO: 2, a glycine (G) is present at the position corresponding to position 230 of SEQ ID NO: 2 in the plant, plant seed, plant cell, or plant part.

Provided herein is a method for producing an herbicide tolerant plant, comprising: (a) transforming a plant cell with the recombinant DNA molecule described herein; and (b) regenerating a plant from the plant cell that comprises the recombinant DNA molecule. In some embodiments, the method further comprises selecting the plant or a progeny thereof for HPPD inhibitor tolerance. In other embodiments, the method comprises the step of crossing the regenerated plant with itself or with a second plant to produce progeny. Also provided herein is a method of producing a plant tolerant to an HPPD inhibitor herbicide and at least one other herbicide comprising: (a) crossing a plant provided herein with a second plant comprising tolerance to the at least one other herbicide, and (b) selecting a progeny plant resulting from said crossing that comprises tolerance to an HPPD inhibitor herbicide and the at least one other herbicide.

Also provided herein is a method for controlling or preventing weed growth in a plant growth area, comprising applying an effective amount of at least one HPPD inhibitor herbicide to a plant growth area that comprises the transgenic plants or seed provided herein, wherein the transgenic plant or seed is tolerant to the HPPD inhibitor herbicide. Also provided herein is a method of screening for a herbicide tolerance gene comprising: (a) expressing the recombinant DNA molecules of the present disclosure in a plant cell; and (b) identifying a plant cell that displays tolerance to an HPPD inhibitor herbicide. Also provided herein is a method for reducing the development of herbicide-tolerant weeds comprising: (a) cultivating in a crop growing environment a plant according to the present disclosure; and (b) applying an HPPD inhibitor herbicide and at least one other herbicide to the crop growing environment, wherein the crop plant is tolerant to the HPPD inhibitor herbicide and the at least one other herbicide.

BRIEF DESCRIPTION OF THE DRAWINGS

FIG. 1A shows an image of plants of transgenic event-125 treated with mesotrione, ranging from 1× to 16× of commercial rate.

Mesotrione herbicide rate is expressed as grams active ingredient per hectare (g a.i./ha); 1× commercial rate=105 g a.i./ha. FIG. 1B shows an image of wild-type control plants treated with mesotrione, ranging from 1× to 16× of commercial rate. FIG. 1C shows the mesotrione-induced injury rate in plants of TDO transgenic events and the wild-type control. Plants at V1 growth stage were sprayed with mesotrione (in Callisto®, Syngenta in 1% crop oil) at 1×, 2×, 4×, 8×, and 16× of commercial rate (equivalent to 105, 210, 420, 840, and 1680 g a.i./ha, respectively). Crop injury ratings were taken 13 days after mesotrione treatment. Each bar shows mean+/−standard error (SE).

FIG. 3A shows plants expressing Os·TDO-transgenic soybean event-125 treated with mesotrione grown at 99° F. (left) or 80° F. (middle), and treated wild-type plant grown at 80° F. (right). FIG. 3B shows the data showing correlation of increased mesotrione injury to decreased TDO protein levels in transgenic soybean plants grown under elevated temperature conditions. The black bars represent TDO protein levels in parts per million per dry weight; the gray bars represent plant injury rate (%) to 2× and 8× mesotrione treatments.

FIG. 4: Shows TDO expression levels in transgenic soybean plants, and corresponding responses to mesotrione injury at an elevated temperature. Soybeans were planted and grown under typical greenhouse conditions (85° F. day, 75° F. night) until approximately V3 growth stage. At that time, half of the plants were moved to a higher temperature growth chamber (99° F. day, 82° F. night; 60% relative humidity) for three days prior to leaf sample collection and a spray application of 4× rate mesotrione. Mesotrione was applied to both greenhouse and growth chamber plants. Visual injury ratings were taken at 7 days after treatment.

FIG. 5A shows protein level (ppm) from ELISA assay, for Os·TDO variants with improved enzyme stability at higher temperatures. The TDO variants were grown at 85° F. (gray) vs 99° F. (black). Os·TDO served as a control. FIG. 5B shows the % injury rating for soybean transgenic plants expressing Os·TDO and its variants after mesotrione applications. The TDO variants were grown at 85° F. (gray) vs 99° F. (black). Os·TDO served as a control.

FIG. 9A shows a sequence alignment of 11 TDO sequences from different plant species with *Arabidopsis* anthocyanidin synthase (also known as At·dioxy, or *Arabidopsis* leucoanthocyanidin dioxygenase). All residues within 7 Å of DQH (trans-dihydroquercetin) are highlighted in underlined and bold letters. Residues of interest are marked with numbers referencing the *Arabidopsis* anthocyanidin synthase (1GP5) crystal structure. Residues corresponding to amino acids 236, 306, 338, and 341 of At·dioxy (boxed with solid line) were explored experimentally, and residues corresponding to amino acids 144 and 304 of At·dioxy (boxed with dashed line) also may contribute to activity in monocots. The number in parentheses after each protein name corresponds to its SEQ ID NO. FIG. 9B shows the crystal structure of anthocyanidin synthase (1GP5) complexed with DQH (trans-dihydroquercetin, shown in light grey) with all residues with side chains within 7 Å of DQH highlighted in dark grey. FIG. 9C shows the 1GP5 structure with positions Phe144, Val235, Ser236, and Phe304 highlighted. DQH is shown in black. FIG. 9D shows a phylogenetic tree that was generated by running the aligned active site residues with 1000 rounds of bootstrapping using the RAxML program.

FIG. 11: Shows the universal genetic code chart showing all possible mRNA triplet codons (where T in the DNA molecule is replaced by U in the RNA molecule) and the amino acid encoded by each codon.

BRIEF DESCRIPTION OF THE SEQUENCES

Figure 1:
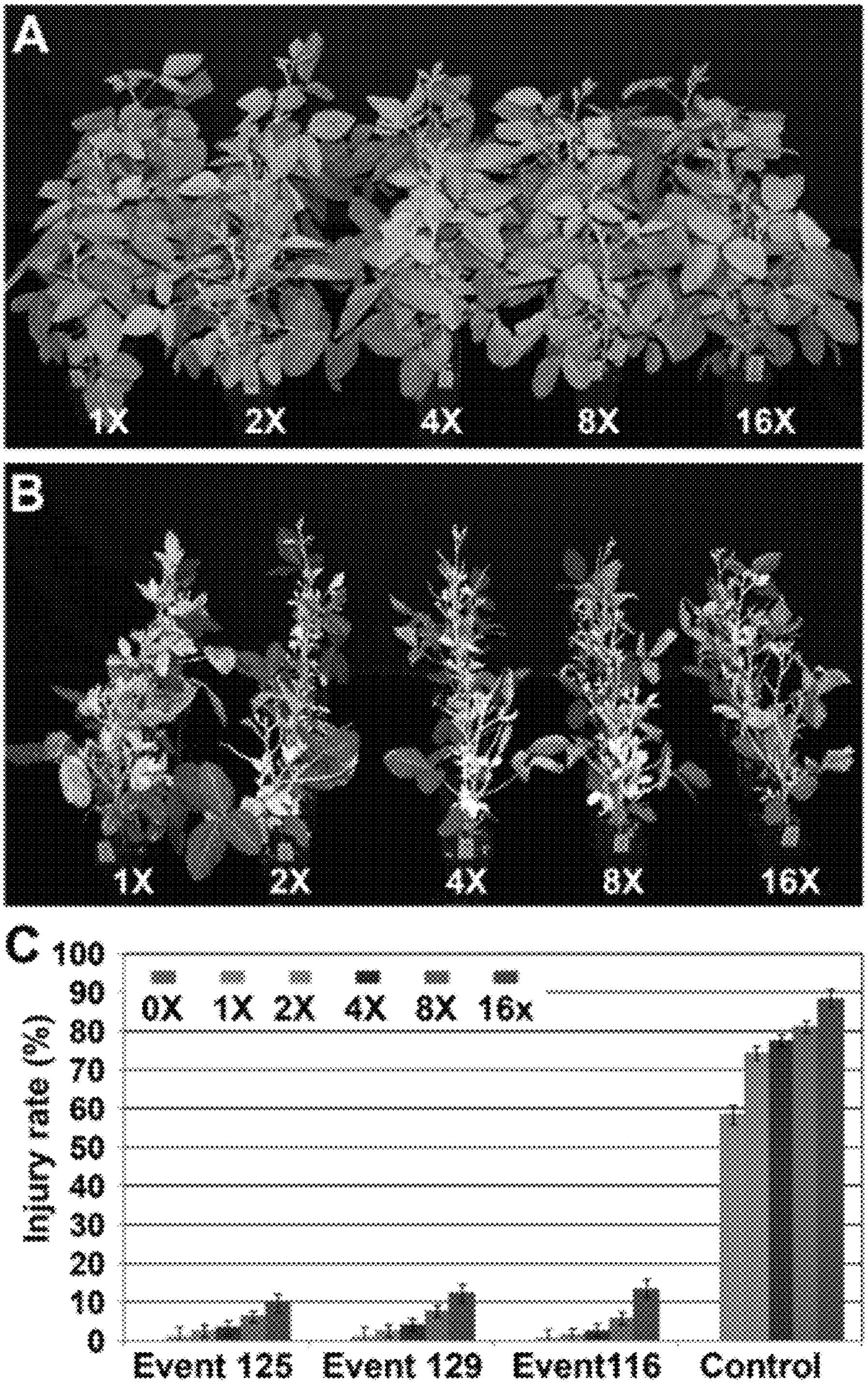
FIG. 1A, FIG. 1B, and FIG. 1C: Shows that constitutive expression of codon-optimized rice TDO (SEQ ID NO:2) in soybean conferred excellent tolerance to mesotrione.

SEQ ID NO:1 and SEQ ID NO:2 are the polynucleotide and amino acid sequences for Os·TDO, TDO from *Oryza sativa*. The polynucleotide sequence was codon optimized for dicot expression.

SEQ ID NO:3 and SEQ ID NO:4 are the polynucleotide and amino acid sequences for Zm·TDO, the TDO homolog from *Zea mays*. The polynucleotide sequence was codon optimized for dicot expression.

SEQ ID NO:5 and SEQ ID NO:6 are the polynucleotide and amino acid sequences for Sb·TDO, the TDO homolog from *Sorghum bicolor*. The polynucleotide sequence was codon optimized for dicot expression.

SEQ ID NO:7 and SEQ ID NO:8 are the polynucleotide and amino acid sequences for Si·TDO, the TDO homolog from *Setaria italica*. The polynucleotide sequence was codon optimized for dicot expression.

SEQ ID NO:9 and SEQ ID NO:10 are the polynucleotide and amino acid sequences for Ta·TDO, the TDO homolog from *Triticum aestivum*. The polynucleotide sequence was codon optimized for dicot expression.

SEQ ID NO:11 and SEQ ID NO:12 are the polynucleotide and amino acid sequences for ANDge·TDO, the TDO homolog from *Andropogon* gerardii. The polynucleotide sequence was codon optimized for dicot expression.

SEQ ID NO:13 and SEQ ID NO:14 are the polynucleotide and amino acid sequences for Cl·Col·TDO1, the TDO homolog from *Coix lacryma-jobi*. The polynucleotide sequence was codon optimized for dicot expression.

SEQ ID NO:15 and SEQ ID NO:16 are the polynucleotide and amino acid sequences for Cl·Col·TDO2, the TDO homolog from *Coix lacryma-jobi*. The polynucleotide sequence was codon optimized for dicot expression.

SEQ ID NO:17 and SEQ ID NO:18 are the polynucleotide and amino acid sequences for the Os·TDO variant D08. The polynucleotide sequence was codon optimized for dicot expression.

SEQ ID NO:19 and SEQ ID NO:20 are the polynucleotide and amino acid sequences of the Os·TDO variant B03. The polynucleotide sequence was codon optimized for dicot expression.

SEQ ID NO:21 and SEQ ID NO:22 are the polynucleotide and amino acid sequences for the Os·TDO variant F09. The polynucleotide sequence was codon optimized for dicot expression.

SEQ ID NO:23 and SEQ ID NO:24 are the polynucleotide and amino acid sequences for the Os·TDO variant A04. The polynucleotide sequence was codon optimized for dicot expression.

SEQ ID NO:25 and SEQ ID NO:26 are the polynucleotide and amino acid sequences for the Os·TDO variant B09. The polynucleotide sequence was codon optimized for dicot expression.

SEQ ID NO:27 and SEQ ID NO:28 are the polynucleotide and amino acid sequences for the Os·TDO variant TDO_1. The polynucleotide sequence was codon optimized for dicot expression.

SEQ ID NO:29 and SEQ ID NO:30 are the polynucleotide and amino acid sequences for the Os·TDO variant TDO_2. The polynucleotide sequence was codon optimized for dicot expression.

SEQ ID NO:31 and SEQ ID NO:32 are the polynucleotide and amino acid sequences for the Os·TDO variant TDO_3. The polynucleotide sequence was codon optimized for dicot expression.

SEQ ID NO:33 and SEQ ID NO:34 are the polynucleotide and amino acid sequences for the Os·TDO variant TDO_4. The polynucleotide sequence was codon optimized for dicot expression.

SEQ ID NO:35 and SEQ ID NO:36 are the polynucleotide and amino acid sequences for the Os·TDO variant TDO_5. The polynucleotide sequence was codon optimized for dicot expression.

SEQ ID NO:37 and SEQ ID NO:38 are the polynucleotide and amino acid sequences for the Os·TDO variant TDO_6. The polynucleotide sequence was codon optimized for dicot expression.

SEQ ID NO:39 and SEQ ID NO:40 are the polynucleotide and amino acid sequences for the Os·TDO variant TDO_7. The polynucleotide sequence was codon optimized for dicot expression.

SEQ ID NO:41 and SEQ ID NO:42 are the polynucleotide and amino acid sequences for the Os·TDO variant TDO_8. The polynucleotide sequence was codon optimized for dicot expression.

SEQ ID NO:43 and SEQ ID NO:44 are the polynucleotide and amino acid sequences for the Os·TDO variant TDO_9. The polynucleotide sequence was codon optimized for dicot expression.

SEQ ID NO:45 is a different codon-optimized polynucleotide sequence for the Os·TDO variant TDO_6. The corresponding amino acid sequence is SEQ ID NO:38.

SEQ ID NO:46 is a different codon-optimized polynucleotide sequence for the Os·TDO variant TDO_8. The corresponding amino acid sequence is SEQ ID NO:42.

SEQ ID NO:47 and SEQ ID NO:48 are the polynucleotide and amino acid sequences for the Sb·TDO variant SwM. The polynucleotide sequence was codon optimized for dicot expression.

SEQ ID NO:49 is the polynucleotide sequence for HIS1, the wild-type TDO from *Oryza sativa*. The corresponding amino acid sequence is SEQ ID NO:2.

SEQ ID NO:50 is the amino acid sequence for the leucoanthocyanidin dioxygenase (At·dioxy) from *Arabidopsis thaliana*. Leucoanthocyanidin dioxygenase is also known as anthocyanidin synthase.

SEQ ID NO:51 is the amino acid sequence for Gm·TDO, the TDO homolog from *Glycine max*.

SEQ ID NO:52 is the amino acid sequence for At·TDO, the TDO homolog from *Arabidopsis thaliana*.

SEQ ID NO:53 is the amino acid sequence for Nt·TDO, the TDO homolog from *Nicotiana tabacum*.

SEQ ID NO:54 is the amino acid sequence for the anthocyanidin synthase from *Arabidopsis thaliana*. It is identical to SEQ ID NO:50 with the exception of lacking the first methionine. SEQ ID NO: 54 is also referred to herein as 2BRT.

DETAILED DESCRIPTION

In plants, hydroxyphenylpyruvate dioxygenases (HPPD) are enzymes that are significant in catalyzing the biosynthesis of plastoquinone and tocopherols. Plastoquinone is a cofactor for phytoene desaturase, a key enzyme in the production of carotenoids. Carotenoids protect chlorophyll from degradation and are required for photosynthesis. Carotenoids and tocopherols are responsible for the detoxification of reactive oxygen species and scavenging of free radicals in plant tissues. Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photoprotection normally provided by carotenoids (Norris et al., 1995). Bleaching of photosynthetically active tissues leads to growth inhibition and plant death. Some molecules that inhibit HPPD have proven to be very effective herbicides. The triketone family is one of the most widely used HPPD inhibitor herbicides.

The present disclosure overcomes the limitations of the prior art by providing novel, engineered proteins, referred to herein as TDO proteins, and the recombinant DNA molecules that encode them as well as compositions and methods using these. The TDO proteins are proteins containing a Fe2OG dioxygenase domain that have the ability to inactivate triketone herbicides. As used herein, inactivating an herbicide means making the herbicide no longer have its herbicidal activity against a plant. The TDO proteins exhibit novel substrate selectivity, useful enzyme kinetics, and increased enzyme stability at elevated temperature. Transgenic plants expressing a TDO protein demonstrates improved tolerance to application of triketone herbicides.

I. Engineered Proteins and Recombinant DNA Molecules

Provided herein are novel, engineered proteins and the recombinant DNA molecules that encode them. As used herein, a TDO, "triketone dioxygenase," or a protein having "triketone dioxygenase activity" refers to a protein, specifically a Fe(II)/2-oxoglutarate-dependent dioxygenase, or a protein containing a Fe2OG dioxygenase domain that has the ability to hydroxylate a triketone herbicide. As used herein, the term "engineered" refers to a non-natural DNA, protein, cell, or organism that would not normally be found in nature and was created by human intervention. An "engineered protein," "engineered enzyme," or "engineered triketone dioxygenase," refers to a protein, enzyme, or triketone dioxygenase whose amino acid sequence was conceived of and created in the laboratory using one or more of the techniques of biotechnology, protein design, or protein engineering, such as molecular biology, protein biochemistry, bacterial transformation, plant transformation, site-directed mutagenesis, directed evolution using random mutagenesis, genome editing, gene editing, gene cloning, DNA ligation, DNA synthesis, protein synthesis, and DNA shuffling. For example, an engineered protein may have one or more deletions, insertions, or substitutions relative to the coding sequence of the wild-type protein and each deletion, insertion, or substitution may consist of one or more amino acids. Genetic engineering can be used to create a DNA molecule encoding an engineered protein, such as an engineered TDO protein and comprises at least a first amino acid substitution relative to a wild-type TDO protein as described herein.

Examples of engineered proteins provided herein are Fe2OG dioxygenase domain containing proteins having triketone dioxygenase activity (referred herein as "TDO proteins" or "TDO enzymes") comprising at least 70% sequence identity to an amino acid sequence selected from the group consisting of SEQ ID NOs: 2, 4, 6, 8, 10, 12, 14, and 16, wherein the protein comprises at least one amino acid substitution as compared to SEQ ID NO: 2, 4, 6, 8, 10, 12, 14, or 16, and wherein the protein comprises: a threonine (T), alanine (A), leucine (L), valine (V), isoleucine (I), serine(S), or glycine (G) at the position corresponding to position 230 of SEQ ID NO: 2; a serine(S) at the position corresponding to position 301 of SEQ ID NO: 2; an arginine (R) at the position corresponding to position 332 of SEQ ID NO: 2; an isoleucine (I) at the position corresponding to position 335 of SEQ ID NO: 2; a tyrosine (Y), phenylalanine (F), or histidine (H) at the position corresponding to position 141 of SEQ ID NO: 2; an alanine (A), isoleucine (I), leucine (L), serine(S), threonine (T), valine (V), or glycine (G) at the position corresponding to position 229 of SEQ ID NO: 2; an alanine (A), isoleucine (I), leucine (L), or valine (V), at the position corresponding to position 299 of SEQ ID NO: 2; or a combination of any thereof; provided that: (i) when a threonine (T), alanine (A), leucine (L), valine (V), isoleucine (I), or serine(S) is present at the position corresponding to position 230 of SEQ ID NO: 2, a glycine (G) is present at the position corresponding to position 229 of SEQ ID NO: 2; and (ii) when an alanine (A), leucine (L), valine (V), isoleucine (I), threonine (T), or serine(S) is present at the position corresponding to position 229 of SEQ ID NO: 2, a glycine (G) is present at the position corresponding to position 230 of SEQ ID NO: 2. In specific embodiments, an engineered protein provided herein comprises one, two, three, four, five, six, seven, eight, nine, ten, or more of any combination of such substitutions.

Engineered proteins are enzymes that have triketone dioxygenase activity. As used herein, "triketone dioxygenase activity" means the ability of a protein to inactivate one or more HPPD inhibitor herbicide(s). The term "triketone dioxygenase activity" means the ability to catalyze the hydroxylation of a triketone herbicide, such as mesotrione, thereby inactivating the herbicide. Enzymatic activity of a triketone dioxygenase can be measured by any means known in the art, for example, by an enzymatic assay in which the second hydroxylation of a triketone, such as production of oxy-mesotrione from mesotrione in the presence of a protein having triketone dioxygenase activity is measured via fluorescence, high performance liquid chromatography (HPLC), or mass spectrometry (MS).

As used herein, "wild-type" means naturally-occurring. As used herein, a "wild-type DNA molecule", "wild-type polypeptide", or a "wild-type protein" is a naturally-occurring DNA molecule, polypeptide, or protein, that is, a DNA molecule, polypeptide, or protein pre-existing in nature. A wild-type version of a polypeptide, protein, or DNA molecule may be useful for comparison with an engineered protein or gene. An example of a wild-type protein useful for comparison with the engineered proteins provided by the present disclosure is the HIS1 enzyme from *Oryza sativa*. An example of a wild-type DNA molecule useful for comparison with the recombinant DNA molecules provided by the present disclosure is the HIS1 gene from *Oryza sativa*. A wild-type version of a protein or DNA molecule may be useful as a control in an experiment.

A "wild-type plant" is a naturally occurring plant. Such wild-type plants may also be useful for comparison with a plant comprising a recombinant or engineered DNA molecule or protein. An example of a wild-type plant useful for comparison with plants comprising a recombinant or engineered DNA molecule or protein may be a plant of the same type as the plant comprising the engineered DNA molecule or protein, such as a protein conferring an herbicide tolerance trait, and as such is genetically distinct from the plant comprising the herbicide tolerance trait.

As used herein, "control" means an experimental control designed for comparison purposes. For example, a control plant in a transgenic plant analysis is a plant of the same type as the experimental plant (that is, the plant to be tested) but does not contain the transgenic insert, recombinant DNA molecule, DNA construct, or variant protein or gene of the experimental plant. Examples of control plants useful for comparison with transgenic plants include: for maize plants, non-transgenic LH244 maize (ATCC deposit number PTA-1173); for comparison with soybean plants: non-transgenic A3555 soybean (ATCC deposit number PTA-10207); for comparison with cotton plants: non-transgenic Coker 130 (Plant Variety Protection (PVP) Number 8900252); for comparison with canola or *Brassica napus* plants: non-transgenic *Brassica napus* variety 65037 Restorer line (Canada Plant Breeders' Rights Application 06-5517); for comparison with wheat plants: non-transgenic wheat variety Samson germplasm (PVP 1994). As used herein, the term "recombinant" refers to a non-naturally occurring DNA, protein, cell, seed, or organism that is the result of genetic engineering and was created by human intervention. A "recombinant DNA molecule" is a DNA molecule comprising a DNA sequence that does not naturally occur and as such is the result of human intervention, such as a DNA molecule comprising at least two DNA molecules heterologous to each other. An example of a recombinant DNA molecule is a DNA molecule provided herein encoding a protein having triketone dioxygenase activity operably linked to a heterologous promoter. A "recombinant protein" is a protein comprising an amino acid sequence that does not naturally occur and as such is the result of human intervention, such as an engineered protein. A recombinant cell, seed, or organism is a cell, seed, or organism comprising transgenic or heterologous DNA or protein, for example a transgenic plant cell, seed, or plant comprising a DNA construct or engineered protein of the present disclosure.

As used herein, the term "DNA" or "DNA molecule" refers to a double-stranded DNA molecule of genomic or synthetic origin (that is, a polymer of deoxyribonucleotide bases or a polynucleotide molecule) read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

The present disclosure provides a nucleic acid molecule encoding a protein having triketone dioxygenase activity comprising at least 70% sequence identity to an amino acid sequence selected from the group consisting of SEQ ID NOs: 2, 4, 6, 8, 10, 12, 14, and 16, wherein the protein comprises at least one amino acid substitution as compared to SEQ ID NO: 2, 4, 6, 8, 10, 12, 14, or 16, and wherein the protein comprises: a threonine (T), alanine (A), leucine (L), valine (V), isoleucine (I), serine(S), or glycine (G) at the position corresponding to position 230 of SEQ ID NO: 2; a serine(S) at the position corresponding to position 301 of SEQ ID NO: 2; an arginine (R) at the position corresponding to position 332 of SEQ ID NO: 2; an isoleucine (I) at the position corresponding to position 335 of SEQ ID NO: 2; a tyrosine (Y), phenylalanine (F), or histidine (H) at the position corresponding to position 141 of SEQ ID NO: 2; an alanine (A), isoleucine (I), leucine (L), serine(S), threonine (T), valine (V), or glycine (G) at the position corresponding to position 229 of SEQ ID NO: 2; an alanine (A), isoleucine (I), leucine (L), or valine (V), at the position corresponding to position 299 of SEQ ID NO: 2; or a combination of any thereof; provided that: (i) when a threonine (T), alanine (A), leucine (L), valine (V), isoleucine (I), or serine(S) is present at the position corresponding to position 230 of SEQ ID NO: 2, a glycine (G) is present at the position corresponding to position 229 of SEQ ID NO: 2; and (ii) when an alanine (A), leucine (L), valine (V), isoleucine (I), threonine (T), or serine(S) is present at the position corresponding to position 229 of SEQ ID NO: 2, a glycine (G) is present at the position corresponding to position 230 of SEQ ID NO: 2.

As used herein, the term "protein-coding DNA molecule" refers to a DNA molecule comprising a DNA sequence that encodes a protein. As used herein, the term "protein" refers to a chain of amino acids linked by peptide (amide) bonds and includes both polypeptide chains that are folded or arranged in a biologically functional way and polypeptide chains that are not. As used herein, a "protein-coding sequence" means a DNA sequence that encodes a protein. As used herein, a "sequence" means a sequential arrangement of nucleotides or amino acids. A "DNA sequence" may refer to a sequence of nucleotides or to the DNA molecule comprising of a sequence of nucleotides; a "protein sequence" may refer to a sequence of amino acids or to the protein comprising a sequence of amino acids. The boundaries of a protein-coding sequence are usually determined by a translation start codon at the 5'-terminus and a translation stop codon at the 3'-terminus.

Engineered proteins may be produced by changing or modifying a wild-type protein sequence to produce a new protein with modified characteristic(s) or a novel combination of useful protein characteristics, such as altered $V_{max}$, $K_m$, $K_i$, $IC_{50}$, substrate specificity, inhibitor/herbicide specificity, substrate selectivity, ability to interact with other components in the cell such as partner proteins or membranes, and protein stability, among others. Modifications may be made at specific amino acid positions in a protein and may be made by substituting an alternate amino acid for the typical amino acid found at that same position in nature (that is, in the wild-type protein). Amino acid modifications may be made as a single amino acid substitution in the protein sequence or in combination with one or more other modifications, such as one or more other amino acid substitution(s), deletions, or additions. In some embodiments, an engineered protein has altered protein characteristics, such as those that result in decreased sensitivity to one or more herbicides as compared to the wild-type protein or ability to confer tolerance to one or more herbicides on a transgenic plant expressing the engineered protein. In other embodiments, the present disclosure therefore provides an engineered protein such as a TDO protein, and the recombinant DNA molecule encoding it, having one or more amino acid substitution(s) selected from the group consisting of H141F, H141Y, G229A, G229I, G229L, G229S, G229T, G229V, T230A, T230G, T230I, T230L, T230S, T230V, L299A, L299I, L299V, and all combinations thereof, wherein the position of the amino acid substitution(s) is relative to the amino acid position set forth in SEQ ID NO: 2. In specific embodiments, an engineered protein provided herein comprises one, two, three, four, five, six, seven, eight, nine, ten, or more of any combination of such substitutions, wherein the modification is made at a position relative to a position comparable in function to that in the amino acid sequence provided as SEQ ID NO:2.

Figure 10:
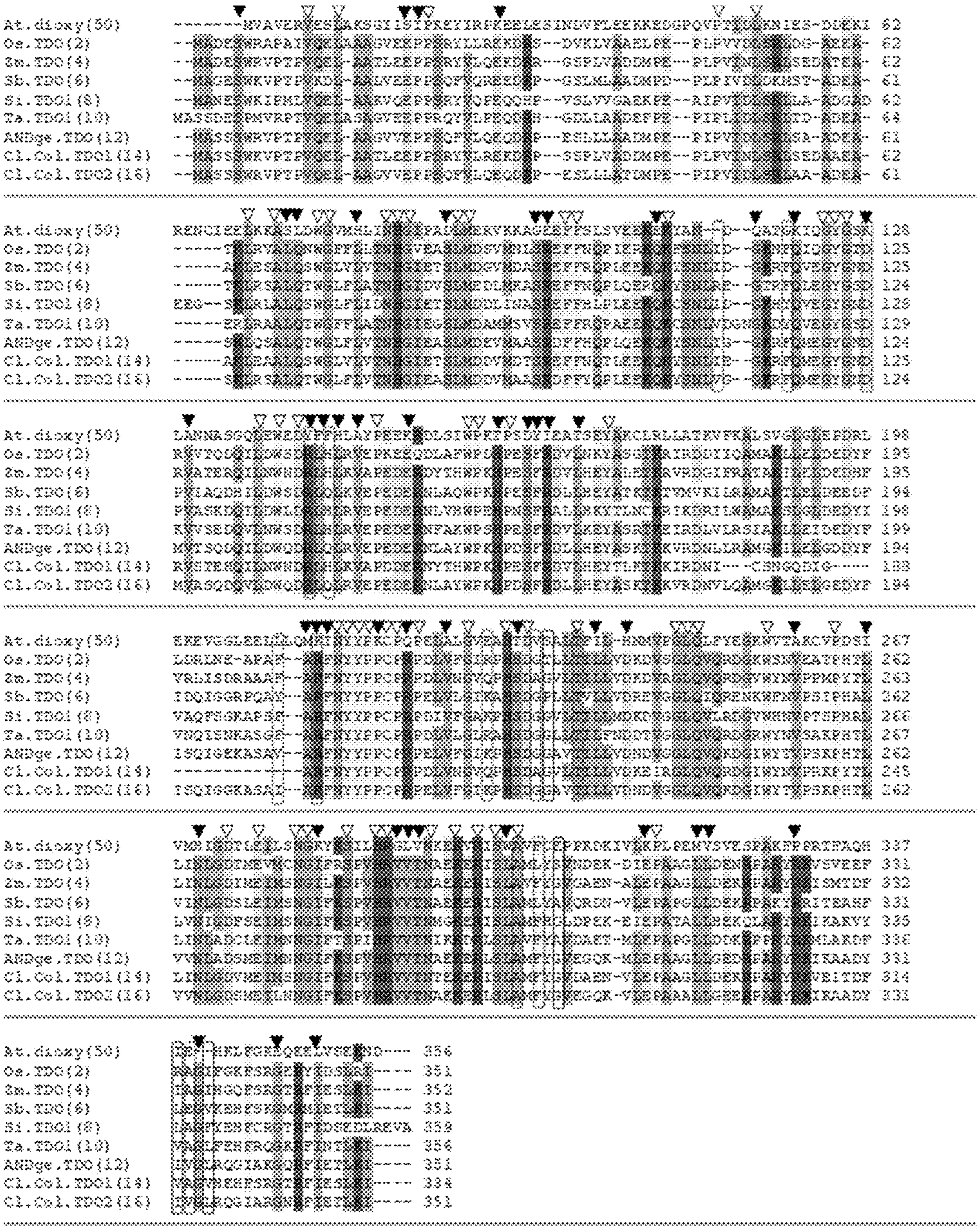
FIG. 10: Shows a protein sequence alignment of Os·TDO with its homologs from other plant species and a closely related protein, At·dioxy. The amino acid residues in solid boxes represent the unique amino acid residues T230, S301, R332, and I335 in the active site of Os·TDO. The boxes with a dashed line represent non-unique Os·TDO amino acid residues in the active site. Amino acid residues conserved only among the TDO protein sequences are indicated by a solid triangle; whereas residues conserved among all sequences are indicated with an open triangle. The number in parentheses after each protein name corresponds to its SEQ ID NO.

Similar modifications can be made in analogous positions of any protein containing a Fe2OG dioxygenase domain by alignment of the amino acid sequence of the Fe2OG dioxygenase domain containing protein to be mutated with the amino acid sequence of a Fe2OG dioxygenase domain containing protein that has triketone dioxygenase activity. One example of a sequence coding a Fe(II)/2-oxoglutarate-dependent dioxygenase that has triketone dioxygenase activity that can be used for alignment is SEQ ID NO:2. FIG. 10 show an alignment of Os·TDO, the TDO protein of SEQ ID NO:2 and homologs of Os·TDO (SEQ ID NOs: 4, 6, 8, 10, 12, 14, and 16). It is well within the capability of one of skill in the art to use sequence homology information, as shown in FIG. 10, to make the amino acid modifications described herein, for example, in the proteins of SEQ ID NOs: 2, 4, 6, 8, 10, 12, 14, or 16, to generate TDO proteins.

As used herein, the term "isolated" refers to at least partially separating a molecule from other molecules typically associated with it in its natural state. As used herein, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, as disclosed herein. For example, polymerase chain reaction (PCR) technology can be used to amplify a particular starting DNA molecule or to produce variants of the original molecule. DNA molecules, or fragment thereof, can also be obtained by other techniques, such as by directly synthesizing the fragment by chemical means, as is commonly practiced by using an automated oligonucleotide synthesizer.

Because of the degeneracy of the genetic code, a variety of different DNA sequences can encode proteins, such as the altered or engineered proteins disclosed herein. For example, FIG. 11 provides the universal genetic code chart showing all possible mRNA triplet codons (where T in the DNA molecule is replaced by U in the RNA molecule) and the amino acid encoded by each codon. DNA sequences encoding TDO proteins with the amino acid substitutions described herein can be produced by introducing mutations into the DNA sequence encoding a wild-type TDO protein using methods known in the art and the information provided in FIG. 11. It is well within the capability of one of skill in the art to create alternative DNA sequences encoding the same, or essentially the same, altered or engineered proteins as described herein. These variant or alternative DNA sequences are within the scope of the embodiments described herein. As used herein, references to "essentially the same" sequence refers to sequences which encode amino acid substitutions, deletions, additions, or insertions that do not materially alter the functional activity of the protein encoded by the DNA molecule of the embodiments described herein. Allelic variants of the nucleotide sequences encoding a wild-type or engineered protein are also encompassed within the scope of the embodiments described herein. Substitution of amino acids other than those specifically exemplified or naturally present in a wild-type or engineered TDO protein are also contemplated within the scope of the embodiments described herein, so long as the TDO protein e having the substitution still retains substantially the same functional activity described herein.

Recombinant DNA molecules provided herein may be synthesized and modified by methods known in the art, either completely or in part, where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present disclosure includes recombinant DNA molecules and engineered proteins having at least 50% sequence identity, at least 60% sequence identity, at least 70% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, and at least 99% sequence identity to any of the recombinant DNA molecule or amino acid sequences provided herein, and having triketone dioxygenase activity. As used herein, the term "percent sequence identity" or "% sequence identity" refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, CA), MEGAlign (DNAStar Inc., 1228 S. Park St., Madison, WI 53715), and MUSCLE (version 3.6) (R C Edgar, "MUSCLE: multiple sequence alignment with high accuracy and high throughput" *Nucleic Acids Research* 32 (5): 1792-7 (2004)) for instance with default parameters. An "identity fraction" for aligned segments of a test sequence and a reference sequence is the number of identical components that are shared by the two aligned sequences divided by the total number of components in the portion of the reference sequence segment being aligned, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

II. Expression Constructs

As used herein, a "DNA construct" is a recombinant DNA molecule comprising two or more heterologous DNA sequences. DNA constructs are useful for transgene expression and may be comprised in vectors and plasmids. DNA constructs may be used in vectors for transformation (that is, the introduction of heterologous DNA into a host cell) to produce recombinant bacteria or transgenic plants and cells (and as such may also be contained in the plastid DNA or genomic DNA of a transgenic plant, seed, cell, or plant part). As used herein, a "vector" means any recombinant DNA molecule that may be used for bacterial or plant transformation. DNA molecules provided herein can, for example, be inserted into a vector as part of a DNA construct having the DNA molecule operably linked to a heterologous gene expression element that functions in a plant to affect expression of the engineered protein encoded by the DNA molecule. Methods for making and using DNA constructs and vectors are well known in the art and described in detail in, for example, handbooks and laboratory manuals including Michael R. Green and Joseph Sambrook, "Molecular Cloning: A Laboratory Manual" (Fourth Edition) ISBN: 978-1-936113-42-2, Cold Spring Harbor Laboratory Press, NY (2012). The components for a DNA construct, or a vector comprising a DNA construct, include one or more gene expression elements operably linked to a transcribable nucleic acid sequence, such as the following: a promoter for the expression of an operably linked DNA, an operably linked protein-coding DNA molecule, and an operably linked 3' untranslated region (UTR). Gene expression elements that are useful include, but are not limited to, one or more of the following type of elements: promoter, 5' UTR, enhancer, leader, cis-acting element, intron, transit sequence, 3' UTR, and one or more selectable marker transgenes.

The term "transgene" refers to a DNA molecule artificially incorporated into the genome of an organism as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants provided herein comprise the recombinant DNA molecules and engineered proteins of the present disclosure.

As used herein, the term "heterologous" refers to the relationship between two or more things not normally associated in nature, for instance that are derived from different sources or not normally found in nature together in any other manner. For example, a DNA molecule or protein may be heterologous with respect to another DNA molecule, protein, cell, plant, seed, or organism if not normally found in nature together or in the same context. In certain embodiments, a first DNA molecule is heterologous to a second DNA molecule if the two DNA molecules are not normally found in nature together in the same context. For instance, a protein-coding recombinant DNA molecule is heterologous with respect to an operably linked promoter if such a combination is not normally found in nature. Similarly, a protein is heterologous with respect to a second operably linked protein, such as a transit peptide, if such combination is not normally found in nature. In another embodiment, a recombinant DNA molecule encoding a TDO protein is heterologous with respect to an operably linked promoter that is functional in a plant cell if such combination is not normally found in nature. A recombinant DNA molecule also may be heterologous with respect to a cell, seed, or organism into which it is inserted when it would not naturally occur in that cell, seed, or organism.

A "heterologous protein" is a protein present in a plant, seed, cell, tissue, or organism in which it does not naturally occur or operably linked to a protein with which it is not naturally linked. An example of a heterologous protein is an engineered TDO protein comprising at least a first amino acid substitution described herein that is expressed in any plant, seed, cell, tissue, or organism. Another example is a protein operably linked to a second protein, such as a transit peptide, with which it is not naturally linked, or a protein introduced into a plant cell in which it does not naturally occur using the techniques of genetic engineering.

As used herein, "operably linked" means two or more DNA molecules or two or more proteins linked in manner so that one may affect the function of the other. Operably linked DNA molecules or operably linked proteins may be part of a single contiguous molecule and may or may not be adjacent. For example, a promoter is operably linked with a protein-coding DNA molecule in a DNA construct where the two DNA molecules are so arranged that the promoter may affect the expression of the transgene.

The DNA constructs of the present disclosure may include a promoter operably linked to a protein-coding DNA molecule provided herein, whereby the promoter drives expression of the engineered protein. Promoters useful in practicing the contemplated embodiments include those that function in a cell for expression of an operably linked DNA molecule, such as a bacterial or plant promoter. Plant promoters are varied and well known in the art and include, for instance, those that are inducible, viral, synthetic, constitutive, temporally regulated, spatially regulated, or spatio-temporally regulated.

In some embodiments, a DNA construct provided herein includes a DNA sequence encoding a transit sequence that is operably linked to a heterologous DNA sequence encoding a TDO protein, whereby the transit sequence facilitates localizing the protein molecule within the cell. Transit sequences are known in the art as signal sequences, targeting peptides, targeting sequences, localization sequences, and transit peptides. An example of a transit sequence is a chloroplast transit peptide (CTP), a mitochondrial transit sequence (MTS), or a dual chloroplast and mitochondrial transit peptide. By facilitating protein localization within the cell, the transit sequence may increase the accumulation of recombinant protein, protect the protein from proteolytic degradation, or enhance the level of herbicide tolerance, and thereby reduce levels of injury in the cell, seed, or organism after herbicide application. CTPs and other targeting molecules that may be used in connection with the present disclosure are well known in the art.

As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins. A protein-coding DNA molecule may be operably linked to a heterologous promoter in a DNA construct for use in expressing the protein in a cell transformed with the recombinant DNA molecule.

III. Transgenic Plants

In one aspect, the present disclosure provides cells, tissues, plants, and seeds that comprising the recombinant DNA molecules or engineered proteins described herein. These cells, tissues, plants, and seeds comprising the recombinant DNA molecules or engineered proteins exhibit tolerance to one or more HPPD inhibitor herbicide(s).

One method of producing such cells, tissues, plants, and seeds is through plant transformation. Suitable methods for transformation of host plant cells for use with the present disclosure include any method by which DNA can be introduced into a cell (for example, where a recombinant DNA construct is stably integrated into a plant chromosome) and are well known in the art. Two effective, and widely utilized, methods for cell transformation are *Agrobacterium*-mediated transformation and microprojectile bombardment-mediated transformation. Microprojectile bombardment methods are illustrated, for example, in U.S. Pat. Nos. 5,550,318; 5,538,880; 6,160,208; and 6,399,861. *Agrobacterium*-mediated transformation methods are described, for example in U.S. Pat. No. 5,591,616. A cell with a recombinant DNA molecule or engineered protein of the present disclosure may be selected for the presence of the recombinant DNA molecule or engineered protein, for instance through its encoded enzymatic activity, before or after regenerating such a cell into a plant.

According to some embodiments, another method of producing the cells, plants, and seeds is through genome modification using site-specific integration or genome editing. Targeted modification of plant genomes through the use of genome editing methods can be used to create improved plant lines through modification of plant genomic DNA. As used herein "site-directed integration" refers to genome editing methods that enable targeted insertion of one or more nucleic acids of interest into a plant genome. Suitable methods for altering a wild-type DNA sequence or a pre-existing transgenic sequence or for inserting DNA into a plant genome at a pre-determined chromosomal site include any method known in the art. Exemplary methods include the use of sequence specific nucleases, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system). Several embodiments relate to methods of genome editing by using single-stranded oligonucleotides to introduce precise base pair modifications in a plant genome, as described by Sauer et al., Plant Physiology 170 (4): 1917-1928 (2016). Methods of genome editing to modify, delete, or insert nucleic acid sequences into genomic DNA are known in the art.

In some embodiments, the modification or replacement of an existing coding sequence, such as a TDO coding sequence or another existing transgenic insert, within a plant genome with a sequence encoding an engineered protein, such as an engineered TDO coding sequence provided herein, or an expression cassette encoding such an engineered protein is provided. Several embodiments relate to the use of a known genome editing methods, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system).

Several embodiments may therefore relate to a recombinant DNA construct comprising an expression cassette(s) encoding a site-specific nuclease and, optionally, any associated protein(s) to carry out genome modification. These nuclease-expressing cassette(s) may be present in the same molecule or vector as a donor template for templated editing or an expression cassette comprising nucleic acid sequence encoding a TDO protein as described herein (in cis) or on a separate molecule or vector (in trans). Several methods for site-directed integration are known in the art involving different sequence-specific nucleases (or complexes of proteins or guide RNA or both) that cut the genomic DNA to produce a double strand break (DSB) or nick at a desired genomic site or locus. As understood in the art, during the process of repairing the DSB or nick introduced by the nuclease enzyme, the donor template DNA, transgene, or expression cassette may become integrated into the genome at the site of the DSB or nick. The presence of the homology arm(s) in the DNA to be integrated may promote the adoption and targeting of the insertion sequence into the plant genome during the repair process through homologous recombination, although an insertion event may occur through non-homologous end joining (NHEJ).

As used herein, the term "double-strand break inducing agent" refers to any agent that can induce a double-strand break (DSB) in a DNA molecule. In some embodiments, the double-strand break inducing agent is a site-specific genome modification enzyme.

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof).

In some embodiments, the site-specific genome modification enzyme is a recombinase. Non-limiting examples of recombinases include a tyrosine recombinase attached to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Any of the DNA of interest provided herein can be integrated into a target site of a chromosome sequence by introducing the DNA of interest and the provided site-specific genome modification enzymes. Any method provided herein can utilize any site-specific genome modification enzyme provided herein.

IV. Herbicide Tolerant Plants

Provided herein are cells, plants, and seeds that are tolerant to HPPD inhibitor herbicides. Such cells, plants, and seeds are useful in the methods of agriculture, such as weed control and crop production.

As used herein, "herbicide" is any molecule that is used to control, prevent, or interfere with the growth of one or more plants. Exemplary herbicides include acetyl-CoA carboxylase (ACCase) inhibitors (for example aryloxyphenoxy propionates and cyclohexanediones); acetolactate synthase (ALS) inhibitors (for example sulfonylureas, imidazolinones, triazolopyrimidines, and triazolinones); 5-enolpyruvylshikimate-3-phosphate synthase (EPSPS) inhibitors (for example glyphosate), synthetic auxins (for example phenoxys, benzoic acids, carboxylic acids, semicarbazones), photosynthesis (photosystem II) inhibitors (for example triazines, triazinones, nitriles, benzothiadiazoles, and ureas), glutamine synthetase (GS) inhibitors (for example glufosinate and bialaphos), 4-hydroxyphenylpyruvate dioxygenase (HPPD) inhibitors (for example isoxazoles, pyrazolones, and triketones), protoporphyrinogen oxidase (PPO) inhibitors (for example diphenylethers, N-phenylphthalimide, aryl triazinones, and pyrimidinediones), very long-chain fatty acid inhibitors (for example chloroacetamides, oxyacetamides, and pyrazoles), cellulose biosynthesis inhibitors (for example indaziflam), photosystem I inhibitors (for example paraquat), microtubule assembly inhibitors (for example pendimethalin), and phytoene desaturase (PDS) inhibitors (for example norflurazone), among others.

As used herein, a "HPPD herbicide" is a chemical that targets and inhibits the enzymatic activity of 4-hydroxyphenyl-pyruvate-dioxygenase (HPPD), which is an Fe-containing enzyme that catalyzes the second reaction in the catabolism of tyrosine, the conversion of 4-hydroxyphenylpyruvate to homogentisate. Inhibition of 4-hydroxyphenyl-pyruvate-dioxygenase prevents plant carotenoid pigment formation, which in turn leads to chlorophyll degradation and eventually leads to lipid peroxidation of cell membranes. HPPD inhibitor herbicides are well-known in the art and commercially available. Examples of HPPD inhibitor herbicides include, but are not limited to, aclonifen, amitrole, beflubutamid, benzofenap, clomazone, diflufenican, fluridone, flurochloridone, flurtamone, isoxachlortole, isoxaflutole, mesotrione, norflurazon, picolinafen, pyrazolynate, pyrazoxyfen, sulcotrione, tembotrione, tolpyralate, topramezone and tefuryltrione salts and esters thereof, and mixtures thereof. Proteins having triketone dioxygenase activity and cells, seeds, plants, and plant parts provided by the present disclosure exhibit herbicide-tolerance to one or more HPPD inhibitor herbicide(s).

As used herein, "herbicide-tolerant" or "herbicide-tolerance" means the ability to be wholly or partially unaffected by the presence or application of one of more herbicide(s), for example to resist the toxic effects of an herbicide when applied. A cell or organism is "herbicide-tolerant" if it is able to maintain at least some normal growth or phenotype in the presence of one or more herbicide(s). A trait is an herbicide-tolerance trait if its presence can confer improved tolerance to an herbicide upon a cell, plant, or seed as compared to the wild-type or control cell, plant, or seed. Crops comprising a herbicide-tolerance trait can continue to grow and are minimally affected by the presence of the herbicide. A target enzyme is "herbicide-tolerant" if it exhibits improved enzyme activity relative to a wild-type or control enzyme in the presence of the herbicide. Herbicide-tolerance may be complete or partial insensitivity to a particular herbicide, and may be expressed as a percent (%) tolerance or insensitivity to a particular herbicide.

Contemplated plants which might be produced with an herbicide tolerance trait provided herein could include, for instance, any plant including crop plants such as soybean (*Glycine max*), maize (*Zea mays*), cotton (*Gossypium* sp.), and *Brassica* plants, among others.

Herbicides may be applied to a plant growth area comprising the plants and seeds provided by the present disclosure as a method for controlling weeds. Provided herein are plants and seeds that comprise an herbicide tolerance trait and as such are tolerant to the application of one or more HPPD inhibitor herbicides. The herbicide application may be the recommended commercial rate (1×) or any fraction or multiple thereof, such as twice the recommended commercial rate (2×). Herbicide rates may be expressed as acid equivalent per pound per acre (lb ae/acre) or acid equivalent per gram per hectare (g ae/ha) or as pounds active ingredient per acre (lb ai/acre) or grams active ingredient per hectare (g ai/ha), depending on the herbicide and the formulation. The herbicide application comprises at least one HPPD inhibitor herbicide. The plant growth area may or may not comprise weed plants at the time of herbicide application. A herbicidally-effective dose of HPPD inhibitor herbicide(s) for use in an area for controlling weeds may consist of a range from about 0.1× to about 30× label rate(s) over a growing season. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89=(lb ai/ac).

Herbicide applications may be sequential or tank mixed with one, two, or a combination of several HPPD inhibitor herbicides or any other compatible herbicide. Multiple applications of one herbicide or of two or more herbicides, in combination or alone, may be used over a growing season to areas comprising transgenic plants of the present disclosure for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant).

The transgenic plants, progeny, seeds, plant cells, and plant parts of the present disclosure may also contain one or more additional traits. Additional traits may be introduced by crossing a plant containing a transgene comprising the recombinant DNA molecules provided by the present disclosure with another plant containing one or more additional trait(s). As used herein, "crossing" means breeding two individual plants to produce a progeny plant. Two plants may thus be crossed to produce progeny that contain the desirable traits from each parent. As used herein "progeny" means the offspring of any generation of a parent plant, and transgenic progeny comprise a DNA construct provided by the present disclosure and inherited from at least one parent plant.

Additional trait(s) also may be introduced by co-transforming a DNA construct for that additional transgenic trait(s) with a DNA construct comprising the recombinant DNA molecules provided by the present disclosure (for example, with all the DNA constructs present as part of the same vector used for plant transformation) or by inserting the additional trait(s) into a transgenic plant comprising a DNA construct provided herein or vice versa (for example, by using any of the methods of plant transformation or genome editing on a transgenic plant or plant cell). Such additional traits include, but are not limited to, increased insect resistance, increased water use efficiency, increased yield performance, increased drought resistance, increased seed quality, improved nutritional quality, hybrid seed production, and herbicide-tolerance, in which the trait is measured with respect to a wild-type plant. Exemplary additional herbicide-tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazolopyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Examples of herbicide-tolerance proteins useful for producing additional herbicide-tolerance traits are well known in the art and include, but are not limited to, glyphosate-tolerant 5-enolypyruvyl shikimate 3-phosphate synthases (e.g., CP4 EPSPS, 2mEPSPS), glyphosate oxidoreductases (GOX), glyphosate N-acetyltransferases (GAT), herbicide-tolerant acetolactate synthases (ALS) acetohydroxyacid synthases (AHAS), herbicide-tolerant 4-hydroxyphenylpyruvate dioxygenases (HPPD), dicamba monooxygenases (DMO), phosphinothricin acetyl transferases (PAT), herbicide-tolerant glutamine synthetases (GS), 2,4-dichlorophenoxyproprionate dioxygenases (TfdA), R-2,4-dichlorophenoxypropionate dioxygenases (RdpA), S-2,4-dichlorophenoxypropionate dioxygenases (SdpA), herbicide-tolerant protoporphyrinogen oxidases (PPO), and cytochrome P450 monooxygenases. Exemplary insect resistance traits may include resistance to one or more insect members within one or more of the orders of Lepidoptera, Coleoptera, Hemiptera, Thysanoptera, Diptera, Hymenoptera, and Orthoptera, among others. Such additional traits are well known to one of skill in the art; for example, and a list of such transgenic traits is provided by the United States Department of Agriculture's (USDA) Animal and Plant Health Inspection Service (*APHIS*).

Transgenic plants and progeny that are tolerant to HPPD inhibitor herbicides may be used with any breeding methods that are known in the art. In plant lines comprising two or more traits, the traits may be independently segregating, linked, or a combination of both in plant lines comprising three or more transgenic traits. Backcrossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and also, by analyzing the phenotype of the whole plant.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

As used herein, the term "comprising" means "including but not limited to".

Having described the present disclosure in detail, it will be apparent that modifications, variations, and equivalent embodiments are possible without departing from the spirit and scope of the present disclosure as further defined in the appended claims. Furthermore, it should be appreciated that all examples in the present disclosure including the following are provided as non-limiting examples.

EXAMPLES

Example 1: Ectopic Expression of TDO Codon-Optimized Protein in Soybean Confers Excellent Mesotrione Tolerance Mesotrione, a β-triketone herbicide, is an extremely potent competitive inhibitor of 4-Hydroxyphenylpyruvate dioxygenase (HPPD), and has been developed as a selective herbicide for many crops, including corn. Mesotrione provides pre-emergence and post-emergence control of many important broad-leaf weeds and some annual grass weeds in corn fields (Mitchell et al., 2001). However, it cannot be used to manage weeds in soybean fields due to soybean's sensitivity to mesotrione (Mitchell et al., 2001). Development of soybean plants that can tolerate two times (2×) the herbicide application rates recommended for commercial use of mesotrione and resulting in a herbicide injury rate lower than 10% will offer soybean farmers an additional tool to manage weeds.

The rice HPPD Inhibitor Sensitive 1 (HIS1) gene was found to confer tolerance to β-triketone herbicides, including mesotrione, although the level of tolerance was not evaluated to determine if it is sufficient to serve for commercial use (Maeda et al., 2019). HIS1 encodes a Fe(II)/2-oxoglutarate-dependent dioxygenase that catalyzes the hydroxylation of a number of β-triketone herbicides such as benzobicyclon, tefuryltrione, sulcotrione, mesotrione, and tembotrione, leading to their inactivation. To test whether ectopic expression of the rice HIS1 gene in soybean can confer sufficient tolerance to mesotrione for trait development, the rice HIS1 gene sequence was codon-optimized for expression in soybean and designated as Os·TDO (SEQ ID NO: 2).

The Os·TDO sequence was cloned into a set of binary vectors using standard cloning methods known in the art with its expression driven by different constitutive promoters and different 3'UTRs. Transgenic soybean plants comprising these constructs were developed using an *Agrobacterium*-mediated transformation system as described in Larue et al. (2020). The copy number of the transgene was determined via a Taqman assay and events with a single copy of the T-DNA insertion were selected for evaluation of mesotrione tolerance. Briefly, R2 and later generation homozygous lines of three soybean transgenic events derived from Construct 32 were selected for a mesotrione tolerance greenhouse assay. Construct 32 contained two expression cassettes between the T-DNA borders: one for expression of Os·TDO and the other for expression of a selectable marker. The Os·TDO cassette utilized the cauliflower mosaic virus (CaMV) 35S promotor and the 5' UTR of HSP70 from *petunia* to drive expression of Os·TDO, followed by the 3' UTR of the nopaline synthase (nos) gene from the T-DNA region of the Ti plasmid of *Agrobacterium tumefaciens*, which functions to direct polyadenylation of the mRNA. The selectable marker cassette conferring spectinomycin and streptomycin resistance comprises the promoter, intron, and leader sequences from the *Arabidopsis thaliana* actin 7 gene, the transit peptide region of *Arabidopsis thaliana* EPSPS, the coding region of the Tn7 adenylyltransferase (AAD (3")) gene from *E. coli*, and the 3' non-translated region from the *Agrobacterium tumefaciens* nopaline synthase gene.

Each plant was grown in a 3.5" pot with soybean potting media in a growth chamber under conditions of 28° C./24° C. (light/dark) and a photoperiod of 16 hr light at 700 μE/8 hr dark, and fertilized with Peters general purpose fertilizer. Eight plants at V1 growth stage were sprayed with mesotrione (in Callisto®, Syngenta in 1% crop oil) at 1×, 2×, 4×, 8×, and 16× of commercial rate (equivalent to 105, 210, 420, 840, and 1680 g active ingredient/ha, respectively). Crop injury ratings were taken 13 days after mesotrione treatment.

Figure 2:
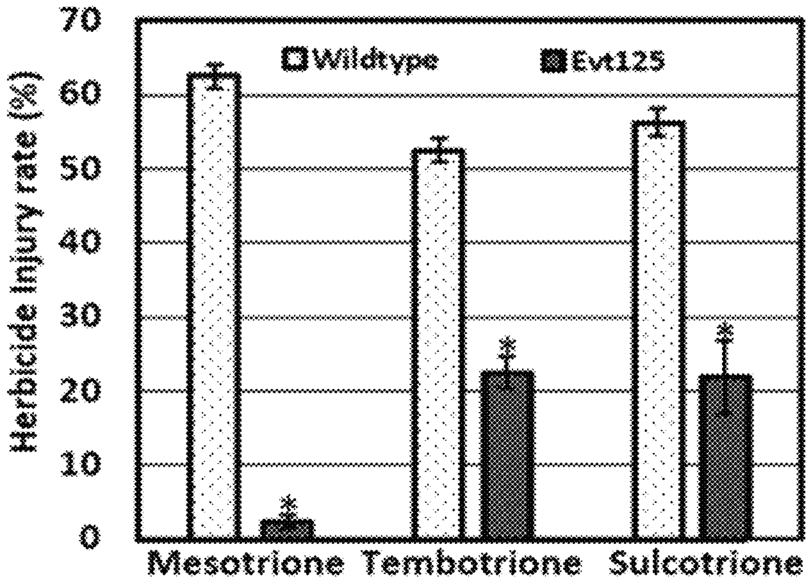
FIG. 2: Shows that expression of Os·TDO in transgenic soybean plants resulted in tolerance to tembotrione and sulcotrione, in addition to mesotrione. Os·TDO transgenic event-125 and wild-type control plants were sprayed with 2× of commercial rate of mesotrione (Callisto, 210 g a.i./ha), tembotrione (Laudis, 184 g a.i./ha) and sulcotrione (Sulcogan, 660 g a.i./ha). Each bar represents the mean of injury rating of 8 reps+/−SE. * indicates significant difference vs corresponding control at $p<0.01$.

As shown in FIGS. 1A and 1C, the three transgenic events demonstrated excellent tolerance to up to 16× of commercial application rate of mesotrione (1×=105 g a.i./ha) without off-types, while wild-type control plants were severely injured by mesotrione at all rates applied (FIGS. 1B and 1C). The injury rate of all TDO transgenic events was lower than 10% when treated at 8× or lower rate of mesotrione. The injury rate remained below 15% among the events when treated with an extremely high dose of mesotrione (16×) (FIG. 1C). In addition, expression of Os·TDO in soybean provided tolerance to two other triketone HPPD inhibitors, tembotrione and sulcotrione, although the level of tolerance was not as strong as was observed for mesotrione (FIG. 2).

Example 2: Identification and Screening of TDO Homologs for Mesotrione Tolerance To investigate if HIS1 from other species could also provide tolerance to HPPD-inhibiting herbicides, homologs from different plant species were identified using bioinformatic methods known in the art. Plant expression vectors containing TDO homolog sequences from *Zea mays, Sorghum bicolor, Setatria italica, Triticum aestivum, Andropogon gerardii, Coix* lacryma-jobi, and *Oryza sativa* were constructed and verified using standard molecular cloning techniques. These homolog sequences were optimized for enhanced expression in dicots using an in-house sequence optimization program. The nucleotides downstream of the ATG (nucleotide positions +4 to +11) of the wheat TDO sequence were codon-optimized as ATGGCttcctc for enhanced protein expression in plants (Sawant et al., 2001). This resulted in the amino acid substitution of alanine to serine at the 4th amino acid position from the N-terminus (A4S). Table 1 provides information regarding the sequences identified in other plant species.

TABLE 1

Rice TDO and homologs from other plant species.

| Gene Name | Gene ID | Species | % Identity to Os.TDO | Polynucleotide SEQ ID NO | Polypeptide SEQ ID NO |
|---|---|---|---|---|---|
| Os.TDO | Os02g0280700 (codon optimized) | *Oryza sativa* | 100 | 1 | 2 |
| Zm.TDO | 17IVI17_SF135702.G5060.1 (internal) | *Zea mays* | 68.5 | 3 | 4 |
| Sb.TDO | Sb10g005200.1 | *Sorghum bicolor* | 60.1 | 5 | 6 |
| Si.TDO | sf00110g576250 | *Setaria italica* | 60.2 | 7 | 8 |
| Ta.TDO | Traes_5BL_10EF2471E.1 | *Triticum aestivum* | 61.8 | 9 | 10 |
| ANDgeTDO | TRPT0111786 | *Andropogon gerardii* | 63.0 | 11 | 12 |
| Cl.Col.TDO1 | Coix contig_41968_1 | *Coix lacryma-jobi* | 66.2 | 13 | 14 |
| Cl.Col.TDO2 | Coix contig_459256_1 | *Coix lacryma-jobi* | 63.5 | 15 | 16 |

Plant expression vectors comprising the selected TDO homologs under the control of one of two constitutive promoters were transformed into soybean via an *Agrobacterium tumefaciens*-mediated method. Following *Agrobacterium* transformation, $R_0$ transgenic soybean plants containing a single copy of the transgene were identified through molecular characterization and segregation analysis. Transgenic and wild-type (control) plants were grown in 6-inch pots filled with BM7 soilless mix in a growth chamber under the conditions of 28° C./23° C. (light/dark) and a 16 hr light/8 hr dark photoperiod. Plants were fertilized with 15-5-15 liquid fertilizer at the V3-V4 growth stage and treated with 210 g a.i./ha mesotrione (1×=105 g a.i./ha; Callisto®, Syngenta in 1% crop oil). Plants were visually rated 7-14 days after treatment on a scale of 0% to 100%, with 0%=no injury and 100%=plant death, relative to the wild-type controls. The results summarized in Table 2 represent the mean of all tested events (10-15) for each construct.

TABLE 2

Mesotrione injury of transgenic soybean plants expressing TDO homologs.

| Construct | Promoter | Gene Name | Source Species | 3' UTR | % Injury |
|---|---|---|---|---|---|
| 1 | Constitutive 1 | Os.TDO | *Oryza sativa* | A | 5 |
| 2 | Constitutive 1 | Zm.TDO | *Zea mays* | A | 15 |
| 3 | Constitutive 1 | Sb.TDO | *Sorghum bicolor* | A | 35 |
| 4 | Constitutive 1 | Si.TDO | *Setatria italica* | A | 35 |
| | | Wild-type control | | | 55 |
| 5 | Constitutive 2 | Ta.TDO | *Triticum aestivum* | B | 50 |
| 6 | Constitutive 2 | ANDge.TDO | *Andropogon gerardii* | B | 55 |
| 7 | Constitutive 2 | Cl.Col.TDO1 | *Coix lacryma-jobi* | B | 61 |
| 8 | Constitutive 2 | Cl.Col.TDO2 | *Coix lacryma-jobi* | B | 53 |
| 9 | Constitutive 2 | Os.TDO | *Oryza sativa* | B | 12 |
| | | Wild-type control | | | 60 |

The results in Table 2 show that transgenic plants expressing Os·TDO had minimal mesotrione injury. While homologs from corn, sorghum, and Setatria *italica* showed reduced but still significant injury, those from wheat, *Andropogon* gerardii, and *Coix lacryma-jobi* did not seem to provide any protection against mesotrione.

Example 3: Improved Mesotrione Tolerance Through Enhanced Expression

Crop plants are often grown in diverse locations throughout the world, which can expose the plants to a wide range of climatic conditions. One of these climatic variables includes a wide range of temperatures. Previous work on herbicide tolerance trait development has shown that is often necessary that the enzymes conferring these traits are stable at higher temperatures (such as field situations) in order to build a robust tolerance trait.

Figure 3:
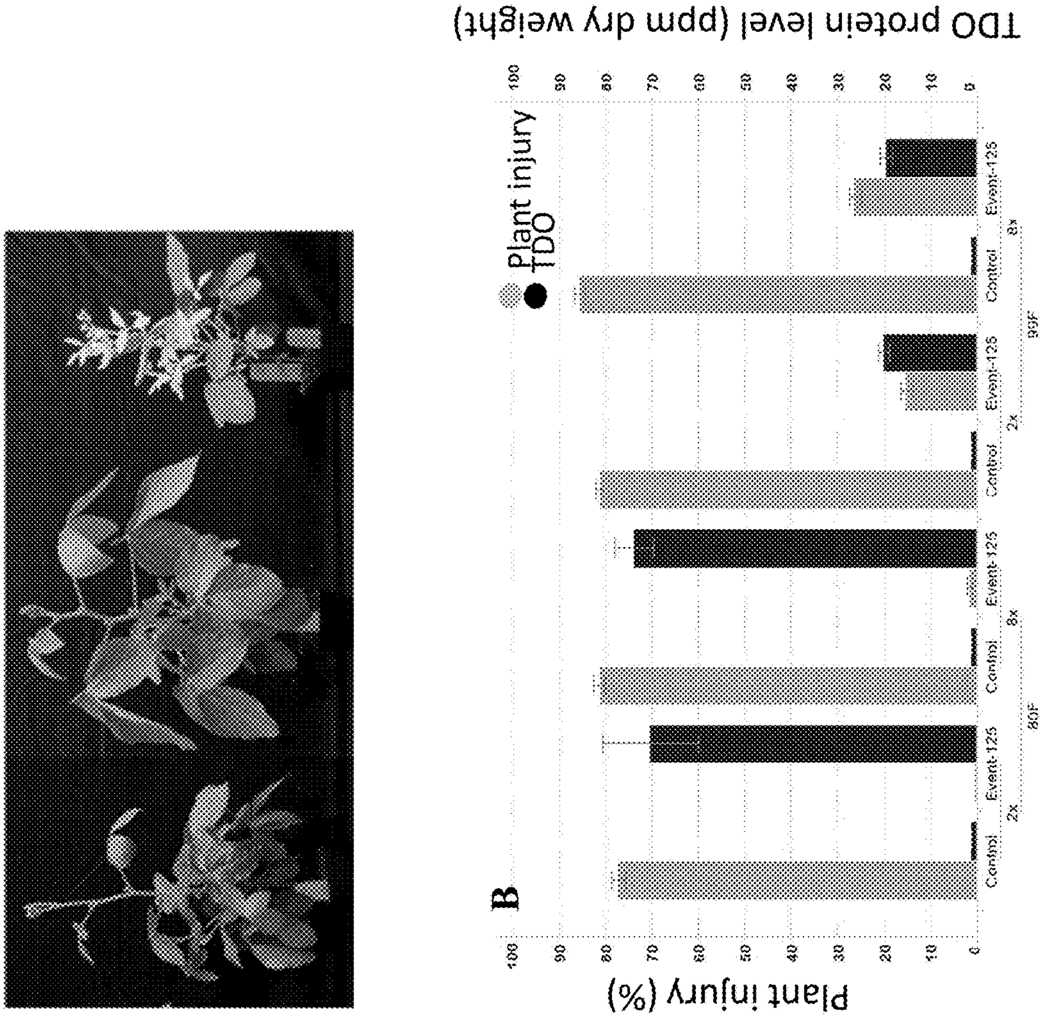
FIG. 3A and FIG. 3B: Shows the effect of elevated temperature on mesotrione injury and its correlation to decreased TDO protein level as detected by ELISA. Os·TDO-transgenic soybean plants and wild-type control plants were grown at 80° F. until V2 growth stage, then half of the plants were transferred to 99° F. After 3 days, leaf samples were harvested to determine TDO protein levels, and plants were then treated with 2× and 8× rates of mesotrione. Crop injury ratings were taken 11 days after mesotrione treatment.

As shown in the previous examples, expression of Os·TDO in transgenic soybean plants provides tolerance to the mesotrione. However, the trait performance declined when the plants were grown in growth chamber experiments in which the temperature was increased to mimic a hot field environment. This decline in performance was linked to a decline in TDO protein expression (FIG. 3).

To address TDO protein instability at higher temperatures, one of the approaches taken was to improve expression of TDO protein through selection of expression elements in the plant transformation constructs, especially promoters. Experiments were conducted in which transgenic soybean plants expressing Os·TDO under the control of a strong constitutive promoter (Construct 32), a medium constitutive promoter A (Construct 9), and a different medium constitutive promoter B(Construct 1) were grown in growth chambers at 85° F. or 99° F. At V3-V4 growth stage, these plants were treated with 4× mesotrione (420 g a.i./ha; 1×=105 g a.i./ha; in Callisto®, Syngenta in 1% crop oil). Plants were visually rated 7-14 days after treatment on a scale of 0% to 100%, with 0%=no injury and 100%=plant death, relative to the untreated transgenic and wild-type controls.

Figure 4A:
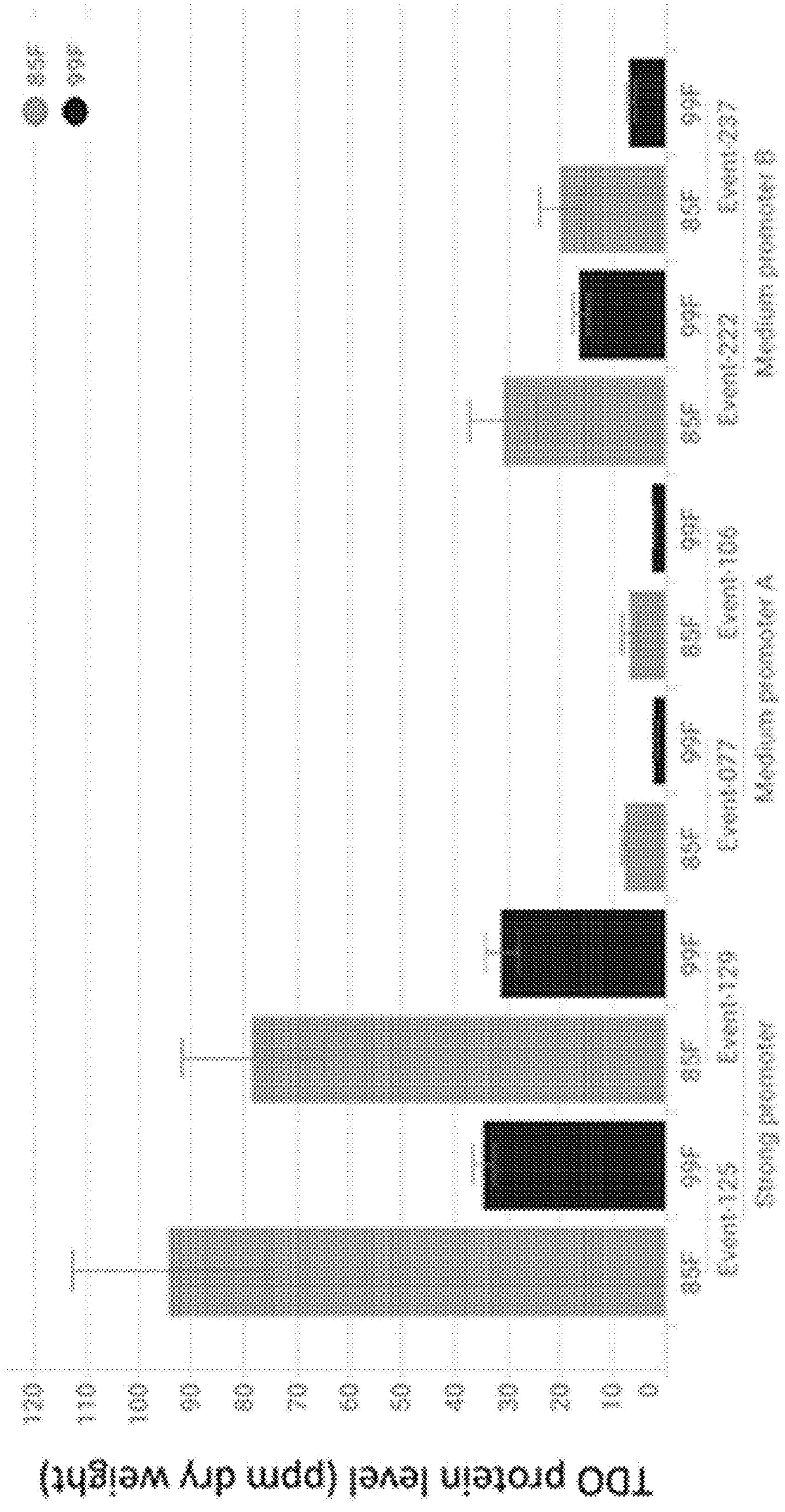
FIG. 4A shows the Os·TDO protein levels in parts per million (ppm) in transgenic soybean plants with Os·TDO driven by a strong constitutive promoter, and two different medium constitutive promoters (Medium A and Medium B).
Figure 4B:
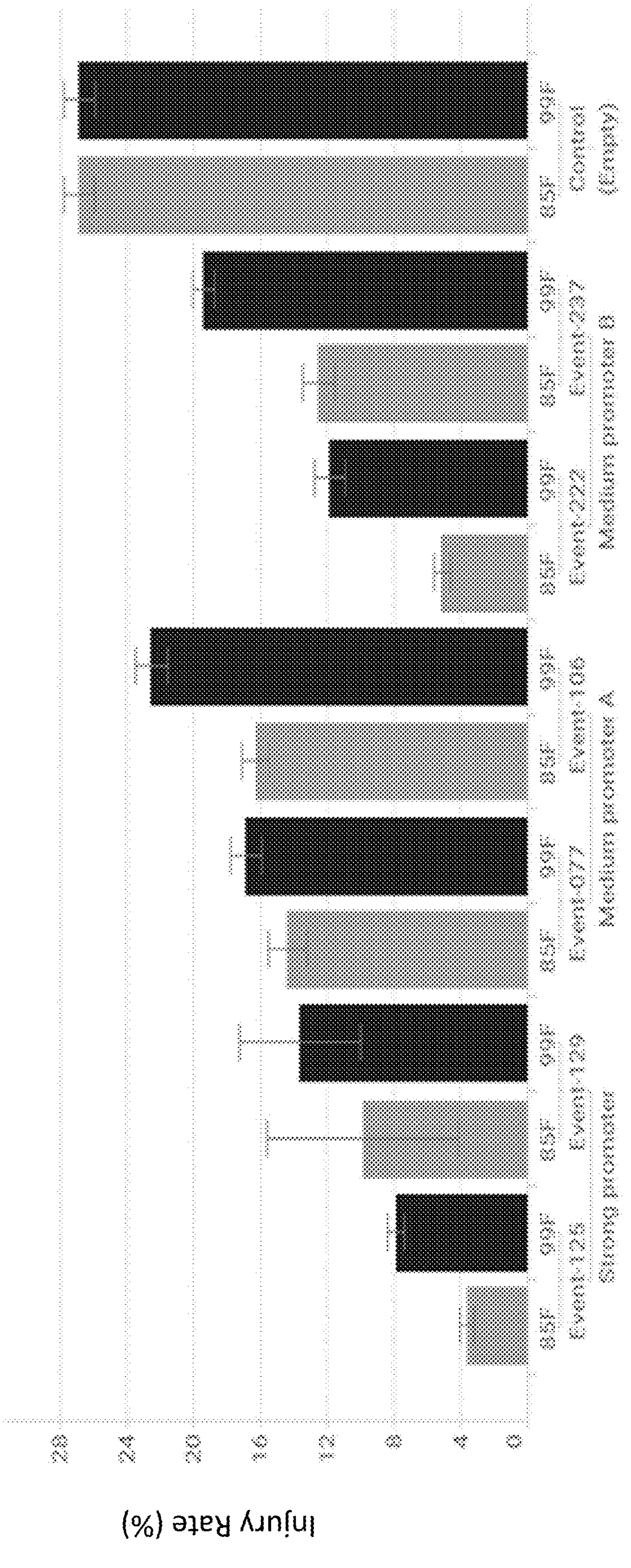
FIG. 4B shows the percent crop injury following mesotrione application. The gray bars represent mesotrione injury ratings at 85° F. and the black bars represent mesotrione injury ratings at 99° F. for these transgenic plants.

As shown in FIG. 4A, as the temperature increased from 85° F. to 99° F., there was a significant reduction in Os·TDO protein in the transgenic plants, regardless of the promoter used. However, plants with the strong constitutive promoter still produced/retained higher Os·TDO content compared to those with the medium constitutive promoters. The higher Os·TDO protein content with the strong constitutive promoter also translated into a reduction in plant injury at both normal (85° F.) and elevated (99° F.) plant growth temperatures (FIG. 4B).

Example 4: Improved Mesotrione Tolerance by Optimizing TDO Protein for Temperature Stabilization A rational design approach based on the ortholog analysis described above was taken to design a set of TDO variants that possess improved temperature stability along with the desired enzymatic activity. In the first round of variants screened, five variants passed high-throughput screens and were further characterized.

TABLE 3

Characterization of 1st round selected Os.TDO variants by in vitro biochemical assays.

| Construct | TDO Variant | % Identity to Os.TDO | # Amino Acid Changes Relative to Os.TDO | Heat Stability | Enzyme Activity ($K_{cat}/K_m$, $M^{-1}sec^{-1}$) | Polynucleotide SEQ ID NO | Polypeptide SEQ ID NO |
|---|---|---|---|---|---|---|---|
| 1 | Os.TDO | — | — | 39.5 | 7528 | 1 | 2 |
| 10 | D08 | 94.32 | 20 | 46 | 967 | 17 | 18 |
| 11 | B03 | 94.92 | 18 | 51 | 2167 | 19 | 20 |
| 12 | F09 | 94.33 | 20 | 53.5 | 316 | 21 | 22 |
| 13 | A04 | 93.75 | 22 | 46 | 138 | 23 | 24 |
| 14 | B09 | 93.75 | 22 | 49 | 18 | 25 | 26 |

Figure 5A:
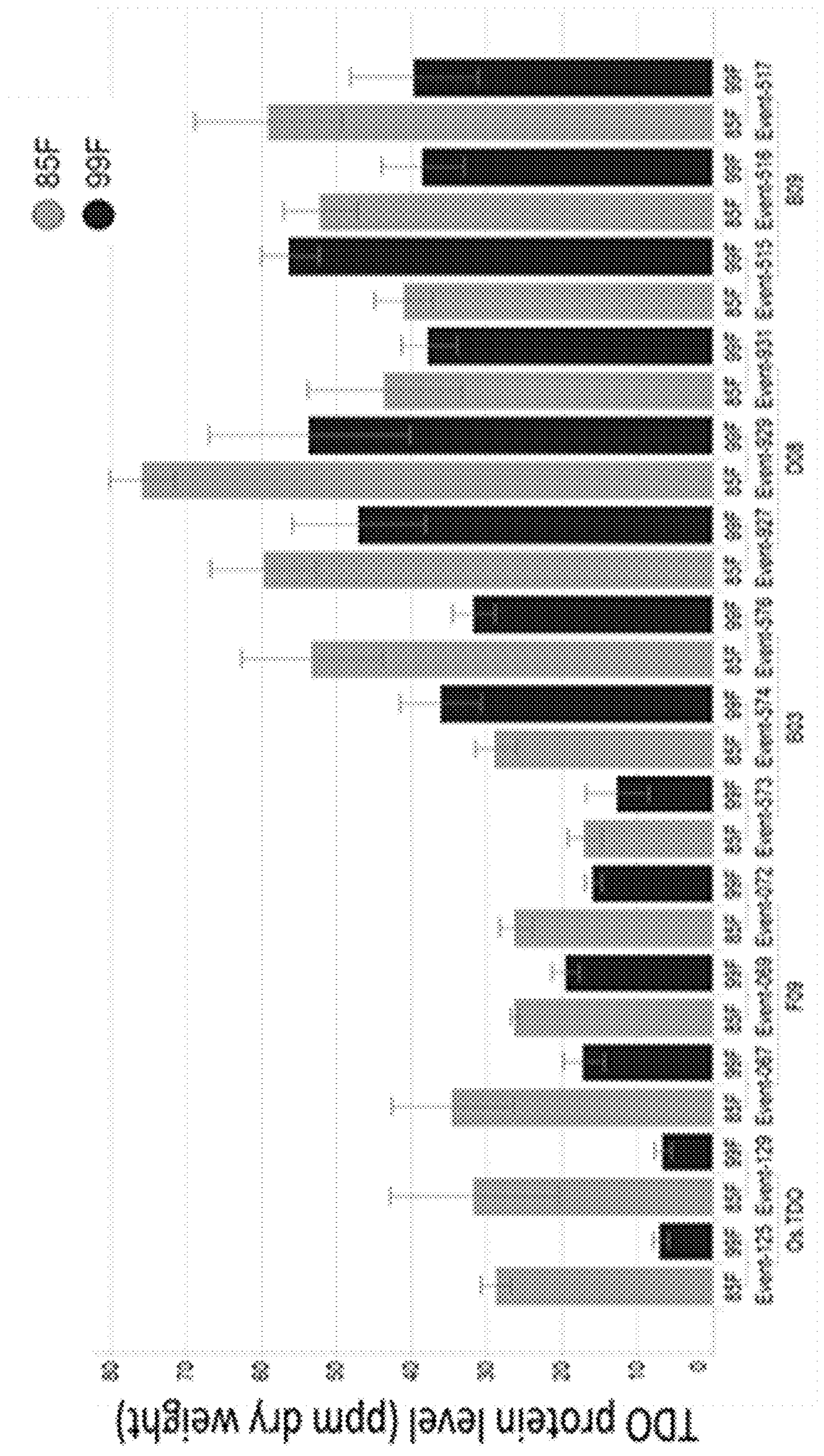
FIG. 5A and FIG. 5B: Shows protein content by ELISA and injury rate of transgenic soybean plants containing Os·TDO variants.
Figure 5B:
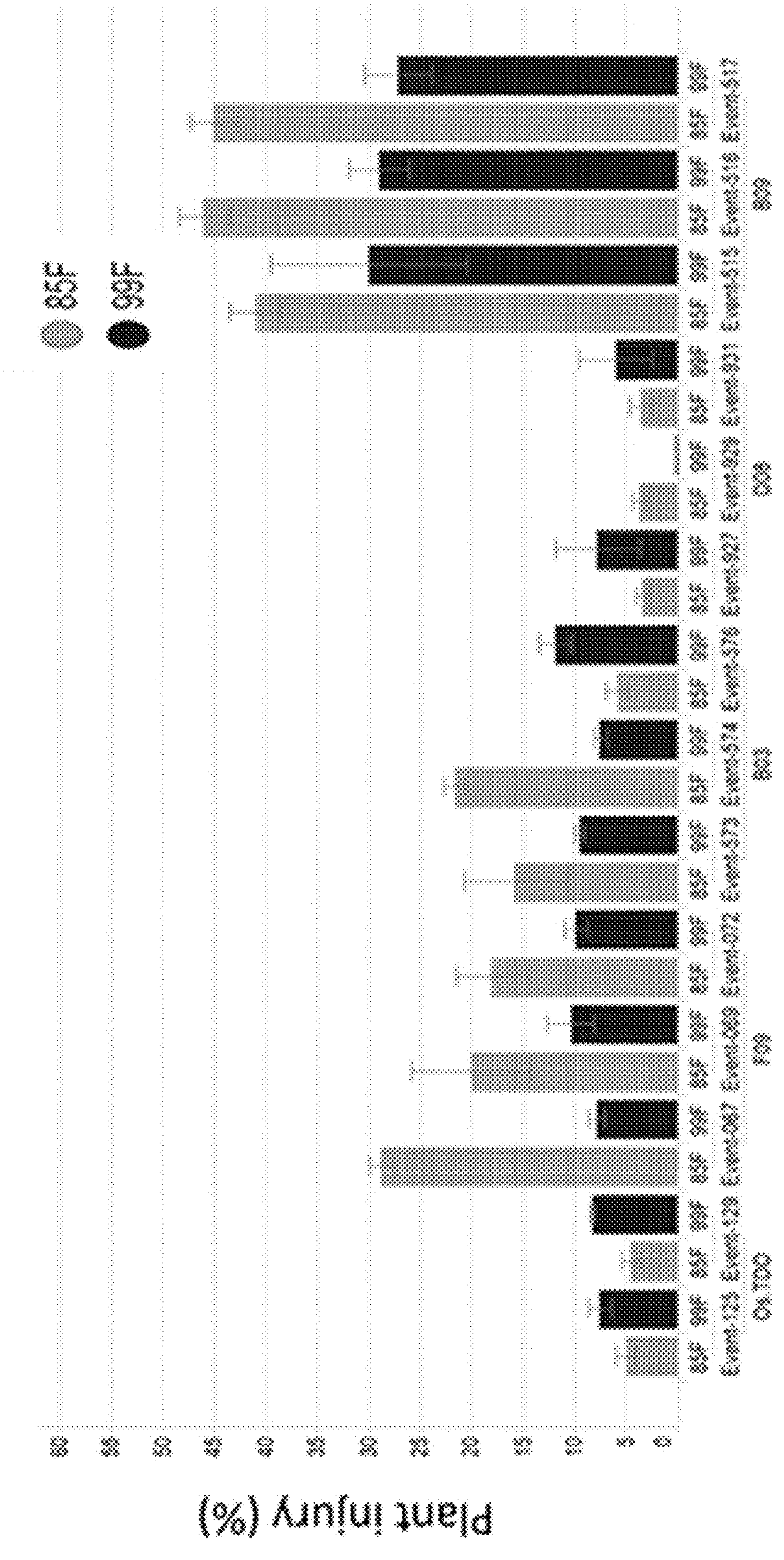

As shown in Table 3, all five variants showed heat stability that was better compared to Os·TDO, defined as the temperature at which 50% of the enzyme denatures. However, all five also showed reduced enzyme activity in vitro. The enzyme activity was measured at room temperature for the hydroxylation of mesotrione, and was defined as $K_{cat}/K_m$, $M^{-1}$ $sec^{-1}$ (specificity constant). Of these variants, four were tested in soybean plants. All of the variants tested in transgenic soybean plants either trended or showed significantly improved enzyme stability from leaf samples collected from plants grown at normal growth temperature (85° F.) and elevated temperature (99° F.) as shown by ELISA (FIG. 5A). However, when the transgenic soybean plants were assayed for tolerance to mesotrione application, 3 of the 4 variants showed injury ratings that trended or were often significantly higher than the Os·TDO control, especially at normal growth temperatures. Only one variant, referred to as D08 (Construct 10), had injury ratings that were similar to the Os·TDO control at normal temperatures, and a possibly trending lower injury relative to the Os·TDO control at elevated temperatures (FIG. 5B).

Additional testing of the best variant, D08, in a field setting confirmed that this variant provided good tolerance to mesotrione spray treatment, but was not significantly different from the control plants expressing Os·TDO driven by the strong constitutive promoter. Since this testing was conducted in the field, there was no control on the temperature ranges the plants were exposed to.

Based on these observations, an additional round of optimization focused on improving the enzyme activity while maintaining the improved temperature stability in order to further reduce herbicide injury in plants at both normal and higher temperatures to mesotrione applications. The variant D08 was used as the base variant for all Round 2 optimization. Rational design, which took into account the results from the Round 1 screens, was used in engineering Round 2 variants. Much of the rational design work focused on selected point amino acid changes in D08 (relative to wild-type) that were made in Round 1 that could be restored to wild-type amino acids (or similar) with the general approach being that the amino acid positions could be uncovered that were important for activity and those important for stability. The goal was to find amino acid positions that were independent of each other so that improvements could be made to both stability and activity without a negative impact on the opposing improvement target to build variants with improved characteristics for both objectives. As a general rule, improving an enzyme for either stability or activity often has an opposing effect on the other characteristic. For example, improving stability may result in an enzyme that is very resistant to denaturing at higher temperatures, but at the expense of reducing overall enzymatic activity. Effort was focused on improvements in both characteristics at the same time, which is often a much larger engineering challenge.

Figure 6:
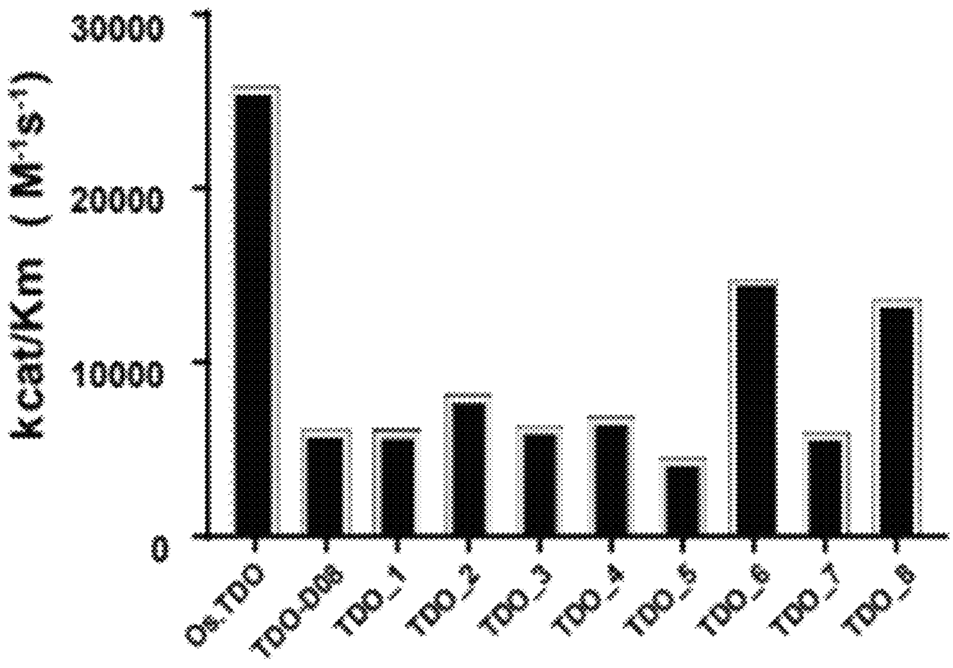
FIG. 6: Shows the comparison of enzyme activity at room temperature for Round 2 variants. The enzyme activity was expressed as $K_{cat}/K_m$, $M^{-1}$ $sec^{-1}$.

For the Round 2 optimization, approximately 300 variants were designed based on the D08 template, largely exploring various amino acid positions that could be returned to the wild-type amino acid. Of these, approximately 250 were successfully cloned and screened in a high-throughput screen, with a subset selected for more detailed characterization. Several rounds of enzymatic characterization were completed to select a final eight candidates that underwent detailed in vitro enzymatic characterization and were tested in plant assays as well. Of these eight candidates, all showed improved enzymatic stability relative to the Os·TDO starting point (data not shown). However, only two of the candidates (TDO_6 and TDO_8) had enzymatic activity that was significantly improved over the D08 variant, and none of the enzymes had enzymatic activity better than Os·TDO at room temperature (FIG. 6).

The next set of experiments was focused on determining if the balance between improved enzyme stability could outweigh a reduction in activity observed at optimal temperatures in soybean plants. Potentially the improved stability could enable more active enzyme to be available in the plant cell throughout a reasonable range of temperatures and thus tolerance is improved even if the activity is somewhat reduced for each enzyme. To test this hypothesis, the eight variants from Round 2 biochemical analysis described in the preceding paragraph were transformed into soybean through *Agrobacterium*-mediated transformation, along with three controls. One of the controls (TDO_9) was a variant from the high-throughput screens that had poor activity. Two other controls were the D08 variant and the Os·TDO. $R_0$ transgenic soybean plants were sprayed with the mesotrione herbicide to screen for herbicide tolerance. Due to some technical issues in the plant transformation process unrelated to the transgenes themselves, three of the variants did not produce any transgenic plants for testing. These included the Os·TDO control, the D08 variant and one Round 2 variant. The plants were scored for percent injury as described in the previous examples. All the variants showed low to mid 30% injury ratings, demonstrating tolerance in these plants relative to the wild-type transformation germplasm control, which averaged 45% injury (Table 4).

TABLE 4

Response of Soybean Plants Transformed with Round 2 TDO variants to mesotrione treatment.

| Variant Name | Construct | Mutations (Relative to D08) | % IDs to Os.TDO/D08 | $R_0$ % Injury | Polynucleotide SEQ ID NO | Polypeptide SEQ ID NO |
|---|---|---|---|---|---|---|
| Os.TDO | 9 | Control | 100/94.32 | ND | 1 | 2 |
| TDO-D08 | 15 | — | 94.32/100 | ND | 17 | 18 |
| TDO_1 | 16 | P35S-H116N | 94.9/99.1 | 30% | 27 | 28 |
| TDO_2 | 17 | P35S-E120Q | 94.9/99.1 | ND | 29 | 30 |
| TDO_3 | 18 | P35S-G242S | 94.9/99.1 | 35% | 31 | 32 |
| TDO_4 | 19 | H116N-G242S | 94.9/99.1 | 32% | 33 | 34 |
| TDO_5 | 20 | E120Q-G242S | 94.9/99.1 | 30% | 35 | 36 |
| TDO_6 | 21 | G242S-P256E | 94.9/99.1 | 31% | 37 | 38 |
| TDO_7 | 22 | G242S-S274C | 94.9/99.1 | 32% | 39 | 40 |
| TDO_8 | 23 | Q32K-I48L-V133I-G242S-P256E | 95.7/98.3 | 31% | 41 | 42 |
| TDO_9 | 24 | F199L-K279R | 94.9/99.1 | 36% | 43 | 44 |
| WT Control | | | | 45% | | |

As shown in Table 4, the wild-type (WT) control had the highest injury of the variants tested. While the Os·TDO control failed transformation in this experiment, a typical injury rating for $R_0$ soybean (using the same expression elements) would have been high 20% to low 30%. This suggests that the variants had similar injury to what would be expected for Os·TDO at optimal growth conditions. The results from the Round 2 variants provided insights on sites/amino acid changes that could help stabilize the TDO protein, especially for crops that may be exposed to hotter temperatures. In addition, these amino acid changes are candidates for gene editing of the native trait in rice or similar crops to improve the native trait, or to edit the transgene itself in crops such as soybean.

Cotton is a crop of interest that is often exposed to high temperature growing conditions and thus, selected TDO variants were tested in cotton. Three TDO variants, D08, TDO_6, and TDO_8 were transformed into cotton (along with the Os·TDO control) using similar expression elements in single-cassette vectors or as part of multi-cassette vectors. $R_2$ transgenic cotton plants were then screened for tolerance to mesotrione. Sixteen plants from two events each per construct were sprayed with two rates (2× and 8×) of mesotrione at V3 stage under normal (80° F.) and hot (100° F.) growing conditions. In addition, the effect of heat treatment on TDO accumulation in cotton plants were measured by ELISA. Cotton plants were planted and grown under normal greenhouse conditions (80° F. day/70° F. night) until V3 growth stage. Half of the plants were then moved to a higher temperature growth chamber (100° F. day/82° F. night) for the heat treatment, whereas the remaining half of the plants stayed in the same greenhouse (80° F. day/70° F. night). At day 3 after the plants were placed under different temperature conditions, leaf samples were collected for TDO protein measurement. The plants in 100° F. growth chamber and in 80° F. greenhouse were both sprayed with 2× mesotrione (210 g a.i./ha). Leaf samples were collected again 7 days after mesotrione treatment (DAT: Days After Treatment) for protein assay. Table 5 compares protein levels of the TDO variants in transgenic cotton plants grown under the two tested conditions. The protein levels for the TDO variants were measured at three time points for plants: 1) just before entering the high temperature treatment, 2) three days following placement into control (normal growth temperature) or high temperature (100° F.), and 3) 7 days after a 2× mesotrione spray.

TABLE 5

Effect of heat treatment on TDO protein accumulation in cotton plants.

| | | TDO Protein Level (ppm Dry Weight) | | | | | |
|---|---|---|---|---|---|---|---|
| | | Growth Temperature: 80° F. | | | Growth Temperature: 80° F. > 100° F. | | |
| Construct | TDO Variant | At V3 Stage (80° F.) | 3 Days Before Mesotrione Spray (80° F.) | 7 Days After Mesotrione Spray (80° F.) | At V3 Stage (80° F.) | 3 Days Before Mesotrione Spray (100° F.) | 7 Days After Mesotrione Spray (100° F.) |
| — | Wild-type Control | <0.75 | <0.75 | <0.75 | <0.75 | <0.75 | <0.75 |
| 30 | Os.TDO | 41 | 34 | 26.4 | 42.5 | 18.9 | 14.8 |
| 31 | Os.TDO | 55.4 | 50.9 | 41.5 | 59.3 | 27.5 | 24.9 |
| 27 | D08 | 65.1 | 67.5 | 49 | 62.2 | 59.8 | 49.6 |
| 25 | D08 | 93.3 | 89.1 | 75 | 85.8 | 92 | 89.7 |
| 28 | TDO_6 | 51 | 57.3 | 34.3 | 50.5 | 58.8 | 54.2 |
| 29 | TDO_8 | 53.3 | 55.5 | 45.4 | 55.2 | 60 | 48.9 |

In this experiment, the Os·TDO plants showed a reduction in TDO protein levels in the high temperature treatment relative to normal conditions at both the 3 and 7 days after treatment timepoints. However, all three optimized TDO variants showed no significant changes in TDO protein levels between the normal and hot growth conditions confirming excellent in planta heat stability of the enzyme. Table 6 shows the results of mesotrione treatment for cotton plants expressing these selected TDO variants. While all TDO expressing cotton events showed excellent tolerance, two of the variants, D08 and TDO_6, showed injury rates that were trending even lower than the Os·TDO controls at the higher temperature. This suggests that the enhanced heat stability of the enzyme translates to improved herbicide tolerance in cotton. In contrast, the wild-type control cotton plants showed high injury (poor tolerance) to all mesotrione applications.

TABLE 6

Results of mesotrione treatment for cotton plants expressing TDO variants.

| | | Crop Injury (%) | | | |
|---|---|---|---|---|---|
| | | Under 80° F. | | Under 100° F. | |
| Construct | TDO Variant | 210 g/ha (2X) Mesotrione | 840 g/ha (8X) Mesotrione | 210 g/ha (2X) Mesotrione | 840 g/ha (8X) Mesotrione |
| | Wild-type Control | 36.25 | 30 | 40 | 40 |
| 30 | Os.TDO | 0 | 0 | 1.71 | 0.75 |
| 31 | Os.TDO | 0 | 0 | 0.33 | 0.25 |
| 27 | D08 | 0 | 0 | 0 | 0 |
| 25 | D08 | 0 | 0 | 0 | 0 |
| 28 | TDO_6 | 0 | 0 | 0 | 0 |
| 29 | TDO_8 | 0.25 | 0 | 0.27 | 0 |

Example 5: Structural and Functional Characterization of Triketone Dioxygenase from *Oryza sativa*

Of the TDO genes tested from different species, the rice gene (Os·TDO) was unique in its ability to provide strong protection to plants to mesotrione. The only other TDO which provided protection, although at a much lower efficacy, was the maize TDO (Zm·TDO), as shown in Example 2. The amino acid sequences of various proteins having TDO activity and two closely related proteins, BRT and At·dioxy, were aligned to amino acid sequence of Os·TDO. 2BRT and At·dioxy are anthocyanidin synthases from *Arabidopsis thaliana*. Both are involved in anthocyanin and protoanthocyanidin biosynthesis by catalyzing the oxidation of leucoanthocyanidins into anthocyanidins.

Figure 7:
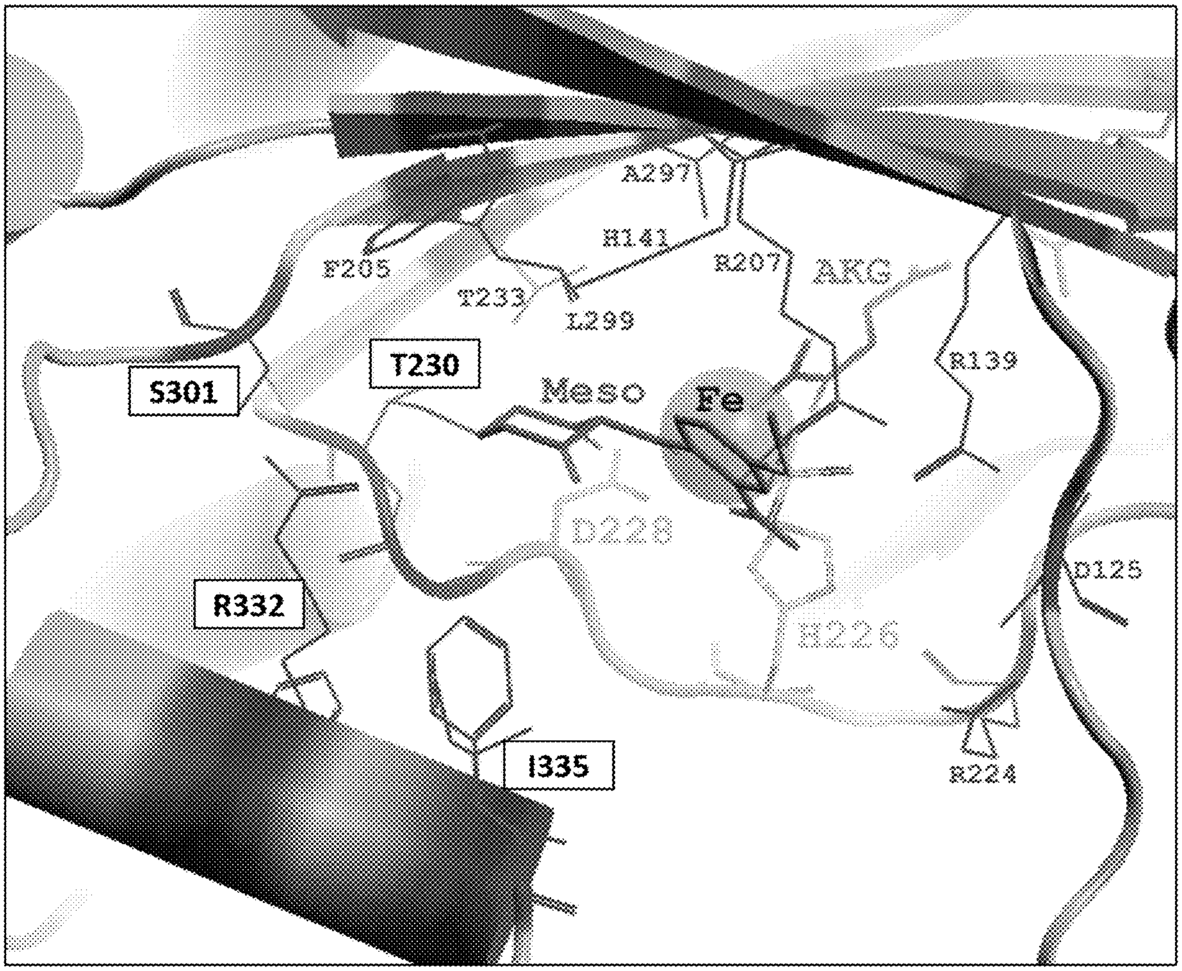
FIG. 7: Depicts the active site of TDO, showing the amino acid residues T230, S301, R332, and I335 of Os·TDO (in boxes) hypothesized to be activity determinants. The amino acid residues were modeled onto the structure of *Arabidopsis* anthocyanidin synthase (1GP5); all other amino acids shown are numbering from 1GP5. Mesotrione (marked as Meso) is shown in an expected conformation.

Based on this sequence alignment, the amino acids were divided into several categories, including those amino acids which were: 1) conserved throughout all of the proteins (indicated with open triangles in FIG. 10); 2) conserved throughout all the TDO-type proteins (indicated with solid triangles in FIG. 10); 3) near the binding site of mesotrione, and conserved among many TDO proteins (indicated with boxes with a dashed line in FIG. 10); 4) near the binding site of mesotrione, but found only in the rice TDO or rice and/or maize TDO as shown with boxes with a solid line in FIG. 10. Since the 2BRT protein differs from the At·dioxy protein only in that it lacks the N-terminal methionine, it is not shown in FIG. 10. From the latter category, four amino acids were identified: Thr230, Ser301, Arg332, and Ile335 of the rice TDO (FIG. 10). The first three of these (Thr230, Ser301, and Arg332) were found only in rice TDO; while the fourth, Ile335, was found in both rice and maize TDO. These four amino acids were mapped onto the structure of the rice TDO protein as shown in FIG. 7, and were hypothesized to play an important role in conferring tolerance to mesotrione.

To test the hypothesis, the four amino acids of sorghum TDO corresponding to amino acid positions 230, 301, 332, and 335 in rice TDO were replaced with those of rice TDO. The corn, rice, sorghum, and the modified sorghum TDO genes were cloned into a pET28 vector for *E. coli* expression with His6 tag in the N-terminus. Subsequently, the proteins were expressed and purified by affinity chromatography. BL21-CodonPlus (DE3)-RIPL *E. coli* cells (Stratagene) were used for expression. Cells transformed with expression vector were grown in autoinduction media (AIM) supplemented with 100 μg mL-1 kanamycin and 34 μg mL-1 chloramphenicol.

TDO proteins used in this study were expressed in AIM cells using an auto-induction system as described by Studier (2014). Briefly, the recombinant cultures were grown at 37° C. for 3 hours and then 20° C. for one or two days. Cells were harvested by centrifugation and frozen at −80° C. The pellet was resuspended in lysis buffer (Bper and Yper [Pierce] with ratio 3 to 1, 25 mM Tris-HCl, 300 mM NaCl, 10 mM imidazole, pH 8.0). 150 mM ferric ammonium citrate (1000×) was added to the lysate to a final concentration of 150 UM and incubated on ice for 20 minutes. The lysate was centrifuged to clarify the supernatant. Clear supernatant was loaded onto a 5 mL Ni column connected to AKTA Express (GE Healthcare). The column was washed with washing buffer (25 mM Tris-HCl, 300 mM NaCl, 30 mM imidazole, pH 8.0). The protein was eluted with 25 mM Tris-HCl, 300 mM NaCl, 150 mM imidazole, pH 8.0. The protein from the Ni column was concentrated and subjected to size-exclusion chromatography using a Superdex 200 column connected to AKTA Explorer (GE Healthcare) equilibrated with 25 mM Tris, 150 mM NaCl and 1 mM DTT, pH 8.0. Fractions containing pure TDO were pooled. All purification steps were carried out at 4° C. Protein concentrations were determined spectrophotometrically based on their calculated molar absorption extinction coefficients at 280 nm.

TDO activity was measured by the second hydroxylation of mesotrione. For routine activity measurements of TDO and determining the kinetic properties of the second hydroxylation, the continuous change in A330, which is specific to the second hydroxylation and subsequent non-enzymatic water removal (i.e. the conversion of hydroxy-mesotrione to oxy-mesotrione), was monitored. The reaction mixture (100 μL) contained 50 mM MOPS (pH 7.2), 2.5 mM oxoglutarate, 50 μM iron (II) sulfate heptahydrate, 150 mM KCl, 150 UM sodium ascorbate, 100 to 600 M mesotrione, and 50-250 nM TDO protein. The reaction proceeded until the maximum A330 was obtained (usually 20-120 minutes depending upon the concentration of mesotrione) and the linear portion of the curve was determined by visual inspection. Because the starting concentration of mesotrione was used as an estimate for the concentration of hydroxy-mesotrione, and less than 100% of mesotrione would have been converted by the beginning of the linear phase of the second reaction, the starting concentrations of hydroxy-mesotrione and therefore also the $K_m$ was always slightly underestimated.

For the activity calculation, aliquots of the reaction were removed at various time points during the reaction and heated at 95° C. to halt the reaction. The reaction mixtures were analyzed by HPLC and mass spectrophotometry. By product conversation followed by peak integration on HPLC, a linear plot was obtained and the extinction coefficient delta between the substrate (mesotrione) and the second product (oxy-mesotrione) was obtained according to the equation $\Delta A330=(\varepsilon_p-\varepsilon_s)*b\Delta p$ where ΔA330 is the change of absorbance at 330 nm and b is the light path.

Figure 8:
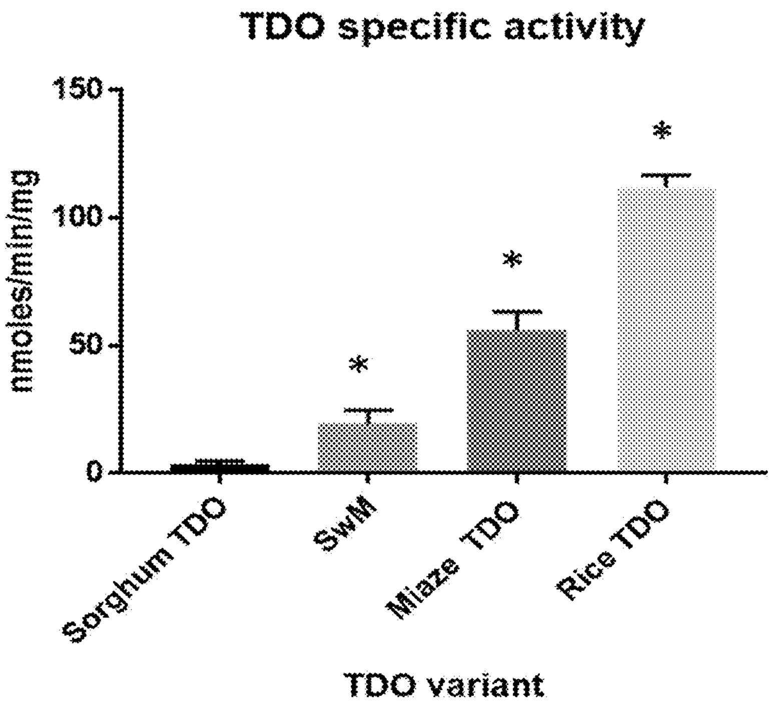
FIG. 8: Shows the activity of TDO proteins from rice, maize, sorghum, and the sorghum variant (SwM) containing the four amino acid substitutions (P230T, A301S, L332R, V335I) corresponding to rice TDO at the corresponding positions. Activity was expressed as nmol/min/mg protein and was the mean of three separate assays on the same enzyme sample (technical reps). Asterisks indicate that the activity was significantly different than the blank ($p<0.05$).

The specific activity of the TDO variants of the second hydroxylation is shown in FIG. 8. In agreement with the plant data, rice TDO (Os·TDO) had the highest activity, followed by corn TDO which had about 30% lower activity than rice TDO. Sorghum TDO was not significantly different from the blank, whereas the sorghum TDO variant designated as SwM had about 17% activity compared to the rice TDO protein. The SwM variant comprises the combination of substitutions P230T-A301S-L332R-V335I, in which the wild-type sorghum residues at positions 230, 310, 332, and 335 were replaced with those from rice TDO.

Figure 9A:
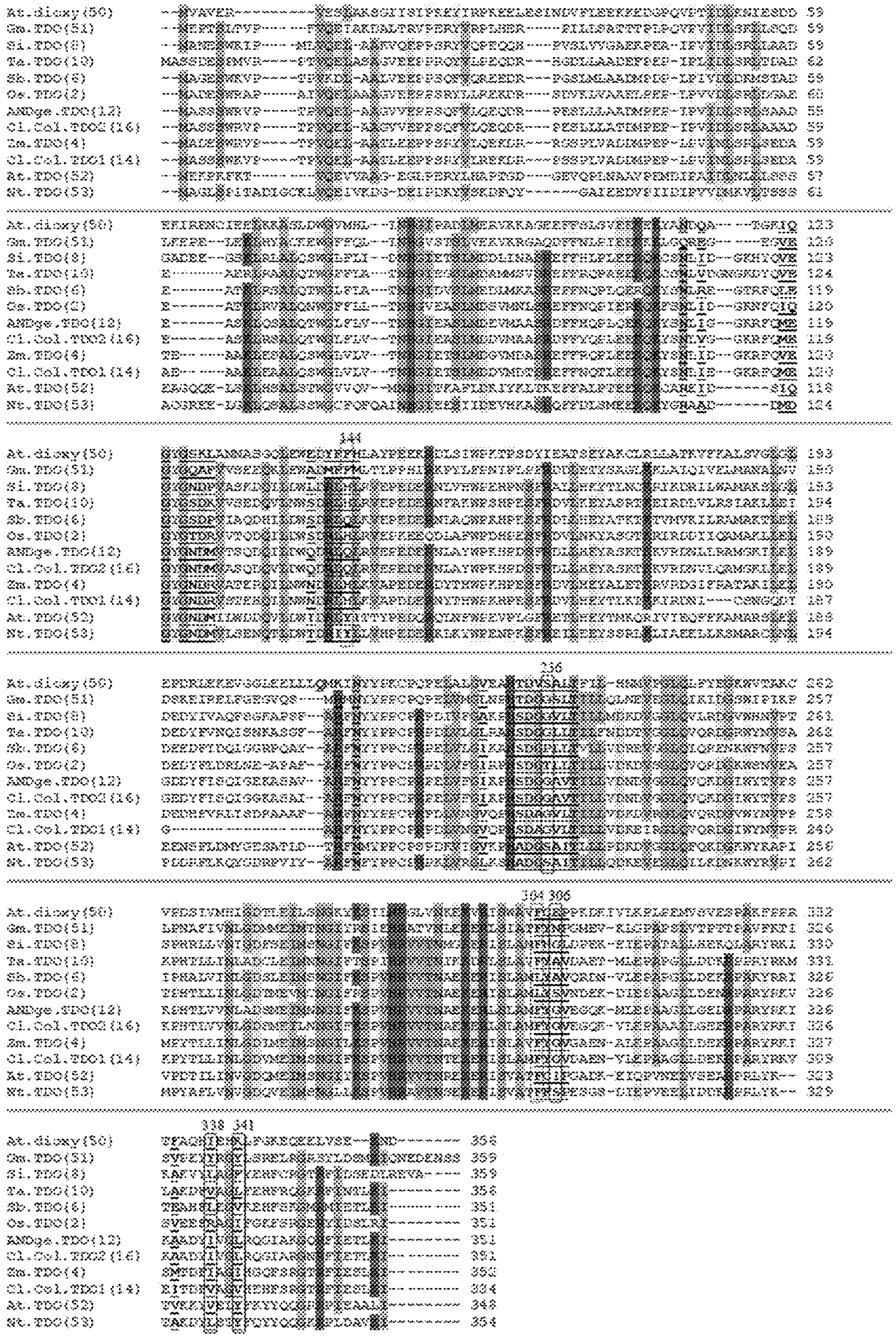
FIG. 9A, FIG. 9B, FIG. 9C, and FIG. 9D: Shows a phylogenetic analysis of the active site of TDO-like proteins.
Figure 9B:
Figure 9C:
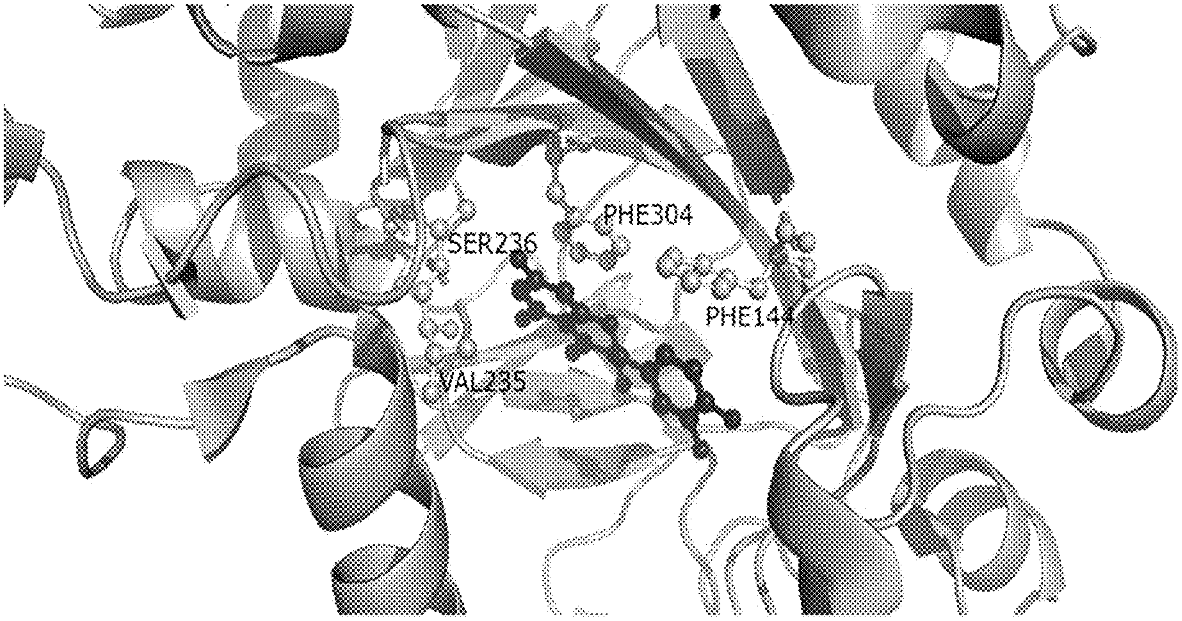
Figure 9D:
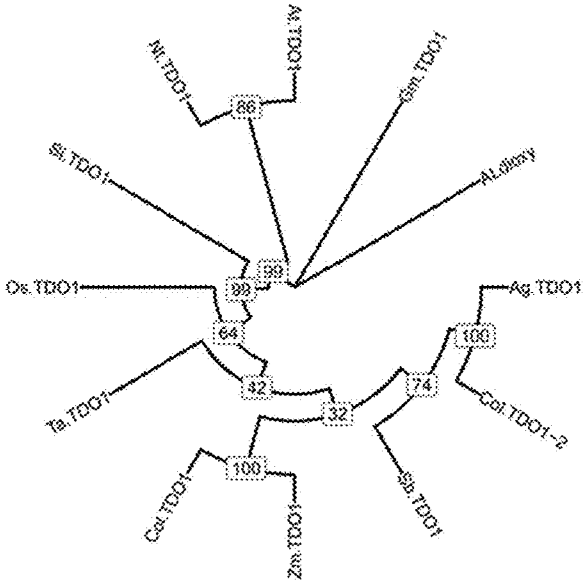

In addition to the full-length alignment of TDO proteins, the amino acid sequences adjacent to the active sites from TDO homologues were aligned (FIG. 9A) and overlaid with the 1GP5 structure of anthocyanidin synthase (ANS) which is complexed with one of its substrates, DQH (trans-dihydroquercetin). The pi stacking between the enzyme and compound may be important to hold the compound in the active site. DQH pi stacks with $Phe^{144}$ in 1GP5 (FIGS. 9B and 9C), and mapping this to TDO suggests that mesotrione may have some pi stacking with the $His^{141}$ at that position in Os·TDO (alignment in FIG. 9A). In this regard, it is interesting to note that monocots that have a glutamine at the position corresponding to position 144 of 1GP5 are not active. Expanding on this, other amino acids, such as Tyr at the corresponding position ($Phe^{141}$ in Gm·TDO; $His^{141}$ in Zm·TDO) may yield an enhancement to activity due to the aromatic nature of the amino acid and potential pi stacking (FIG. 9A).

On the left side of the binding pocket ($Ser^{236}$ 1GP5), dicots have more rigidity in this area. Proteins that contain two glycine residues in this region may allow enough flexibility in the binding pocket for the reaction to occur whereas proteins that have no glycine may not have enough flexibility.

Both active monocot TDO proteins have one glycine and a residue with few degrees of backbone freedom. Therefore, glycine could be substituted for serine at the corresponding to position 236 in 1GP5 (see FIG. 9A; $Thr^{230}$ in Os·TDO; $Gly^{230}$ in Gm·TDO; $Gly^{231}$ in Zm·TDO), along with a hydrophobic residue (A, L, V, I, T, S) at the position corresponding to 235 in 1GP5 (see FIG. 9A; $Gly^{229}$ in Os·TDO; $Gly^{229}$ in Gm·TDO; $Ala^{230}$ in Zm·TDO). Further, the position corresponding to $Val^{235}$ in 1GP5 (FIG. 9A; $Gly^{229}$ in Os·TDO; $Gly^{229}$ in Gm·TDO; $Ala^{230}$ in Zm·TDO) could be changed to glycine if the equivalent of $Ser^{236}$ of 1GP5 was changed to threonine, alanine, leucine, valine, isoleucine, or serine.

Furthermore, a leucine, alanine, valine, or isoleucine at position 299 in Os·TDO (corresponding to position F304 in 1GP5) may allow more space for the non-aromatic ring of mesotrione to bind. In the case of DQH, there is pi stacking between the Phe and DQH. This is present among dicots such as soy (Gm·TDO F299). It also may explain reduced activity in corn TDO ($Phe^{300}$ in Zm·TDO) compared to rice TDO. However, surveying other TDOs based on their similarity to the active site of rice TDO, rather than the similarity of the entire protein, may provide a valid strategy to identify naturally active or other variants.

The invention claimed is:

1. A recombinant DNA molecule comprising a nucleic acid sequence encoding a protein having triketone dioxygenase (TDO) activity, wherein the protein has at least 93% sequence identity to an amino acid sequence selected from the group consisting of SEQ ID NOs: 2, 4, 6, 8, 10, 12, 14, and 16, wherein the protein comprises at least one amino acid substitution as compared to SEQ ID NO: 2, 4, 6, 8, 10, 12, 14, or 16, and wherein the protein comprises:

a threonine (T), alanine (A), leucine (L), valine (V), isoleucine (I), serine(S), or glycine (G) at the position corresponding to position 230 of SEQ ID NO: 2;

a serine(S) at the position corresponding to position 301 of SEQ ID NO: 2;

an arginine (R) at the position corresponding to position 332 of SEQ ID NO: 2;

an isoleucine (I) at the position corresponding to position 335 of SEQ ID NO: 2;

a tyrosine (Y), phenylalanine (F), or histidine (H) at the position corresponding to position 141 of SEQ ID NO: 2;

an alanine (A), isoleucine (I), leucine (L), serine(S), threonine (T), valine (V), or glycine (G) at the position corresponding to position 229 of SEQ ID NO: 2;

an alanine (A), isoleucine (I), leucine (L), or valine (V), at the position corresponding to position 299 of SEQ ID NO: 2; or a combination of any thereof;

provided that: (i) when a threonine (T), alanine (A), leucine (L), valine (V), isoleucine (I), or serine(S) is present at the position corresponding to position 230 of SEQ ID NO: 2, a glycine (G) is present at the position corresponding to position 229 of SEQ ID NO: 2; and (ii) when an alanine (A), leucine (L), valine (V), isoleucine (I), threonine (T), or serine(S) is present at the position corresponding to position 229 of SEQ ID NO: 2, a glycine (G) is present at the position corresponding to position 230 of SEQ ID NO: 2.

2. The recombinant DNA molecule of claim 1, wherein the protein has at least 93% sequence identity to an amino acid sequence selected from the group consisting of SEQ ID NOs: 4, 6, 8, 10, 12, 14, and 16 and wherein the protein comprises:

a threonine (T) at the position corresponding to position 230 of SEQ ID NO: 2;

a serine(S) at the position corresponding to position 301 of SEQ ID NO: 2;

an arginine (R) at the position corresponding to position 332 of SEQ ID NO: 2;

an isoleucine (I) at the position corresponding to position 335 of SEQ ID NO: 2; or a combination of any thereof.

3. The recombinant DNA molecule of claim 2, wherein the protein comprises:

a threonine (T) at the position corresponding to position 230 of SEQ ID NO: 2;

a serine(S) at the position corresponding to position 301 of SEQ ID NO: 2;

an arginine (R) at the position corresponding to position 332 of SEQ ID NO: 2; and an isoleucine (I) at the position corresponding to position 335 of SEQ ID NO: 2.

4. The recombinant DNA molecule of claim 1, wherein the protein has:

a) at least 93% sequence identity to SEQ ID NO: 2 and comprises one or more amino acid substitutions selected from the group consisting of H141F, H141Y, G229A, G229I, G229L, G229S, G229T, G229V, T230A, T230G, T230I, T230L, T230S, T230V, L299A, L299I, L299V, and combinations of any thereof;

b) at least 93% sequence identity to SEQ ID NO: 4 and comprises one or more amino acid substitutions selected from the group consisting of H141F, H141Y, A230G, A230I, A230L, A230S, A230T, A230V, G231A, G231I, G231L, G231S, G231T, G231V, F300A, F300I, F300L, F300V, G302S, I333R, and combinations of any thereof;

c) at least 93% sequence identity to SEQ ID NO: 6 and comprises one or more amino acid substitutions selected from the group consisting of Q140F, Q140H, Q140Y, G229A, G229I, G229L, G229S, G229T, G229V, P230A, P230G, P230I, P230L, P230S, P230T, P230V, L299A, L299I, L299V, A301S, L332R, V335I, and combinations of any thereof;

d) at least 93% sequence identity to SEQ ID NO: 8 and comprises one or more amino acid substitutions selected from the group consisting of H144F, H144Y, G233A, G233I, G233L, G233S, G233T, G233V, G234A, G234I, G234L, G234S, G234T, G234V, F303A, F303I, F303L, F303V, G305S, L336R, F339I, and combinations of any thereof;

e) at least 93% sequence identity to SEQ ID NO: 10 and comprises one or more amino acid substitutions selected from the group consisting of H145F, H145Y, G234A, G234I, G234L, G234S, G234T, G234V, G235A, G235I, G235L, G235S, G235T, G235V, F304A, F304I, F304L, F304V, A306S, V337R, L340I, and combinations of any thereof;

f) at least 93% sequence identity to SEQ ID NO: 12 and comprises one or more amino acid substitutions selected from the group consisting of Q140F, Q140H, Q140Y, G229A, G229I, G229L, G229S, G229T, G229V, F299A, F299I, F299L, F299V, G230A, G230I, G230L, G230S, G230T, G230V, G301S, 1332R, L335I, and combinations of any thereof;

g) at least 93% sequence identity to SEQ ID NO: 14 and comprises one or more amino acid substitutions selected from the group consisting of H141F, H141Y, A212G, A212I, A212L, A212S, A212T, A212V, G213A, G213I, G213L, G213S, G213T, G213V, F282A, F282I, F282L, F282V, G284S, V315R, V318I, and combinations of any thereof; or h) at least 93% sequence identity to SEQ ID NO: 16 and comprises one or more amino acid substitutions selected from the group consisting of Q140F, Q140H, Q140Y, G229A, G229I, G229L, G229S, G229T, G229V, F299A, F299I, F299L, F299V, G230A, G230I, G230L, G230S, G230T, G230V, G301S, 1332R, L335R, and combinations of any thereof.

5. The recombinant DNA molecule of claim 4, wherein the protein having at least 93% sequence identity to SEQ ID NO: 4 comprises one or more amino acid substitutions selected from the group consisting of G231T, G302S, 1333R, and combinations of any thereof.

6. The recombinant DNA molecule of claim 4, wherein the protein having at least 93% sequence identity to SEQ ID NO: 4 further comprises an isoleucine (I) at position 336 of SEQ ID NO: 4.

7. The recombinant DNA molecule of claim 4, wherein the protein having at least 93% sequence identity to SEQ ID NO: 6 comprises one or more amino acid substitutions selected from the group consisting of P230T, A301S, L332R, V335I, and combinations of any thereof.

8. The recombinant DNA molecule of claim 4, wherein the protein having at least 93% sequence identity to SEQ ID NO: 8 comprises one or more amino acid substitutions selected from the group consisting of G234T, G305S, L336R, F339I, and combinations of any thereof.

9. The recombinant DNA molecule of claim 4, wherein the protein having at least 93% sequence identity to SEQ ID NO: 10 comprises one or more amino acid substitutions selected from the group consisting of G235T, A306S, V337R, L340I, and combinations of any thereof.

10. The recombinant DNA molecule of claim 4, wherein the protein having at least 93% sequence identity to SEQ ID NO: 12 comprises one or more amino acid substitutions selected from the group consisting of G230T, G301S, 1332R, L335I, and combinations of any thereof.

11. The recombinant DNA molecule of claim 4, wherein the protein having at least 93% sequence identity to SEQ ID NO: 14 comprises one or more amino acid substitutions selected from the group consisting of G213T, G284S, V315R, V318I, and combinations of any thereof.

12. The recombinant DNA molecule of claim 4, wherein the protein having at least 93% sequence identity to SEQ ID NO: 16 comprises one or more amino acid substitutions selected from the group consisting of G230T, G310S, 1332R, L335R, and combinations of any thereof.

13. The recombinant DNA molecule of claim 1, wherein the protein comprises SEQ ID NO: 48.

14. The recombinant DNA molecule of claim 1, wherein the protein further comprises:

a leucine (L) at the position corresponding to position 11 of SEQ ID NO: 2;

a lysine (K) at the position corresponding to position 18 of SEQ ID NO: 2;

a glutamine (Q) at the position corresponding to position 32 of SEQ ID NO: 2;

a proline (P) at the position corresponding to position 35 of SEQ ID NO: 2;

an isoleucine (I) at the position corresponding to position 48 of SEQ ID NO: 2;

a glycine (G) at the position corresponding to position 54 of SEQ ID NO: 2;

an isoleucine (I) at the position corresponding to position 82 of SEQ ID NO: 2;

an aspartic acid (D) at the position corresponding to position 89 of SEQ ID NO: 2;
a histidine (H) at the position corresponding to position 116 of SEQ ID NO: 2;
a glutamic acid (E) at the position corresponding to position 120 of SEQ ID NO: 2;
a valine (V) at the position corresponding to position 133 of SEQ ID NO: 2;
a histidine (H) at the position corresponding to position 167 of SEQ ID NO: 2;
a cysteine (C) at the position corresponding to position 173 of SEQ ID NO: 2;
a phenylalanine (F) at the position corresponding to position 199 of SEQ ID NO: 2;
a threonine (T) at the position corresponding to position 204 of SEQ ID NO: 2;
a glycine (G) at the position corresponding to position 230 of SEQ ID NO: 2;
a glycine (G) at the position corresponding to position 242 of SEQ ID NO: 2;
a proline (P) at the position corresponding to position 256 of SEQ ID NO: 2;
a serine(S) at the position corresponding to position 274 of SEQ ID NO: 2;
a lysine (K) at the position corresponding to position 279 of SEQ ID NO: 2; or
a combination of any thereof.

15. A recombinant DNA molecule comprising a nucleic acid sequence encoding a protein having triketone dioxygenase (TDO) activity, wherein the protein has at least 93% identity to SEQ ID NO: 2 and comprises one or more amino acid substitutions selected from the group consisting of I11L, A18K, K32Q, S35P, L48I, S54G, V82I, S89D, N116H, Q120E, I133V, N167H, T173C, L199F, A204T, T230G, S242G, E256P, C274S, R279K, and combinations of any thereof.

16. The recombinant DNA molecule of claim 15, wherein the protein comprises a) I11L, A18K, K32Q, S35P, L48I, S54G, V82I, S89D, N116H, Q120E, I133V, N167H, T173C, L199F, A204T, T230G, S242G, E256P, C274S, and R279K amino acid substitutions;
b) I11L, A18K, K32Q, L48I, S54G, V82I, S89D, Q120E, 1133V, N167H, T173C, L199F, A204T, T230G, S242G, E256P, C274S, and R279K amino acid substitutions;
c) I11L, A18K, K32Q, L48I, S54G, V82I, S89D, N116H, 1133V, N167H, T173C, L199F, A204T, T230G, S242G, E256P, C274S, and R279K amino acid substitutions;
d) I11L, A18K, K32Q, L48I, S54G, V82I, S89D, N116H, Q120E, 1133V, N167H, T173C, L199F, A204T, T230G, E256P, C274S, and R279K amino acid substitutions;
e) I11L, A18K, K32Q, S35P, L48I, S54G, V82I, S89D, Q120E, I133V, N167H, T173C, L199F, A204T, T230G, E256P, C274S, and R279K amino acid substitutions;
f) I11L, A18K, K32Q, S35P, L48I, S54G, V82I, S89D, N116H, 1133V, N167H, T173C, L199F, A204T, T230G, E256P, C274S, and R279K amino acid substitutions;
g) I11L, A18K, K32Q, S35P, L48I, S54G, V82I, S89D, N116H, Q120E, I133V, N167H, T173C, L199F, A204T, T230G, C274S, and R279K amino acid substitutions;
h) I11L, A18K, K32Q, S35P, L48I, S54G, V82I, S89D, N116H, Q120E, 1133V, N167H, T173C, L199F, A204T, T230G, E256P, and R279K amino acid substitutions;
i) I11L, A18K, S35P, S54G, V82I, S89D, N116H, Q120E, N167H, T173C, L199F, A204T, T230G, C274S, and R279K amino acid substitutions; or
j) I11L, A18K, K32Q, S35P, L48I, S54G, V82I, S89D, N116H, Q120E, 1133V, N167H, T173C, A204T, T230G, S242G, E256P, and C274S amino acid substitutions.

17. The recombinant DNA molecule of claim 15, wherein the protein further comprises:

a threonine (T) at the position corresponding to position 230 of SEQ ID NO: 2;
a serine(S) at the position corresponding to position 301 of SEQ ID NO: 2;
an arginine (R) at the position corresponding to position 332 of SEQ ID NO: 2; and
an isoleucine (I) at the position corresponding to position 335 of SEQ ID NO: 2.

18. The recombinant DNA molecule of claim 15, wherein the protein comprises SEQ ID NO: 18, 28, 30, 32, 34, 36, 38, 40, 42, or 44.

19. A recombinant DNA molecule comprising a nucleic acid sequence encoding a protein having triketone dioxygenase (TDO) activity, wherein the nucleic acid sequence comprises SEQ ID NO: 1.

20. The recombinant DNA molecule of claim 1, wherein the DNA molecule further comprises a heterologous promoter operably linked to the nucleic acid sequence encoding a protein having triketone dioxygenase (TDO) activity.

21. The recombinant DNA molecule of claim 20, wherein the heterologous promoter:

a) comprises a constitutive promoter; and/or
b) is functional in a plant cell.

22. The recombinant DNA molecule of claim 1, wherein the recombinant DNA molecule is comprised within a genome of a plant cell.

23. A DNA construct comprising the recombinant DNA molecule of claim 1.

24. An engineered protein encoded by the recombinant DNA molecule of claim 1.

25. A transgenic plant, plant seed, plant cell, or plant part comprising the recombinant DNA molecule of claim 1.

26. The transgenic plant, plant seed, plant cell, or plant part of claim 25, wherein the transgenic plant, plant seed, plant cell, or plant part is tolerant to at least one 4-hydroxyphenylpyruvate dioxygenase (HPPD) inhibitor herbicide.

27. The transgenic plant, plant seed, plant cell, or plant part of claim 26, wherein the HPPD inhibitor herbicide is selected from the group consisting of mesotrione, benzobicyclon (BBC), tembotrione, sulcotrione, tefuryltrione, 2-(2-nitro-4-trifluoromethylbenzoyl)cyclohexane-1,3-dione (NTBC), pyrazolate, benzofenap, pyrazoxyfen, isoxaflutole, pyrazolynate, topramezone, and combinations of any thereof.

28. The transgenic plant, plant seed, plant cell, or plant part of claim 25, wherein the transgenic plant, plant seed, plant cell, or plant part is tolerant to at least a second herbicide.

29. The transgenic plant, plant seed, plant cell, or plant part of claim 28, wherein the second herbicide is selected from the group consisting of an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor.

30. The transgenic plant, plant seed, plant cell, or plant part of claim 29, wherein the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

31. A commodity product comprising the recombinant DNA molecule of claim 1.

32. A method for conferring HPPD inhibitor herbicide tolerance to a plant, plant seed, plant cell, or plant part, comprising heterologously expressing the engineered protein of claim 24 in the plant, plant seed, plant cell, or plant part.

33. A method for producing an herbicide tolerant plant, comprising:

(a) transforming a plant cell with the recombinant DNA molecule of any one of claims 1-4; and (b) regenerating a plant from the plant cell that comprises the recombinant DNA molecule.

34. The method of claim 33, further comprising selecting the plant or a progeny thereof for HPPD inhibitor tolerance.

35. The method of claim 33, further comprising the step of crossing the regenerated plant with itself or with a second plant to produce progeny.

36. A method for controlling or preventing weed growth in a plant growth area, comprising applying an effective amount of at least one HPPD inhibitor herbicide to a plant growth area that comprises the transgenic plant or seed of claim 25, wherein the transgenic plant or seed is tolerant to the HPPD inhibitor herbicide.

37. A method of screening for a herbicide tolerance gene comprising:

(a) expressing the recombinant DNA molecule of claim 1 in a plant cell; and (b) identifying a plant cell that displays tolerance to an HPPD inhibitor herbicide.

38. A method of producing a plant tolerant to an HPPD inhibitor herbicide and at least one other herbicide comprising:

(a) crossing a plant of claim 25 with a second plant comprising tolerance to the at least one other herbicide, and (b) selecting a progeny plant resulting from said crossing that comprises tolerance to an HPPD inhibitor herbicide and the at least one other herbicide.

39. A method for reducing the development of herbicide-tolerant weeds comprising:

(a) cultivating in a crop growing environment a plant according to claim 25; and (b) applying an HPPD inhibitor herbicide and at least one other herbicide to the crop growing environment, wherein the crop plant is tolerant to the HPPD inhibitor herbicide and the at least one other herbicide.

* * * * *

SEQUENCE LISTING

```
Sequence total quantity: 54
SEQ ID NO: 1            moltype = DNA  length = 1056
FEATURE                 Location/Qualifiers
source                  1..1056
                        mol_type = other DNA
                        note = codon optimized for plant
                        organism = synthetic construct
SEQUENCE: 1
atggctgacg agtcatggag ggcgccggcg atagtgcaag agctggcggc agccggcgtc  60
gaggagccgc cgagccgata cctgctacgg gagaaagacc gttctgacgt caagctggtc  120
gccgccgagc tgccggagcc tctcccagtc gttgatctca gccggctaga tggtgccgag  180
gaggccacca agctcagggt ggctctgcag aattggggct tcttcctgct taccaaccat  240
ggagtagaag cctctctgat ggacagcgtg atgaacttgt cgagagagtt cttcaaccag  300
ccaatcgaac ggaagcagaa attcagcaac ttgatcgatg gcaagaactt ccagattcaa  360
gggtatggaa ctgaccgggt ggttacccaa gatcagatcc tggactggtc tgatcggttg  420
catctcagag ttgaacccaa ggaggagcaa gatcttgcct tctggcctga ccatcctgaa  480
tctttcaggg atgttctgaa caagtatgca tcaggaacta aaagaattag agacgatatc  540
attcaggcta tggccaagct tcttgagctt gatgaggatt acttcttgga ccgactcaac  600
gaagctcctg cattcgcaag attcaactac taccctccct gtccaaggcc tgaccttgtg  660
ttcggcatca ggcctcactc cgacggcacc ctcttgacga ttcttctcgt cgacaaagat  720
gtcagtggcc tgcaagttca gagggatggc aagtggtcca acgttgaggc aactcctcac  780
acattgctga tcaacttagg tgacaccatg gaggtaatgt gcaatggcat cttcaggagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                             1056

SEQ ID NO: 2            moltype = AA  length = 351
FEATURE                 Location/Qualifiers
source                  1..351
                        mol_type = protein
                        organism = Oryza sativa
SEQUENCE: 2
MADESWRAPA IVQELAAAGV EEPPSRYLLR EKDRSDVKLV AAELPEPLPV VDLSRLDGAE  60
EATKLRVALQ NWGFFLLTNH GVEASLMDSV MNLSREFFNQ PIERKQKFSN LIDGKNFQIQ  120
GYGTDRVVTQ DQILDWSDRL HLRVEPKEEQ DLAFWPDHPE SFRDVLNKYA SGTKRIRDDI  180
IQAMAKLLEL DEDYFLDRLN EAPAFARFNY YPPCPRPDLV FGIRPHSDGT LLTILLVDKD  240
VSGLQVQRDG KWSNVEATPH TLLINLGDTM EVMCNGIFRS PVHRVVTNAE KERISLAMLY  300
SVNDEKDIEP AAGLLDENRP ARYRKVSVEE FRAGIFGKFS RGERYIDSLR I           351

SEQ ID NO: 3            moltype = DNA  length = 1059
FEATURE                 Location/Qualifiers
source                  1..1059
                        mol_type = other DNA
                        note = codon optimized for plant
                        organism = synthetic construct
SEQUENCE: 3
atggctgacg agtcatggcg cgtcccgact cccgtacagg aactcgctgc taccctagag  60
gagccgccaa gccgttacgt ccttcaagaa aaggaccgac gtggatctcc gttggtggcc  120
gacgacatgc ctgagccgct tccggtcatt aacctttcaa ggttatcgga ggacgcaacc  180
gaggccgcta aattggagtc cgctctacaa tcttggggtc tggtgctcgt tactaaccac  240
gggatagaga cttcgttaat ggatggagtg atggatgcga gccgtgagtt cttcagacag  300
ccattggagg agaagcagaa gtacagcaac ttgatcgacg gaaagcggtt ccaagtggaa  360
ggctacggga acgaccgggt tgccacagag cgacaaattc tgaattggaa cgaccgtttg  420
cacctaaagg tcgcaccaga ggacgaaagg gactacactc actggcccaa gcacccggag  480
tccttccgtg acgttctaca cgaatacgct ttggaaacta agagggtgcg ggacgggatc  540
ttccgtgcta ctgctaagat cctagagcta gacgaggatc acttcgtaag gctaatctcc  600
gatagagctg ctgcattcgc ccgattcaat tactatccac cctgcccacg gccggaccta  660
```

```
gtgaacggtg ttcaaccgca ttccgacgct ggtgttctca ctatccttct ggtcgataag  720
gatgtccgtg ggcttcaagt tcagcgggac ggcgtctggt acaatgtgcc acccatgcca  780
tacacgctct tgattaacct gggtgacatc atggagataa tgtccaacgg catccttaag  840
tcaccagtgc atcgtgtagt gactaatgca gaaaaggaac gtatttcact tgcagtattc  900
tacggtgtcg gagcggagaa cgccttggag cccgccgccg gtctgcttga cgagaagcgg  960
cctgcgcgtt atcggaagat tagcatgacg gacttcatag ctggaatcca cggccagttc  1020
tcacgtggca cccgattcat cgagtcattg aagatttga                         1059

SEQ ID NO: 4           moltype = AA  length = 352
FEATURE                Location/Qualifiers
source                 1..352
                       mol_type = protein
                       organism = Zea mays
SEQUENCE: 4
MADESWRVPT PVQELAATLE EPPSRYVLQE KDRRGSPLVA DDMPEPLPVI NLSRLSEDAT  60
EAAKLESALQ SWGLVLVTNH GIETSLMDGV MDASREFFRQ PLEEKQKYSN LIDGKRFQVE  120
GYGNDRVATE RQILNWNDRL HLKVAPEDER DYTHWPKHPE SFRDVLHEYA LETKRVRDGI  180
FRATAKILEL DEDHFVRLIS DRAAAFARFN YYPPCPRPDL VNGVQPHSDA GVLTILLVDK  240
DVRGLQVQRD GVWYNVPPMP YTLLINLGDI MEIMSNGILK SPVHRVVTNA EKERISLAVF  300
YGVGAENALE PAAGLLDEKR PARYRKISMT DFIAGIHGQF SRGTRFIESL KI          352

SEQ ID NO: 5           moltype = DNA  length = 1056
FEATURE                Location/Qualifiers
source                 1..1056
                       mol_type = other DNA
                       note = codon optimized for plant
                       organism = synthetic construct
SEQUENCE: 5
atggcgggag agtcttggaa ggtgcccacg cccgtgaaag atttggccgc actggtggag  60
gagccgccgt cccagttcgt tcagcgtgag gaagaccgcc caggatctct gatgcttgct  120
gccgacatgc cggacccgct cccaatcgtt gacctagaca agatgagcac cgcagacgag  180
gccactaagc tgagaagtgc cctgcaaacc tggggactct tcctggcaac taatcacggg  240
attgatgtga gtttaatgga ggacttgatg aaggcgtcac gtgagttctt caaccagccg  300
cttcaagaac gccagaaata ctccaacttg cgagaaggaa ctcgcttcca gcttgagggt  360
tacggttctg acccagtcat tgcacaggat cacatcttgg actggagtga caggctacaa  420
ctcaaagtag agccagagga tgagcgtaac cttgctcagt ggccaaagca ccctgagtcc  480
ttccgggact tactacacga gtacgcaact aagacaaaga ccgttatggt caagatcctc  540
cgcgcgatgg ctaagaccct tgagcttgat gaggaggact tcattgacca gatcggtggt  600
aggccacaag cctacgcacg cttcaactac tatcctcctt gtcctcgacc cgagcttgtc  660
cttgggataa aggcacattc agacggtccg cttcttactg ttctcctcgt tgaccgtgag  720
gtcggtgggc tccagataca gcgtgagaac aaatggttta acgtgccatc aatccctcat  780
gcgttggtca tcaacttggg tgacagcctt gagatcatga gcaacgggat ctttaagagc  840
cctgtacaca gggtcgttac gaatgcggag aaggagcgga tttccctggc tatgctctac  900
gctgtgcaaa gggataacgt gctagagccc gcgccgggtc tcttggacga gaaacggcct  960
gccaagtacc gacgtatcac agaggctcac tttctcgaag gtgtgaagga acacttctct  1020
aagggtatgc gaatgatcga aaccctcaag atttga                            1056

SEQ ID NO: 6           moltype = AA  length = 351
FEATURE                Location/Qualifiers
source                 1..351
                       mol_type = protein
                       organism = Sorghum bicolor
SEQUENCE: 6
MAGESWKVPT PVKDLAALVE EPPSQFVQRE EDRPGSLMLA ADMPDPLPIV DLDKMSTADE  60
ATKLRSALQT WGLFLATNHG IDVSLMEDLM KASREFFNQP LQERQKYSNL REGTRFQLEG  120
YGSDPVIAQD HILDWSDRLQ LKVEPEDERN LAQWPKHPES FRDLLHEYAT KTKTVMVKIL  180
RAMAKTLELD EEDFIDQIGG RPQAYARFNY YPPCPRPELV LGIKAHSDGP LLTVLLVDRE  240
VGGLQIQREN KWFNVPSIPH ALVINLGDSL EIMSNGIFKS PVHRVVTNAE KERISLAMLY  300
AVQRDNVLEP APGLLDEKRP AKYRRITEAH FLEGVKEHFS KGMRMIETLK I           351

SEQ ID NO: 7           moltype = DNA  length = 1080
FEATURE                Location/Qualifiers
source                 1..1080
                       mol_type = other DNA
                       note = codon optimized for plant
                       organism = synthetic construct
SEQUENCE: 7
atggcaaacg aatcgtggaa gattccgatg ttggtgcaag aactcgccgc caaggtgcaa  60
gaaccgccca gtcggtacgt gcagccagag cagcagcatc cggtgagcct ggtggttgga  120
gctgagaagc ccgaggctat tcccgtgatt gatctgtcgc gtcttcttgc ggctgatgga  180
gcggatgagg agggttcgaa actccggttg gccttgcagt cctggggact gttccttatt  240
gataaccacg gcattgagac ctcactcatg gatgacctca tcaatgcttc gagggagttc  300
ttccaccttc cgctcgaaga aaagcagaag tgctctaatt tgattgacgg gaagcactat  360
caagtggagg gatacgggaa tgacccggtc gcttcgaagg accagattct ggactggctc  420
gacagattgc atctgcggt ggagccggag gatgagcgta acctagttca ttggccagag  480
catcccaaca gcttccgtgc cttgttgcac aagtacaccc ttaactgcaa gcgtatcaaa  540
gacaggatct tgtgggcgat ggctaagtct ctgggccttg acgaggacta cattgttgca  600
cagtttagtg gcaaggctcc aagtttcgcc cggtttaact attaccctcc atgcccgagg  660
ccagacatcg tgttcggagc aaagccgcac agtgacggtg gtgtcttgac catcttgctg  720
```

```
atggacaaag acgttggagg actccaagtc ctgcgtgacg gagtctggca taacgtgcct  780
accagcccac acaggcttct tgtgaacatt ggtgacttct cggagatcat gtccaacgga  840
atctttaaga gcccagtgca ccgtgtggtt accaacatgg gaaaggagcg tatcagtctt  900
gctatgttcc acgggctcga cccggagaag gagatagagc cagctaccgc actgttgcac  960
gagaagcagt tagctcggta tcgcaagatc aaagcaaagg tttacttggc gggattctac  1020
gagcacttct gccgaggcac ccgcttcatt gacagtgaag acctcaggga ggttgcatag  1080

SEQ ID NO: 8            moltype = AA  length = 359
FEATURE                 Location/Qualifiers
source                  1..359
                        mol_type = protein
                        organism = Setaria italica
SEQUENCE: 8
MANESWKIPM LVQELAAKVQ EPPSRYVQPE QQHPVSLVVG AEKPEAIPVI DLSRLLAADG  60
ADEEGSKLRL ALQSWGLFLI DNHGIETSLM DDLINASREF FHLPLEEKQK CSNLIDGKHY  120
QVEGYGNDPV ASKDQILDWL DRLHLRVEPE DERNLVHWPE HPNSFRALLH KYTLNCKRIK  180
DRILWAMAKS LGLDEDYIVA QFSGKAPSFA RFNYYPPCPR PDIVFGAKPH SDGGVLTILL  240
MDKDVGGLQV LRDGVWHNVP TSPHRLLVNI GDFSEIMSNG IFKSPVHRVV TNMGKERISL  300
AMFHGLDPEK EIEPATALLH EKQLARYRKI KAKVYLAGFY EHFCRGTRFI DSEDLREVA   359

SEQ ID NO: 9            moltype = DNA  length = 1071
FEATURE                 Location/Qualifiers
source                  1..1071
                        mol_type = other DNA
                        note = codon optimized for plant
                        organism = synthetic construct
SEQUENCE: 9
atggcttcct ccgacgagtc tccaatggtg cggccgacgg tgcaagagct tgcttcggct  60
ggagttgagg agccgcctcg acagtacgtc ctacccgagc aagatcgcca cggagacctg  120
ctggcagccg acgagtttcc cgagcccatt ccgcttatcg acctgtcacg cctcaccgac  180
gcagatgagg cagaacgtct ccgcgcagca ctccagactt ggggattctt cctggccaca  240
aatcacggga tcgagggatc gctcatggac gctatgatgt ccgtctctcg ggaattcttc  300
cgacagccag cagaggagaa acagaagtgt tcgaatcttg tggatggaaa tggcaaagac  360
tatcaagtgg agggatacgg gagcgacaag gtggtcagtg aggatcaagt cttaaactgg  420
tctgaccgtt tgcacctcag ggttgaaccc gaggacgagc gtaacttcgc taaatggcct  480
tcccaccctg agtccttccg ggacgtcttg aaggagtacg cctctcgcac taaggaaatc  540
cgcgatctcg tgctgaggtc tattgctaag ctcctcgaaa tcgacgaaga ctacttcgtg  600
aatcagataa gcaacaaggc cagcggcttc gctcggttta actactatcc tccctgcccg  660
agaccagacc tggtactagg tctcagagca cactcggacg gcggtctgtt gacaattctg  720
tttaacgacg acactgtggg cggcttacaa gttcagaggg acggaaggtg gtacaacgtg  780
agtgctaagc cgcacactct acttatcaac ctggctgact gtctggagat catgaacaac  840
gggatcttca cctctcctat tcatcgtgtc gttaccaaca tcaagaagga tcggctgtct  900
ctcgccgtgt tctacgctgt tgatgccgaa actatgctgg agccagctcc cggcctactg  960
gacgataagc gtcctcccag ataccgcaag atgttagcga aagatttcgt cgctgggtta  1020
ttcgaacact ttcggcaagg aaagcgattc atcaatactc tcaagatttg a          1071

SEQ ID NO: 10           moltype = AA  length = 356
FEATURE                 Location/Qualifiers
source                  1..356
                        mol_type = protein
                        organism = Triticum aestivum
SEQUENCE: 10
MASSDESPMV RPTVQELASA GVEEPPRQYV LPEQDRHGDL LAADEFPEPI PLIDLSRLTD  60
ADEAERLRAA LQTWGFFLAT NHGIEGSLMD AMMSVSREFF RQPAEEKQKC SNLVDGNGKD  120
YQVEGYGSDK VVSEDQVLNW SDRLHLRVEP EDERNFAKWP SHPESFRDVL KEYASRTKEI  180
RDLVLRSIAK LLEIDEDYFV NQISNKASGF ARFNYYPPCP RPDLVLGLRA HSDGGLLTIL  240
FNDDTVGGLQ VQRDGRWYNV SAKPHTLLIN LADCLEIMNN GIFTSPIHRV VTNIKKDRLS  300
LAVFYAVDAE TMLEPAPGLL DDKRPPRYRK MLAKDFVAGL FEHFRQGKRF INTLKI      356

SEQ ID NO: 11           moltype = DNA  length = 1056
FEATURE                 Location/Qualifiers
source                  1..1056
                        mol_type = other DNA
                        note = codon optimized for plant
                        organism = synthetic construct
SEQUENCE: 11
atggcttcct cctcgtggcg agttcctaca ccggtccagg aacttgcggc tggcgtggtg  60
gagccaccaa gccagttcgt attgcaagaa caggacaggc cggagtcact cctgttagca  120
gccgacatgc cggagccaat ccctgttatc gacctttccc gccttagcgc ggctgacgaa  180
gcctcaaagc tccaatcggc cttgcagacc tggggactat tcctggttac taatcacgga  240
atcgaggcga gcctaatgga cgaggtgatg gctgcctcta gggacttctt ccatcagccc  300
ttacaggaga aacagaagta cagtaatctt atcggcggga agcggtttca aatggagggt  360
tacggaaatg acatggtgac ctcccaggac cagatactcg attggcaaga caggctacag  420
ttgcgtgtcg agcctgagga tgagcgtaac cttgcttact ggcctaaaca ccctgattcg  480
ttcagagact tgctacacga gtacgcctcg aagaccaaga aagttcgtga caacctatta  540
agagcgatgg gaaagatcct tgagttgggt gacgactact tcatctccca gatcggtgag  600
aaggcgagtg ctgtagcccg cttcaactac taccctcctt gccctagacc cgagctagta  660
tttgggatta agcctcactc cgatggcgga gccgtaacca ttctgctcgt ggataatgac  720
gtaggcggac ttcaagtgca gaaggatggg atctggtata ccgtcccaag caagcctcat  780
```

```
acacttgtgg tcaacctggc agattctatg gagattatga acaatgggat cttcaaatca  840
cccgttcatc gcgtagttac caatgctgag aaagagcgcc tgagtctcgc tatgttctac  900
ggcgtagagg gccaaaaaat gctggaaccg gccgccggac tgctaggcga ggatcgccct  960
gcgcgctacc gcaagattaa ggcggctgat tacattgtgg gactccgaca agggatcgct  1020
aagggtcagc gctttatcga aaccctcaag atttga                            1056

SEQ ID NO: 12          moltype = AA  length = 351
FEATURE                Location/Qualifiers
source                 1..351
                       mol_type = protein
                       organism = Andropogon gerardii
SEQUENCE: 12
MASSSWRVPT PVQELAAGVV EPPSQFVLQE QDRPESLLLA ADMPEPIPVI DLSRLSAADE  60
ASKLQSALQT WGLFLVTNHG IEASLMDEVM AASRDFFHQP LQEKQKYSNL IGGKRFQMEG  120
YGNDMVTSQD QILDWQDRLQ LRVEPEDERN LAYWPKHPDS FRDLLHEYAS KTKKVRDNLL  180
RAMGKILELG DDYFISQIGE KASAVARFNY YPPCPRPELV FGIKPHSDGG AVTILLVDND  240
VGGLQVQKDG IWYTVPSKPH TLVVNLADSM EIMNNGIFKS PVHRVVTNAE KERLSLAMFY  300
GVEGQKMLEP AAGLLGEDRP ARYRKIKAAD YIVGLRQGIA KGQRFIETLK I           351

SEQ ID NO: 13          moltype = DNA  length = 1005
FEATURE                Location/Qualifiers
source                 1..1005
                       mol_type = other DNA
                       note = codon optimized for plant
                       organism = synthetic construct
SEQUENCE: 13
atggcttcct ccagctggaa agtgcccacg cccgtacagg agttggccgc tacgttggag  60
gagccaccct cccgctacgt cttacgcgag aaggatcggc catctagccc gttggtggca  120
gatgacatgc ccgagcctct acctgttatc aacctctctc gactgtccga agatgcggcc  180
gaggcggcta agctggaagc cgcattacaa tcctggggtc ttgtgctagt tacaaatcac  240
gggattgaaa cgagtctcat ggacgacgtg atggatacca gtagggaatt ctttaaccag  300
acattagagg agaaacagaa gtacagtaac ctcatcgaag gcaagcgatt ccagatggag  360
ggctacggaa atgacagagt ttcgacagag catcagatcc ttaactggaa cgacaggctt  420
cacctcaaag tcgctccaga cgacgagcgg aactacaccc actggcctaa acaccctgag  480
tctttccggg atgtcctaca cgagtataca cttaagacca aaaagatccg tgataacatc  540
tgttcaaatg gtcaagacat tggcgctcgc ttcaactact accctccctg tcctcgtccc  600
gacctcgtga atggagtgca gccacactcg gatgctggcg ttctgaccat cctgctggtt  660
gacaaggaga tacgcggtct gcaagtacaa agggacggca tctggtacaa cgttccgcgt  720
aaaccctaca cgctgctgat taacctcggc gatgttatgg agatcatgag taacgggatc  780
ttcaagtcac ccgttcaccg cgttgtcacc aacactgaga aagagcggat ctctctcgct  840
atgttctatg gcgtggacgc tgagaacgtc ttagagcctg ccgccgggct cctagacgag  900
aagcgtccag cccgctacag gaaggtcgag atcaccgact tcgtggcggg agttcacgag  960
cacttctcac gtggaacgag attcattgag tcactcaaga tttga                  1005

SEQ ID NO: 14          moltype = AA  length = 334
FEATURE                Location/Qualifiers
source                 1..334
                       mol_type = protein
                       organism = Coix lacryma-jobi
SEQUENCE: 14
MASSSWKVPT PVQELAATLE EPPSRYVLRE KDRPSSPLVA DDMPEPLPVI NLSRLSEDAA  60
EAAKLEAALQ SWGLVLVTNH GIETSLMDDV MDTSREFFNQ TLEEKQKYSN LIEGKRFQME  120
GYGNDRVSTE HQILNWNDRL HLKVAPDDER NYTHWPKHPE SFRDVLHEYT LKTKKIRDNI  180
CSNGQDIGAR FNYYPPCPRP DLVNGVQPHS DAGVLTILLV DKEIRGLQVQ RDGIWYNVPR  240
KPYTLLINLG DVMEIMSNGI FKSPVHRVVT NTEKERISLA MFYGVDAENV LEPAAGLLDE  300
KRPARYRKVE ITDFVAGVHE HFSRGTRFIE SLKI                              334

SEQ ID NO: 15          moltype = DNA  length = 1056
FEATURE                Location/Qualifiers
source                 1..1056
                       mol_type = other DNA
                       note = codon optimized for plant
                       organism = synthetic construct
SEQUENCE: 15
atggcttcct cctcttggcg tgtgccgaca cccgtacagg agcttgcggc gggtgtggtc  60
gagccacctt cgcagttcgt attacaagag caagacagac ccgagtcgct tctccttgca  120
acagacatgc ccgaaccgat acccgtcatt gacctatcac gacttgctgc ggcggatgag  180
gcgagtaaac tccggtccgc actccaaacg tggggactat tcctggttac taatcacggc  240
atcgaagcct cactaatgga tgacgtgatg gccgcttcca gggacttctt ctaccagcca  300
cttgaggaga aacagaagta ttcgaatctt gtcggcggca aacgctttca gatggaggga  360
tacggcaacg acatggttgc gtctcaggat caagtcctcg actggcaaga tcggcttcaa  420
cttcgagtgg agcccgagga cgagcgcaac ctggcttact ggcctaaaca tcccgactcc  480
tttagagacc ttctacacga gtacgcttcg aagaccaaaa aagttcggga taacgtcctt  540
caagctatgg gaaagctgct ggagctaggc gaagactact tcataagtca aataggtggg  600
aaagcaagcg ctattgccag attcaattac tatccaccat gccctcggcc tgagttggta  660
ttcggtatta agccgcactc cgacggaggt gcggtcacta tcctcctcgt tgacaatgac  720
gtgggcggct tgcaagtcca gaaggacggg atctggtata cagttccatc gaaacctcac  780
acattggtag ttaatctcgg agatagtatg gaaattctta acaacggaat cttcaagtcg  840
ccagtccatc gggttgtgac aaatgctgag aaggagcgcc tatcgctcgc aatgttctac  900
```

```
ggtgttgagg gtcagaaagt gttggaacct gctgcggctt tgctcggtga ggaacggcca  960
gcccgttacc gcaagattaa ggcagcagac tacatcgtcg ggctgaggca agggattgct  1020
cgtgggaaca gattcattga aaccctcaag atttga                            1056

SEQ ID NO: 16          moltype = AA  length = 351
FEATURE                Location/Qualifiers
source                 1..351
                       mol_type = protein
                       organism = Coix lacryma-jobi
SEQUENCE: 16
MASSSWRVPT PVQELAAGVV EPPSQFVLQE QDRPESLLLA TDMPEPIPVI DLSRLAAADE  60
ASKLRSALQT WGLFLVTNHG IEASLMDDVM AASRDFFYQP LEEKQKYSNL VGGKRFQMEG  120
YGNDMVASQD QVLDWQDRLQ LRVEPEDERN LAYWPKHPDS FRDLLHEYAS KTKKVRDNVL  180
QAMGKLLELG EDYFISQIGG KASAIARFNY YPPCPRPELV FGIKPHSDGG AVTILLVDND  240
VGGLQVQKDG IWYTVPSKPH TLVVNLGDSM EILNNGIFKS PVHRVVTNAE KERLSLAMFY  300
GVEGQKVLEP AAALLGEERP ARYRKIKAAD YIVGLRQGIA RGNRFIETLK I           351

SEQ ID NO: 17          moltype = DNA  length = 1056
FEATURE                Location/Qualifiers
source                 1..1056
                       mol_type = other DNA
                       note = TDO variant sequence
                       organism = synthetic construct
SEQUENCE: 17
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcggtggcc tgcaagttca gagggatggc aagtggtcca acgttccagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                            1056

SEQ ID NO: 18          moltype = AA  length = 351
FEATURE                Location/Qualifiers
source                 1..351
                       mol_type = protein
                       note = TDO variant sequence
                       organism = synthetic construct
SEQUENCE: 18
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKHFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VGGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 19          moltype = DNA  length = 1062
FEATURE                Location/Qualifiers
source                 1..1062
                       mol_type = other DNA
                       note = TDO variant sequence
                       organism = synthetic construct
SEQUENCE: 19
atggctgacg agtcatggag ggcgccggcg atagtgcaag agctggcggc agccggcgtc  60
gaggagccgc cgagccgata cctgctacgg gagaaagacc gttctgacgt caagctggtc  120
gccgccgagc tgccggagcc tctcccagtc gttgatctca gccggctaga tggtgccgag  180
gaggccacca agctcagggt ggctctgcag aattggggct tcttcctgct taccaaccat  240
ggagtagaag cctctctgat ggacagcgtg atgaacttgt cgagagagtt cttcaaccag  300
ccaatcgaac ggaagcagaa attcagcaac ttgatcgatg gcaacggtaa gaacttccag  360
attcaagggt atggaactga ccgggtggtt acccaagatc agatcctgga ctggtctgat  420
cggttgcatc tcagagttga acccaaggag gagcaagatc ttgccttctg gcctgaccat  480
cctgaatctt tcagggatgt tctgaacaag tatgcatcag gaactaaaag aattagagac  540
gatatcattc aggctatggc caagactctt gagcttgatg aggattactt cgttaaccaa  600
tttaacaagg cttctactta tgcaagattc aactactacc ctccctgtcc aaggcctgac  660
cttgtgttcg gcatcaggcc tcactccgac ggcaccctct tgacgattct tctcgtcgac  720
aaagatgtcg gtggcctgca agttcttagg gatggcactt ggtataacgt tccaacttct  780
cctcacacat tgctgatcaa cttaggtgac accatggagg taatgtgcaa tggcatcttc  840
aggagcccgg tgcacagggt ggtgacaaac gccgagaagg agaggatctc cctggccatg  900
```

```
ttatacagcg tgaacgatga gaaagacatt gagccggcgg ctggtttgct ggatgagaat  960
cggcctgcaa gatacaggaa agtgagcgtc gaagagttca gggccgggat ctttggaaaa  1020
ttctctcgag gagagaggta catcgactcc ctgaggatct ga                     1062

SEQ ID NO: 20          moltype = AA  length = 353
FEATURE                Location/Qualifiers
source                 1..353
                       mol_type = protein
                       note = TDO variant sequence
                       organism = synthetic construct
SEQUENCE: 20
MADESWRAPA IVQELAAAGV EEPPSRYLLR EKDRSDVKLV AAELPEPLPV VDLSRLDGAE  60
EATKLRVALQ NWGFFLLTNH GVEASLMDSV MNLSREFFNQ PIERKQKFSN LIDGNGKNFQ  120
IQGYGTDRVV TQDQILDWSD RLHLRVEPKE EQDLAFWPDH PESFRDVLNK YASGTKRIRD  180
DIIQAMAKTL ELDEDYFVNQ FNKASTYARF NYYPPCPRPD LVFGIRPHSD GTLLTILLVD  240
KDVGGLQVLR DGTWYNVPTS PHTLLINLGD TMEVMCNGIF RSPVHRVVTN AEKERISLAM  300
LYSVNDEKDI EPAAGLLDEN RPARYRKVSV EEFRAGIFGK FSRGERYIDS LRI         353

SEQ ID NO: 21          moltype = DNA  length = 1059
FEATURE                Location/Qualifiers
source                 1..1059
                       mol_type = other DNA
                       note = TDO variant sequence
                       organism = synthetic construct
SEQUENCE: 21
atggctgacg agtcatggag gattccggcg atagtgcaag agctggcggc aaagggcgtc  60
gaggagccgc cgagccgata cctgctacgg gagaaagaac gttctgacgt caaggctgtc  120
gccgccgagc tgccggagcc tattccagtc attgatctca gccggctaga tggtgccgag  180
gaggccacca agctcaggtc tgctctgcag aattggggct tcttcctgct taccaaccat  240
ggaattgaag cctctctgat ggacagcgtg atgtctgctt cgagagagtt cttcaaccag  300
ccaatcgaac ggaagcagaa atgcagcaac ttgatcgatg gcaagaactt ccagattcaa  360
gggtatggaa ctgacccagt ggttacccaa gatcagatcc tggactggtc tgatcggttg  420
catctcagag ttgaacccaa ggaggagaga gatcttgccc attggcctga ccatcctgaa  480
tctttcaggg atgttctgaa caagtatgca tcaggatgca aaagaattag agacgatatc  540
cttcaggcta tggccaagct tcttgagctt gatgaggatt acttcttgga ccaactcggt  600
aacgaagctc ctgcattcgc aagattcaac tactaccctc cctgtccaag gcctgacctt  660
gtgcttggca tcaggcctca ctccgacggc accctcttga cgattcttct cgtcgacaaa  720
gatgtcagtg gcctgcaagt tcagagggat ggcaagtggt ataacgttga ggcaactcct  780
cacacattgc tgatcaactt aggtgacacc atggaggtaa tgtgcaatgg catcttcagg  840
agcccggtgc acagggtggt gacaaacgcc gagaaggaga ggatctccct ggccatgtta  900
tacagcgtga acgatgagaa agacattgag ccggcggctg gtttgctgga tgagaatcgg  960
cctgcaagat acaggaaagt gagcgtcgaa gagttcaggg ccgggatctt tggaaaattc  1020
tctcgaggag agaggtacat cgactccctg aggatctga                         1059

SEQ ID NO: 22          moltype = AA  length = 352
FEATURE                Location/Qualifiers
source                 1..352
                       mol_type = protein
                       note = TDO variant sequence
                       organism = synthetic construct
SEQUENCE: 22
MADESWRIPA IVQELAAKGV EEPPSRYLLR EKERSDVKAV AAELPEPIPV IDLSRLDGAE  60
EATKLRSALQ NWGFFLLTNH GIEASLMDSV MSASREFFNQ PIERKQKCSN LIDGKNFQIQ  120
GYGTDPVVTQ DQILDWSDRL HLRVEPKEER DLAHWPDHPE SFRDVLNKYA SGCKRIRDDI  180
LQAMAKLLEL DEDYFLDQLG NEAPAFARFN YYPPCPRPDL VLGIRPHSDG TLLTILLVDK  240
DVSGLQVQRD GKWYNVEATP HTLLINLGDT MEVMCNGIFR SPVHRVVTNA EKERISLAML  300
YSVNDEKDIE PAAGLLDENR PARYRKVSVE EFRAGIFGKF SRGERYIDSL RI          352

SEQ ID NO: 23          moltype = DNA  length = 1056
FEATURE                Location/Qualifiers
source                 1..1056
                       mol_type = other DNA
                       note = TDO variant sequence
                       organism = synthetic construct
SEQUENCE: 23
atggctgacg agtcatggag gattccggcg atagtgcaag agctggcggc agccggcgtc  60
gaggagccgc cgagccgata cctgctacca gagaaagacc gttctgacgt caaggctgtc  120
ggtgccgagc tgccggagcc tctcccagtc attgatctcg gtcggctaga tgatgccgag  180
gaggccacca agctcagggt ggctctgcag aattggggct tcttcctgct ttctaaccat  240
ggagtagaag cctctctgat ggacgatgtg atgaacgctt cgagagagtt cttcaaccag  300
ccaatcgaag aaaagcagaa attcagcaac ttgatcgatg gcaagaactt ccagattgaa  360
gggtatggaa ctgaccgggt ggttacccaa gatcagatcc tggactggtc tgatcggttg  420
catctcagag ttgaacccaa ggaggagcaa gatcttgcct tctggcctga ccatcctgaa  480
tctttcaggg atgttctgaa caagtatgca tcaggatgca aaagaattag agacgatatc  540
cttcaggcta tggccaagac tcttgagctt gatgaggatt acttcttgga ccgactcaac  600
gaagcttctg cattcgcaag attcaactac taccctccct gtccaaggcc tgaccttgtg  660
ttcggcgtta ggcctcactc cgacggcggt ctcttgacga ttcttctcgt cgacaaagat  720
gtcagtggcc tgcaagttct tagggatggc aagtggtcca acgttgaggc aactcctcac  780
acattgctga tcaacttagg tgactctatg gaggtaatgt gcaatggcat cttcaggagc  840
```

```
ccggtgcaca gggtggtgac aaacactgag aaggagagga tctccctggc catgttatac  900
ggtgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                            1056

SEQ ID NO: 24          moltype = AA  length = 351
FEATURE                Location/Qualifiers
source                 1..351
                       mol_type = protein
                       note = TDO variant sequence
                       organism = synthetic construct
SEQUENCE: 24
MADESWRIPA IVQELAAAGV EEPPSRYLLP EKDRSDVKAV GAELPEPLPV IDLGRLDDAE  60
EATKLRVALQ NWGFFLLSNH GVEASLMDDV MNASREFFNQ PIEEKQKFSN LIDGKNFQIE  120
GYGTDRVVTQ DQILDWSDRL HLRVEPKEEQ DLAFWPDHPE SFRDVLNKYA SGCKRIRDDI  180
LQAMAKTLEL DEDYFLDRLN EASAFARFNY YPPCPRPDLV FGVRPHSDGG LLTILLVDKD  240
VSGLQVLRDG KWSNVEATPH TLLINLGDSM EVMCNGIFRS PVHRVVTNTE KERISLAMLY  300
GVNDEKDIEP AAGLLDENRP ARYRKVSVEE FRAGIFGKFS RGERYIDSLR I           351

SEQ ID NO: 25          moltype = DNA  length = 1056
FEATURE                Location/Qualifiers
source                 1..1056
                       mol_type = other DNA
                       note = TDO variant sequence
                       organism = synthetic construct
SEQUENCE: 25
atggctgacg agtcatggag ggcgccggcg cttgtgcaag agctggcggc aaagggcgtc  60
gaggagccgc cgagccgata cctgctacca gagaaagacc gttctgacgt caagctggtc  120
gccgccgaga tgccggagcc tattccagtc gttgatctca gccggctaga tgatgccgag  180
gaggccacca agctcaggtc tgctctgcag aattggggct tcttcctgct taccaaccat  240
ggagtagaag cctctctgat ggacagcgtg atgaacgctt cgagagagtt cttcaaccag  300
ccaatcgaac ggaagcagaa attcagcaac ttgatcgatg gcaagaactt ccagattgaa  360
gggtatggaa ctgacccagt ggttacccaa gatcaggttc tggactggtc tgatcggttg  420
catctcagag ttgaacccaa ggaggagaga gatcttgcct tctggcctga ccatcctgaa  480
tctttcaggg atgttctgaa cgaatatgca tcaggaacta aaagaattag agacgatatc  540
attcaggcta tggccaagct tcttgagctt gatgaggatt acttcttgga ccgactcaac  600
aaggcttctg cattcgcaag attcaactac taccctccct gtccaaggcc tgaccttgtg  660
cttggcgtta ggcctcactc cgacggcggt ctcttgacga ttcttctcgt cgacaaagat  720
gtcagtggcc tgcaagttca gagggatggc aagtggtata acgttgaggc aactcctcac  780
acattgctga tcaacttagg tgacaccatg gaggtaatgt gcaatggcat cttcaggagc  840
ccggtgcaca gggtggtgac aaacgccgag aaggagagga tctccctggc catgttttac  900
ggtgtggatg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                            1056

SEQ ID NO: 26          moltype = AA  length = 351
FEATURE                Location/Qualifiers
source                 1..351
                       mol_type = protein
                       note = TDO variant sequence
                       organism = synthetic construct
SEQUENCE: 26
MADESWRAPA LVQELAAKGV EEPPSRYLLP EKDRSDVKLV AAEMPEPIPV VDLSRLDDAE  60
EATKLRSALQ NWGFFLLTNH GVEASLMDSV MNASREFFNQ PIERKQKFSN LIDGKNFQIE  120
GYGTDPVVTQ DQVLDWSDRL HLRVEPKEER DLAFWPDHPE SFRDVLNEYA SGTKRIRDDI  180
IQAMAKLLEL DEDYFLDRLN KASAFARFNY YPPCPRPDLV LGVRPHSDGG LLTILLVDKD  240
VSGLQVQRDG KWYNVEATPH TLLINLGDTM EVMCNGIFRS PVHRVVTNAE KERISLAMFY  300
GVDDEKDIEP AAGLLDENRP ARYRKVSVEE FRAGIFGKFS RGERYIDSLR I           351

SEQ ID NO: 27          moltype = DNA  length = 1056
FEATURE                Location/Qualifiers
source                 1..1056
                       mol_type = other DNA
                       note = TDO variant sequence
                       organism = synthetic construct
SEQUENCE: 27
atggctgacg agtcatggag ggcgccggcg cttgtgcaag agctggcggc aaagggcgtc  60
gaggagccgc cgagccgata cctgctacgg gagcaagacc gtagcgacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagaattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcggtggcc tgcaagttca gagggatggc aagtggtcca acgttccagc aactcctcac  780
```

```
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 28          moltype = AA  length = 351
FEATURE                Location/Qualifiers
source                 1..351
                       mol_type = protein
                       note = TDO variant sequence
                       organism = synthetic construct
SEQUENCE: 28
MADESWRAPA LVQELAAKGV EEPPSRYLLR EQDRSDVKLV AAELPEPIPV VDLGRLDGAE  60
EATKLRVALQ NWGFFLLTNH GIEASLMDDV MNLSREFFNQ PIERKQKFSN LIDGKNFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VGGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 29          moltype = DNA  length = 1056
FEATURE                Location/Qualifiers
source                 1..1056
                       mol_type = other DNA
                       note = TDO variant sequence
                       organism = synthetic construct
SEQUENCE: 29
atggctgacg agtcatggag ggcgccggcg cttgtgcaag agctggcggc aaagggcgtc  60
gaggagccgc cgagccgata cctgctacgg gagcaagacc gtagcgacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattcag  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcggtggcc tgcaagttca gagggatggc aagtggtcca acgttccagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 30          moltype = AA  length = 351
FEATURE                Location/Qualifiers
source                 1..351
                       mol_type = protein
                       note = TDO variant sequence
                       organism = synthetic construct
SEQUENCE: 30
MADESWRAPA LVQELAAKGV EEPPSRYLLR EQDRSDVKLV AAELPEPIPV VDLGRLDGAE  60
EATKLRVALQ NWGFFLLTNH GIEASLMDDV MNLSREFFNQ PIERKQKFSN LIDGKHFQIQ  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VGGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 31          moltype = DNA  length = 1056
FEATURE                Location/Qualifiers
source                 1..1056
                       mol_type = other DNA
                       note = TDO variant sequence
                       organism = synthetic construct
SEQUENCE: 31
atggctgacg agtcatggag ggcgccggcg cttgtgcaag agctggcggc aaagggcgtc  60
gaggagccgc cgagccgata cctgctacgg gagcaagacc gtagcgacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
```

```
gtcagcggcc tgcaagttca gagggatggc aagtggtcca acgttccagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                           1056

SEQ ID NO: 32          moltype = AA  length = 351
FEATURE                Location/Qualifiers
source                 1..351
                       mol_type = protein
                       note = TDO variant sequence
                       organism = synthetic construct
SEQUENCE: 32
MADESWRAPA LVQELAAKGV EEPPSRYLLR EQDRSDVKLV AAELPEPIPV VDLGRLDGAE  60
EATKLRVALQ NWGFFLLTNH GIEASLMDDV MNLSREFFNQ PIERKQKFSN LIDGKHFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I          351

SEQ ID NO: 33          moltype = DNA  length = 1056
FEATURE                Location/Qualifiers
source                 1..1056
                       mol_type = other DNA
                       note = TDO variant sequence
                       organism = synthetic construct
SEQUENCE: 33
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagaattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcagcggcc tgcaagttca gagggatggc aagtggtcca acgttccagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                           1056

SEQ ID NO: 34          moltype = AA  length = 351
FEATURE                Location/Qualifiers
source                 1..351
                       mol_type = protein
                       note = TDO variant sequence
                       organism = synthetic construct
SEQUENCE: 34
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKNFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I          351

SEQ ID NO: 35          moltype = DNA  length = 1056
FEATURE                Location/Qualifiers
source                 1..1056
                       mol_type = other DNA
                       note = TDO variant sequence
                       organism = synthetic construct
SEQUENCE: 35
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattcag  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
```

```
ttcggcatca ggcctcactc cgacggcggt ctcttgacga ttcttctcgt cgacaaagat  720
gtcagcggcc tgcaagttca gagggatggc aagtggtcca acgttccagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 36           moltype = AA  length = 351
FEATURE                 Location/Qualifiers
source                  1..351
                        mol_type = protein
                        note = TDO variant sequence
                        organism = synthetic construct
SEQUENCE: 36
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKHFQIQ  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVPATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 37           moltype = DNA  length = 1056
FEATURE                 Location/Qualifiers
source                  1..1056
                        mol_type = other DNA
                        note = TDO variant sequence
                        organism = synthetic construct
SEQUENCE: 37
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcagcggcc tgcaagttca gagggatggc aagtggtcca acgttgaagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 38           moltype = AA  length = 351
FEATURE                 Location/Qualifiers
source                  1..351
                        mol_type = protein
                        note = TDO variant sequence
                        organism = synthetic construct
SEQUENCE: 38
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKHFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVEATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 39           moltype = DNA  length = 1056
FEATURE                 Location/Qualifiers
source                  1..1056
                        mol_type = other DNA
                        note = TDO variant sequence
                        organism = synthetic construct
SEQUENCE: 39
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
```

```
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcagcggcc tgcaagttca gagggatggc aagtggtcca acgttccagc aactcctcac  780
acattgctga tcaacttagg tgacaccatg gaggtaatgt gcaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 40          moltype = AA  length = 351
FEATURE                Location/Qualifiers
source                 1..351
                       mol_type = protein
                       note = TDO variant sequence
                       organism = synthetic construct
SEQUENCE: 40
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKHFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVPATPH TLLINLGDTM EVMCNGIFKS PVHRVVTNAE KERISLAMLY  300
SVNDEKDIEP AAGLLDENRP ARYRKVSVEE FRAGIFGKFS RGERYIDSLR I           351

SEQ ID NO: 41          moltype = DNA  length = 1056
FEATURE                Location/Qualifiers
source                 1..1056
                       mol_type = other DNA
                       note = TDO variant sequence
                       organism = synthetic construct
SEQUENCE: 41
atggctgacg agtcatggag ggcgccggcg cttgtgcaag agctggcggc aaagggcgtc  60
gaggagccgc cgagccgata cctgctacgg gagaaagacc gtccagacgt caagctggtc  120
gccgccgagc tgccggagcc tctgccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcagattc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
attcaggcta tggccaagct tcttgagctt gatgaggatt acttcttgga ccgatttaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcagcggcc tgcaagttca gagggatggc aagtggtcca acgttgaagc aactcctcac  780
acattgctga tcaacttagg tgacaccatg gaggtaatgt ctaatggcat cttcaagagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056

SEQ ID NO: 42          moltype = AA  length = 351
FEATURE                Location/Qualifiers
source                 1..351
                       mol_type = protein
                       note = TDO variant sequence
                       organism = synthetic construct
SEQUENCE: 42
MADESWRAPA LVQELAAKGV EEPPSRYLLR EKDRPDVKLV AAELPEPLPV VDLGRLDGAE  60
EATKLRVALQ NWGFFLLTNH GIEASLMDDV MNLSREFFNQ PIERKQKFSN LIDGKHFQIE  120
GYGTDRVVTQ DQILDWSDRL HLRVEPKEEQ DLAFWPDHPE SFRDVLHKYA SGCKRIRDDI  180
IQAMAKLLEL DEDYFLDRFN EAPTFARFNY YPPCPRPDLV FGIRPHSDGG LLTILLVDKD  240
VSGLQVQRDG KWSNVEATPH TLLINLGDTM EVMSNGIFKS PVHRVVTNAE KERISLAMLY  300
SVNDEKDIEP AAGLLDENRP ARYRKVSVEE FRAGIFGKFS RGERYIDSLR I           351

SEQ ID NO: 43          moltype = DNA  length = 1056
FEATURE                Location/Qualifiers
source                 1..1056
                       mol_type = other DNA
                       note = TDO variant sequence
                       organism = synthetic construct
SEQUENCE: 43
atggctgacg agtcatggag ggcgccggcg cttgtgcaag agctggcggc aaagggcgtc  60
gaggagccgc cgagccgata cctgctacgg gagcaagacc gtccagacgt caagctggtc  120
gccgccgagc tgccggagcc tattccagtc gttgatctcg gtcggctaga tggtgccgag  180
gaggccacca agctcagggt ggctctgcag aattggggct tcttcctgct taccaaccat  240
ggaattgaag cctctctgat ggacgatgtg atgaacttgt cgagagagtt cttcaaccag  300
ccaatcgaac ggaagcagaa attcagcaac ttgatcgatg gcaagcattt ccagattgaa  360
gggtatggaa ctgaccgggt ggttacccaa gatcaggttc tggactggtc tgatcggttg  420
catctcagag ttgaacccaa ggaggagcaa gatcttgcct tctggcctga ccatcctgaa  480
tctttcaggg atgttctgca taagtatgca tcaggatgca aaagaattag agacgatatc  540
```

```
attcaggcta tggccaagct tcttgagctt gatgaggatt acttcttgga ccgactgaac  600
gaagctccta ctttcgcaag attcaactac taccctccct gtccaaggcc tgaccttgtg  660
ttcggcatca ggcctcactc cgacggcggt ctcttgacga ttcttctcgt cgacaaagat  720
gtcggtggcc tgcaagttca gagggatggc aagtggtcca acgttccagc aactcctcac  780
acattgctga tcaacttagg tgacaccatg gaggtaatgt ctaatggcat cttccgtagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctag                            1056
```

```
SEQ ID NO: 44          moltype = AA  length = 351
FEATURE                Location/Qualifiers
source                 1..351
                       mol_type = protein
                       note = TDO variant sequence
                       organism = synthetic construct
SEQUENCE: 44
MADESWRAPA LVQELAAKGV EEPPSRYLLR EQDRPDVKLV AAELPEPIPV VDLGRLDGAE  60
EATKLRVALQ NWGFFLLTNH GIEASLMDDV MNLSREFFNQ PIERKQKFSN LIDGKHFQIE  120
GYGTDRVVTQ DQVLDWSDRL HLRVEPKEEQ DLAFWPDHPE SFRDVLHKYA SGCKRIRDDI  180
IQAMAKLLEL DEDYFLDRLN EAPTFARFNY YPPCPRPDLV FGIRPHSDGG LLTILLVDKD  240
VGGLQVQRDG KWSNVPATPH TLLINLGDTM EVMSNGIFRS PVHRVVTNAE KERISLAMLY  300
SVNDEKDIEP AAGLLDENRP ARYRKVSVEE FRAGIFGKFS RGERYIDSLR I           351
```

```
SEQ ID NO: 45          moltype = DNA  length = 1056
FEATURE                Location/Qualifiers
source                 1..1056
                       mol_type = other DNA
                       note = TDO variant sequence
                       organism = synthetic construct
SEQUENCE: 45
atggcagacg agtcgtggcg tgccccagcc ctagttcaag aacttgcggc taaaggggtt  60
gaggaaccac ctagccgtta cctcctccgt gagcaagatc gacctgatgt taaactggtc  120
gcggctgaac ttccagaacc tatcccggtt gtggatttgg gtcgtttaga tggagccgag  180
gaagctacaa agttgagagt tgcattgcaa aactggggat tctttctcct tactaatcat  240
ggtattgaag caagcctcat ggatgatgtt atgaacctat cgagggaatt cttcaatcag  300
cctattgaac gcaagcaaaa gttctcgaat cttattgatg gaaaacactt tcaaatcgag  360
ggttatggta cagacagagt agtcactcaa gatcaagtat tggattggtc tgatcggttg  420
catctcagag tagaaccgaa agaggagcaa gacttggctt tctggccgga ccacccggaa  480
tcctttcgtg acgtactaca caagtacgcc agcggctgta aacgcatcag agacgacatc  540
attcaagcaa tggcaaaact ccttgaattg gatgaagatt actttctgga tcgcttcaac  600
gaagcaccaa cctttgctcg attcaactat taccctcctt gtccacgtcc cgacctagtg  660
ttcggcatcc gacctcattc tgatggtgga ctcctgacca tccttctagt ggataaggat  720
gtgagtggac tgcaagtcca gagggatgga aaatggtcaa atgttgaagc aaccccacat  780
actctgctta tcaatctggg agacacgatg gaagtcatgt caaatggcat attcaaatcg  840
ccagtgcacc gtgtggttac aaatgctgaa aaggaacgaa tatcactagc tatgctctat  900
tctgtcaacg acgagaagga tattgaacct gcggctggat tactagatga gaatcgtcct  960
gcacgttatc gtaaagtatc tgtagaggaa tttcgtgccg gtatcttcgg gaagttctct  1020
aggggagagc gctacattga ctcattaaga atatga                            1056
```

```
SEQ ID NO: 46          moltype = DNA  length = 1056
FEATURE                Location/Qualifiers
source                 1..1056
                       mol_type = other DNA
                       note = TDO variant sequence
                       organism = synthetic construct
SEQUENCE: 46
atggctgatg agtcttggag agcaccagca ctagttcaag aactagctgc taaaggagtc  60
gaggaaccac cttctcgcta tctacttcgt gaaaaggatc gtcctgatgt taaactcgtt  120
gctgctgaac ttcctgaacc acttccagta gtggaccttg gcagactcga tggtgcggag  180
gaagctacta aacttcgagt tgctttgcaa aactggggat tcttcctact taccaaccat  240
ggcatagaag cttctctaat ggatgatgtt atgaacctgt ctcgagagtt tttcaaccag  300
cctattgaaa ggaaacagaa attctcaaat ctaattgatg gcaagcattt ccaaattgaa  360
ggatatggaa ccgatagagt cgtaacacaa gaccagatct tagactggtc agataggctg  420
cacctaagag tagaacctaa agaggaacaa gatttggcgt tctggcctga tcatccagaa  480
tcattcagag atgttctcca taagtatgct tctggttgca aacgtattcg ggatgacata  540
attcaagcta tggcaaaact tttagaattg gatgaagact acttcctcga tagattcaac  600
gaagctccaa ctttcgcacg gttcaactat taccctccat gtccacgtcc agacctcgtg  660
ttcggaatac gtccacattc agatggtggc ctattaacta tcctgctagt tgataaggac  720
gtatcagggc tgcaagttca aagggatgga aaatggtcaa atgttgaagc tacgcctcac  780
acgctgctga ttaacctagg cgatacaatg gaagttatgt ctaatggcat cttcaaatcg  840
cccgttcatc gagttgttac aaatgccgag aaggaacgaa tctcattagc tatgctctac  900
tctgttaatg acgagaagga cattgaacca gctgctggct tgctggatga gaataggcca  960
gcacgctatc gtaaagttag tgttgaggag tttcgagctg gaatcttcgg caaattctca  1020
cgtggtgaac ggtacatcga ctctttgcgg atttga                            1056
```

```
SEQ ID NO: 47          moltype = DNA  length = 1053
FEATURE                Location/Qualifiers
source                 1..1053
                       mol_type = other DNA
                       note = TDO variant sequence
                       organism = synthetic construct
SEQUENCE: 47
atggcaggtg aaagttggaa agtacccacg cccgtaaaag acttagctgc tctggtggaa  60
gaacccccgt ctcaattcgt gcagcgcgaa gaggatcgtc caggatcact gatgttagcg  120
gccgacatgc cagacccctt gcctattgtg gaccttgata aaatgagtac tgcagacgag  180
gcaacgaaat tgcgttctgc cttgcaaaca tgggggttgt ttcttgccac gaaccacggg  240
attgacgtat cgttaatgga agaccttatg aaggcctcgc gtgaattctt taatcagccg  300
ttgcaagaac gccagaaata ttccaactta cgcgaaggga cacgtttcca actggaagga  360
tacggatctg acccggttat cgcgcaagac catatcttag actggtcgga tcgtcttcag  420
cttaaagttg aaccggagga cgaacgtaat ttagcgcagt ggcctaaaca tccagaatcc  480
tttcgcgatc tgttacatga gtatgctacg aaaaccaaaa ccgtaatggt gaaaatctta  540
cgtgccatgg cgaagacctt agagctggat gaagaggatt ttatcgacca gattggcgga  600
cgtcctcagg catatgcgcg ttttaattac taccccccct gtccgcgtcc cgagttggtt  660
ctgggaatta aggcgcattc tgatggcacc ttacttacgg tattattagt ggaccgtgaa  720
gtgggggggtc tgcagattca gcgcgaaaac aagtggttca atgtcccttc gattcctcat  780
gccttggtga ttaaccttgg agactcattg gagattatga gcaacggcat tttcaagtcc  840
ccggttcatc gcgtggttac gaatgccgaa aaagagcgca tcagcttggc tatgctttat  900
tctgttcaac gcgataatgt attggagcct gctcctggat tacttgacga gaagcgcccg  960
gcaaagtatc gccgcatcac tgaagctcac tttcgcgcgg gtattaagga acacttctca  1020
aaaggaatgc gtatgatcga aacacttaaa atc                              1053

SEQ ID NO: 48          moltype = AA  length = 351
FEATURE                Location/Qualifiers
source                 1..351
                       mol_type = protein
                       note = TDO variant sequence
                       organism = synthetic construct
SEQUENCE: 48
MAGESWKVPT PVKDLAALVE EPPSQFVQRE EDRPGSLMLA ADMPDPLPIV DLDKMSTADE  60
ATKLRSALQT WGLFLATNHG IDVSLMEDLM KASREFFNQP LQERQKYSNL REGTRFQLEG  120
YGSDPVIAQD HILDWSDRLQ LKVEPEDERN LAQWPKHPES FRDLLHEYAT KTKTVMVKIL  180
RAMAKTLELD EEDFIDQIGG RPQAYARFNY YPPCPRPELV LGIKAHSDGT LLTVLLVDRE  240
VGGLQIQREN KWFNVPSIPH ALVINLGDSL EIMSNGIFKS PVHRVVTNAE KERISLAMLY  300
SVQRDNVLEP APGLLDEKRP AKYRRITEAH FRAGIKEHFS KGMRMIETLK I           351

SEQ ID NO: 49          moltype = DNA  length = 1056
FEATURE                Location/Qualifiers
source                 1..1056
                       mol_type = genomic DNA
                       organism = Oryza sativa
SEQUENCE: 49
atggctgacg agtcatggag ggcgccggcg atagtgcaag agctggcggc agccggcgtc  60
gaggagccgc cgagccgata cctgctacgg gagaaagacc gttctgacgt caagctggtc  120
gccgccgagc tgccggagcc cctccccgtc gttgatctca gccggctaga tggtgccgag  180
gaggccacca agctcagggt ggctctgcag aattggggct tcttcctgct taccaaccat  240
ggagtagaag cctctctgat ggacagcgtg atgaacttgt cgagagagtt tttcaaccaa  300
ccaatcgaac ggaagcaaaa attcagcaac ttgatcgatg gcaagaactt ccagattcaa  360
gggtatggaa ctgaccgggt ggttacccaa gatcagatcc tggactggtc tgatcggttg  420
catctcagag ttgaacccaa ggaggagcaa gatcttgcct tctggcctga ccatcctgaa  480
tctttcaggg atgttctgaa caagtatgca tcaggaacca aaagaattag agacgatatc  540
attcaggcta tggccaagct tcttgagctt gatgaggatt acttcttgga ccgactcaac  600
gaagctcctg catttgcaag attcaactac taccctccct gtccaaggcc tgaccttgtg  660
ttcggcatca ggcctcactc cgacggcacc ctcttgacga ttcttctcgt cgacaaagat  720
gtcagtggcc tgcaagttca gagggatggc aagtggtcca acgttgaggc aactcctcac  780
acattgctga tcaacttagg tgacaccatg gaggtaatgt gcaatggcat cttcaggagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                           1056

SEQ ID NO: 50          moltype = AA  length = 356
FEATURE                Location/Qualifiers
source                 1..356
                       mol_type = protein
                       organism = Arabidopsis thaliana
SEQUENCE: 50
MVAVERVESL AKSGIISIPK EYIRPKEELE SINDVFLEEK KEDGPQVPTI DLKNIESDDE  60
KIRENCIEEL KKASLDWGVM HLINHGIPAD LMERVKKAGE EFFSLSVEEK EKYANDQATG  120
KIQGYGSKLA NNASGQLEWE DYFFHLAYPE EKRDLSIWPK TPSDYIEATS EYAKCLRLLA  180
TKVFKALSVG LGLEPDRLEK EVGGLEELLL QMKINYYPKC PQPELALGVE AHTDVSALTF  240
ILHNMVPGLQ LFYEGKWVTA KCVPDSIVMH IGDTLEILSN GKYKSILHRG LVNKEKVRIS  300
WAVFCEPPKD KIVLKPLPEM VSVESPAKFP PRTFAQHIEH KLFGKEQEEL VSEKND      356
```

-continued

```
SEQ ID NO: 51          moltype = AA  length = 359
FEATURE                Location/Qualifiers
source                 1..359
                       mol_type = protein
                       organism = Glycine max
SEQUENCE: 51
MEPTSLTVPF VQEIAKDALT RVPERYVRPL HERPILLSAT TTPLPQVPVI DLSKLLSQDL  60
KEPELEKLHY ACKEWGFFQL INHGVSTSLV EKVKRGAQDF FNLPIEEKKK LGQREGEGVE  120
GYGQAFVVSE EQKLEWADMF FMLTLPPHIR KPYLFPNIPL PFRDDLETYS AGLKKLAIQI  180
VELMANALNV DSKEIRELFG EGVQSMRMNY YPPCPQPELV MGLNPHTDGG SLTILLQLNE  240
VEGLQIKIDG SWIPIKPLPN AFIVNLGDMM EIMTNGIYRS IEHRATVNLE KERLSIATFY  300
NPGMEVKLGP APSLVTPTTP AVFKTISVPE YYRGYLSREL RGRSYLDSMK IQNEDENSS   359

SEQ ID NO: 52          moltype = AA  length = 348
FEATURE                Location/Qualifiers
source                 1..348
                       mol_type = protein
                       organism = Arabidopsis thaliana
SEQUENCE: 52
MEKPKFKTVQ EVVAAGEGLP ERYLHAPTGD GEVQPLNAAV PEMDIPAIDL NLLLSSSEAG  60
QQELSKLHSA LSTWGVVQVM NHGITKAFLD KIYKLTKEFF ALPTEEKQKC AREIDSIQGY  120
GNDMILWDDQ VLDWIDRLYI TTYPEDQRQL NFWPEVPLGF RETLHEYTMK QRIVIEQFFK  180
AMARSLELEE NSFLDMYGES ATLDTRFNMY PPCPSPDKVI GVKPHADGSA ITLLLPDKDV  240
GGLQFQKDGK WYKAPIVPDT ILINVGDQME IMSNGIYKSP VHRVVTNREK ERISVATFCI  300
PGADKEIQPV NELVSEARPR LYKTVKKYVE LYFKYYQQGR RPIEAALI               348

SEQ ID NO: 53          moltype = AA  length = 354
FEATURE                Location/Qualifiers
source                 1..354
                       mol_type = protein
                       organism = Nicotiana tabacum
SEQUENCE: 53
MAGLSPITAD IGCKLVQEIV KDGDEIPDKY VSKDFQYGAI EEDVPIIDIP VVDMKVLTSS  60
SACGREELGK LQSALSSWGC FQFQAINHGI EESIIDEVHK ASRQFFDLSM EEKQKYGRAA  120
DDMDGYGNDM VLSENQTLDW TDRIYLLVHP EDERKLKYWP ENPKSFREIL EEYSSRLKLI  180
AEELLKSMAR CLNLPDDRFL KQYGDRPVIY ARFNFYPPCP RPKLVRGLKS HADGSAITIL  240
LQDKEVEGLQ ILKDNKWYRV PIMPYAFLVN VGDQVEIMSN GLLKSPVHRA VTNSEKERIS  300
VATFFSPESG SDIEPVEELI DDKRPRLYKT AKDYLSTYFQ YYQQGKRPLD AVKI         354

SEQ ID NO: 54          moltype = AA  length = 355
FEATURE                Location/Qualifiers
source                 1..355
                       mol_type = protein
                       organism = Arabidopsis thaliana
SEQUENCE: 54
VAVERVESLA KSGIISIPKE YIRPKEELES INDVFLEEKK EDGPQVPTID LKNIESDDEK  60
IRENCIEELK KASLDWGVMH LINHGIPADL MERVKKAGEE FFSLSVEEKE KYANDQATGK  120
IQGYGSKLAN NASGQLEWED YFFHLAYPEE KRDLSIWPKT PSDYIEATSE YAKCLRLLAT  180
KVFKALSVGL GLEPDRLEKE VGGLEELLLQ MKINYYPKCP QPELALGVEA HTDVSALTFI  240
LHNMVPGLQL FYEGKWVTAK CVPDSIVMHI GDTLEILSNG KYKSILHRGL VNKEKVRISW  300
AVFCEPPKDK IVLKPLPEMV SVESPAKFPP RTFAQHIEHK LFGKEQEELV SEKND        355
```